(12) United States Patent
Hanao et al.

(10) Patent No.: US 7,884,259 B2
(45) Date of Patent: *Feb. 8, 2011

(54) ABSORBENT ARTICLE

(75) Inventors: Hiroyuki Hanao, Shikokuchuo (JP); Taira Kubo, Shikokuchuo (JP); Yoshiharu Miyashita, Shikokuchuo (JP); Tomotsugu Matsui, Shikokuchuo (JP); Akinori Fukae, Shikokuchuo (JP); Toshikazu Maeda, Shikokuchuo (JP); Hiroyuki Yano, Shikokuchuo (JP); Takeshi Furudoi, Shikokuchuo (JP)

(73) Assignee: Daio Paper Corporation, Ehime (JP)

( * ) Notice: Subject to any disclaimer, the term of this patent is extended or adjusted under 35 U.S.C. 154(b) by 192 days.

This patent is subject to a terminal disclaimer.

(21) Appl. No.: 11/630,913

(22) PCT Filed: Jun. 28, 2005

(86) PCT No.: PCT/JP2005/011862

§ 371 (c)(1),
(2), (4) Date: Sep. 7, 2007

(87) PCT Pub. No.: WO2006/001457

PCT Pub. Date: Jan. 5, 2006

(65) Prior Publication Data

US 2008/0044616 A1 Feb. 21, 2008

(30) Foreign Application Priority Data

| Jun. 28, 2004 | (JP) | 2004-190410 |
| Jun. 30, 2004 | (JP) | 2004-194851 |
| Jun. 30, 2004 | (JP) | 2004-194852 |
| Jun. 30, 2004 | (JP) | 2004-194854 |
| Nov. 25, 2004 | (JP) | 2004-340951 |
| Nov. 29, 2004 | (JP) | 2004-344715 |
| Feb. 8, 2005 | (JP) | 2005-031662 |
| Mar. 31, 2005 | (JP) | 2005-103856 |

(51) Int. Cl.
*A61F 13/15* (2006.01)

(52) U.S. Cl. .............. 604/358; 604/385.101; 442/417; 428/156

(58) Field of Classification Search .......... 442/417; 428/156; 604/375, 385.101, 385.19, 383
See application file for complete search history.

(56) References Cited

U.S. PATENT DOCUMENTS

| 6,646,180 | B1 | 11/2003 | Chmielewski |
| 6,660,902 | B2 | 12/2003 | Widlund et al. |
| 2003/0212376 | A1* | 11/2003 | Walter et al. ............. 604/358 |
| 2004/0024375 | A1 | 2/2004 | Litvay |
| 2008/0038504 | A1* | 2/2008 | Manabe et al. ........... 428/71 |
| 2008/0262459 | A1* | 10/2008 | Kamoto et al. ........... 604/375 |
| 2009/0004435 | A1* | 1/2009 | Hanao et al. ............ 428/156 |
| 2009/0247977 | A1* | 10/2009 | Takeuchi et al. ......... 604/375 |

FOREIGN PATENT DOCUMENTS

| CN | 2258390 | 7/1997 |
| CN | 1342446 | 4/2002 |
| CN | 1372451 | 10/2002 |
| CN | 1507336 | 6/2004 |
| JP | H5-277147 | 10/1993 |
| JP | H11-081116 | 3/1999 |
| JP | 2000-015093 | 1/2000 |
| JP | 2000-333992 | 12/2000 |
| JP | 2001-214399 | 8/2001 |
| JP | 2001-231815 | 8/2001 |
| JP | 2001-524350 | 12/2001 |
| JP | 2002-509764 | 4/2002 |
| JP | 2002-177330 | 6/2002 |
| JP | 2002-282304 | 10/2002 |
| JP | 2002-291804 | 10/2002 |
| JP | 2003-33397 | 2/2003 |
| JP | 2003-033398 | 2/2003 |
| JP | 2003-70820 | 3/2003 |
| JP | 2003-088555 | 3/2003 |
| JP | 2003-190210 | 7/2003 |
| JP | 2003-192732 | 7/2003 |
| JP | 2004-41339 | 2/2004 |
| JP | 2004-065300 | 3/2004 |
| WO | WO 2004/017883 | 3/2004 |

* cited by examiner

*Primary Examiner*—Arti Singh-Pandey
(74) *Attorney, Agent, or Firm*—DLA Piper LLP (US)

(57) ABSTRACT

An absorbent article including a fiber aggregate formed by opening the tow, a super absorbent polymer particle, and a sheet covering these components. The super absorbent polymer particle are bonded to the sheet with an adhesive that is applied in a continuous plane to the entire surface or the substantially entire surface at least at the portion to be provided with the super absorbent polymer particle in this sheet.

4 Claims, 50 Drawing Sheets

ABSORBENT ARTICLE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to absorbent articles such as paper diapers or sanitary napkins, absorbent bodies for use in absorbent articles.

2. Prior Art

Conventionally, as an absorbent body for use in a body fluid absorbent article, there has been generally used one where super absorbent polymer particles are dispersed and held in an airformed core of pulp short fibers (for example, refer to Patent Document 1). In such an absorbent body according to the conventional absorbent body, in order to meet requirements for light saving and thinning, at present, there is no way but to reduce the amount of fibers in the absorbent body.

However, when the use amount of pulp is reduced, the bulk of the absorbent body decreases conspicuously, and the absorbent body loses body, and accordingly, its sense of use is deteriorated, and its absorption performance declines and leakage occurs, and other troubles occur. Accordingly, there are limitations in making the conventional absorbent body light saving or thinning, and fundamental improvements are desired. (see Japanese Unexamined Patent Application Publication No. 2004-65300)

BRIEF SUMMARY OF THE INVENTION

Accordingly, the main object of the present invention is to make an absorbent body light saving or thinning, without deteriorating its sense of use and absorption performance.

In order to achieve the above object, according to one aspect of the present invention, there are provided the following absorbent bodies and absorbent articles including:

a fiber aggregate and super absorbent polymer, wherein
as the fiber aggregate, a tow composed of fibers is used, and
as the super absorbent polymer, polymer whose amount of water absorption is 50 g/g or higher is used.

The present invention is characterized by that the fiber aggregate made of a tow (fiber bundle) composed of fibers, and the super absorbent polymer having a high amount of water absorption are used in combination. That is, in the present invention, the fiber aggregate made of a tow is used, thereby it is possible to reduce the use amount of fibers while preventing the decrease of the bulk, body, and absorption performance, and make the absorbent body light saving or thinning, and further, the super absorbent polymer whose amount of water absorption is higher than that of normally employed polymer is daringly employed, thereby it is possible to make up for unavoidable decline of the absorption performance. Meanwhile, the amount of water absorption is described later herein.

In another aspect of the present invention, as the super absorbent polymer, a polymer whose speed of water absorption is 45 seconds or below is used.

In the case where the speed of water absorption exceeds 45 seconds, there often occurs so-called a backward leakage where body fluid supplied to the absorbent body leaks out of the absorbent body, therefore, it is preferable that the speed of water absorption is 45 seconds or below. Meanwhile, the speed of water absorption is described later herein.

In a third aspect of the present invention, as the super absorbent polymer, a polymer whose gel strength is 900 Pa or higher is used.

In the case where a bulky absorbent body is made by use of a tow, the amount of the super absorbent polymer existing out of the fiber aggregate inevitably increases. But, when this super absorbent polymer absorbs body fluid, it causes the sense of surface tackiness. Therefore, in order to control this sense of surface tackiness, in the invention in the claim, the gel strength is 900 Pa or higher, which is higher than the conventionally used one in general. Meanwhile, the gel strength is described later herein.

In a fourth aspect of the present invention, the basis weight of the super absorbent polymer is 400 g/m$^2$ or below.

The basis weight of the super absorbent polymer is made to be 400 g/m$^2$ or below, and accordingly, it is possible to prevent the light saving effect from being hardly made by the adoption of the fiber aggregate made of a tow, by the weight of the super absorbent polymer.

In a fifth aspect of the present invention, as the super absorbent polymer, a polymer whose fiber density is 0.0075 g/cm$^3$ or below when the thickness thereof is 10 mm is used.

When the fiber density increases to excess, it is difficult to make even a fiber aggregate made of a tow light saving or thinning. Accordingly, it is preferable to use the fiber aggregate having the fiber density of the range specified in the claim.

In a sixth aspect of the present invention, the basis weight of the fiber aggregate is 0.0075 g/cm$^3$ or below.

When the mass per unit are of a fiber increases to excess, it is difficult to make even a fiber aggregate made of a tow light saving. Accordingly, it is preferable to use the fiber aggregate having the basis weight of a fiber of the range specified in the claim.

In a seventh aspect of the present invention, the plane projection area thereof is 400 c/m$^2$ or higher, and the thickness thereof is 1 cm or below.

In the present invention, when the size of the absorbent body is in the range specified, it becomes easy to make the absorbent body light saving or thinning, without deteriorating the absorption performance thereof.

In an eighth aspect of the present invention, the weight thereof is 15 g or below.

Even when the weight exceeds 15 g, there is the effect of using the fiber aggregate made of a tow itself, and the absorption performance increases with a same weight. However, when this weight is attained, the influence of the weight of the fiber aggregate upon the weight of the absorbent body becomes small, and the effect of using the fiber aggregate made of a tow becomes scarce. Accordingly, if attention is put on the viewpoint of light saving, it is preferable that the weight of the absorbent body is 15 g or below.

In a ninth aspect of the present invention, an absorbent article equipped with the absorbent body according to one of the previous aspects is provided.

The absorbent article is equipped with the absorbent body, therefore it is possible to obtain the absorbent article having the characteristics of the absorbent body.

In a tenth aspect of the present invention, a holding sheet is arranged on the back surface side of the absorbent body.

In the case where super absorbent polymer particles are included in the fiber aggregate formed by opening a tow, when the back surface of the product is touched, concaves and convexes dropping out from the fiber aggregate or of SAP particles at the bottom of the fiber aggregate cause shuffling discomfort, declining the value of the product. Meanwhile, when the holding sheet is arranged according to the present invention, it is possible to ease or eliminate the shuffling discomfort when the back surface of the product is touched.

As described above, according to the present inventions, the above-mentioned each advantage is achieved.

DETAILED DESCRIPTION OF THE INVENTION

Hereinafter, one preferred embodiment according to the present invention is described in detail referring to paper diapers as well as manufacturing facilities thereof shown in attached drawings.

Figure 1:
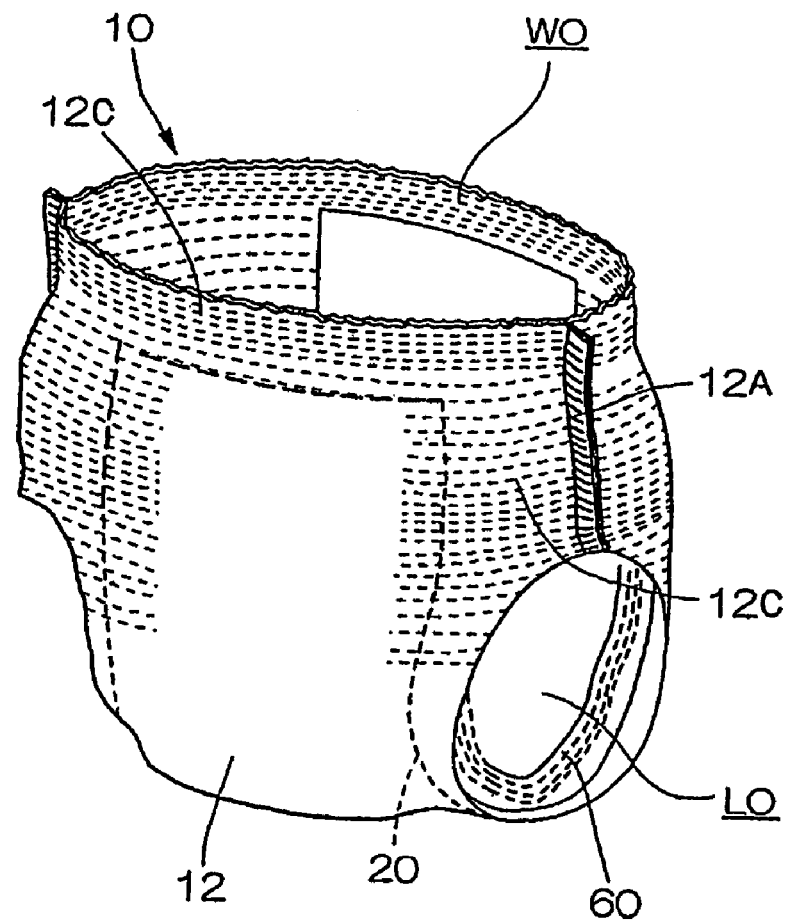
FIG. 1 is a perspective view showing a pant-type diaper.

FIG. 1 shows an example of pant-type disposable diapers. This pant-type disposable diaper 10 is provided with an exterior sheet 12 on the outside (backside) and an absorbent body 20 on the inside (front side). The absorbent body 20 is fixed to the exterior sheet 12. The absorbent body 20 is a part of receiving body fluids such as urines or soft stools (menstrual blood in the case of sanitary napkins as described below). The exterior sheet 12 is a portion with which a user wears the pant-type disposable diaper.

The exterior sheet 12 is hourglass-shaped as shown, and is narrow at the intermediate portion, to be regions on both sides through which a user puts his legs. Although the absorbent body 20 may have any shape, it is rectangular in the illustrated embodiment.

Figure 2:
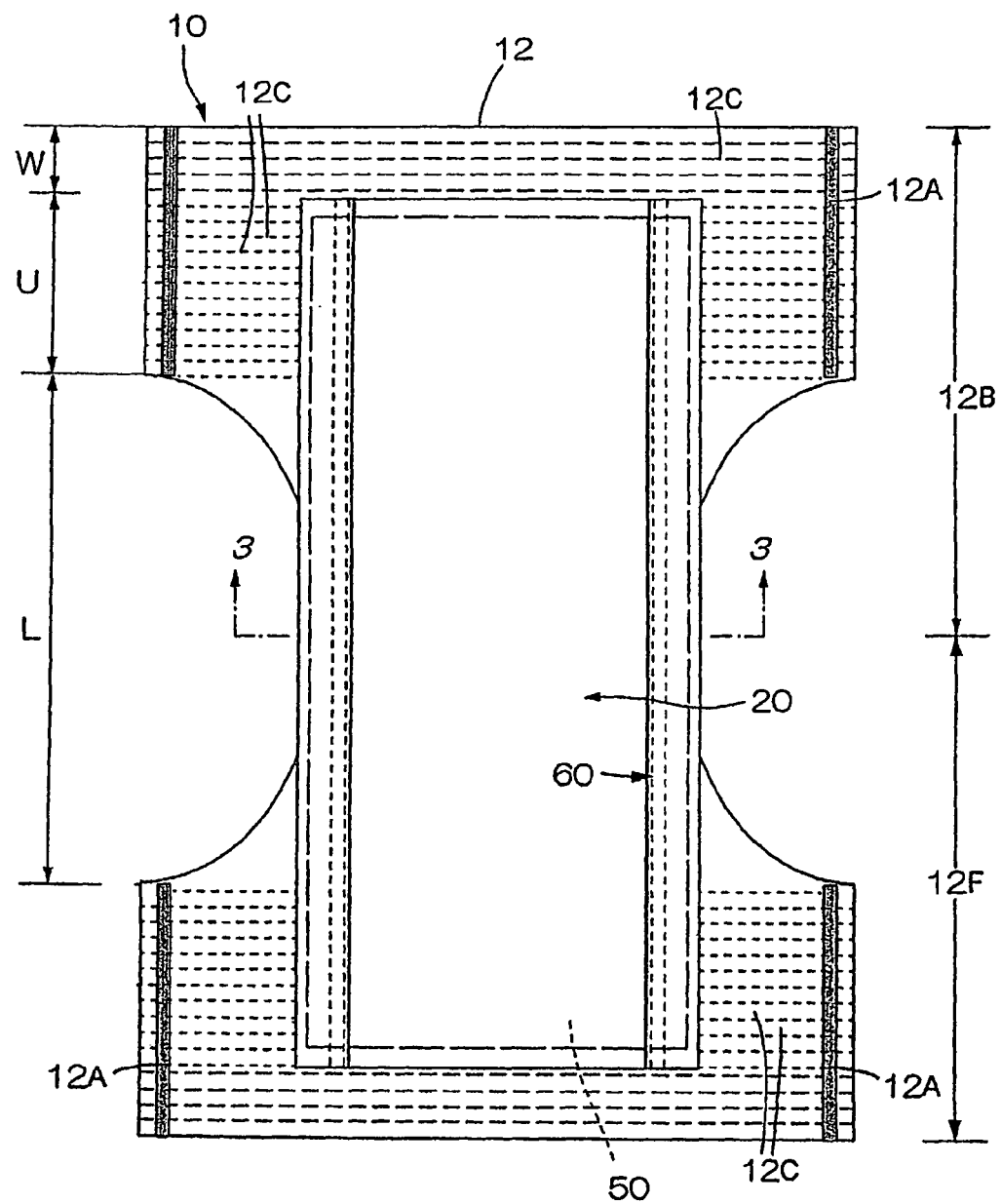
FIG. 2 is a plan view showing a pant-type diaper in a deployed state.

In the exterior sheet 12, as shown in FIG. 2, the absorbent body 20 is mounted and fixed in a predetermined position and thereafter folded in front and back, and a front body 12F and a back body 12B of the exterior sheet 12 are joined by heat sealing at junction regions 12A on both sides. Whereby, a pant-type disposable diaper including a waist opening WO and a pair of leg openings LO in structure shown in FIG. 1 is obtained.

There is shown the embodiment in which the width at the intermediate portion in a longitudinal direction (that is, in a vertical direction of FIG. 2. It is a front-back direction of a product as well) of an absorbent body 20 is smaller than the width at the narrow portion of the exterior sheet 12. The relation between these widths is vice versa, or the widths may be the same.

An exterior sheet 12 is desirably an embodiment that is made of, for example, two water-repellent non-woven cloth sheets, and provided with elastic stretching members interposed between these sheets to be fit to a user by elastic constrictive forces thereof. As this elastic stretching member, although a rubber thread or a strip of elastic foam, multiple rubber threads are desired to use. In the illustrated embodiment, rubber threads 12C, 12C . . . are continuously provided in the width direction in the waist region W, and provided only at both side portions in the sub-lumber region U, and are not provided in the crotch region L. Due to that the rubber threads 12C, 12C . . . are provided at both the waist region W and the sub-lumber region U, even if elastic constrictive forces of rubber threads 12C themselves are small, a paper diaper is in contact with a user also in the sub-lumber region U in its entirety. Thus, a product will be preferably fit to a user.

Figure 3:
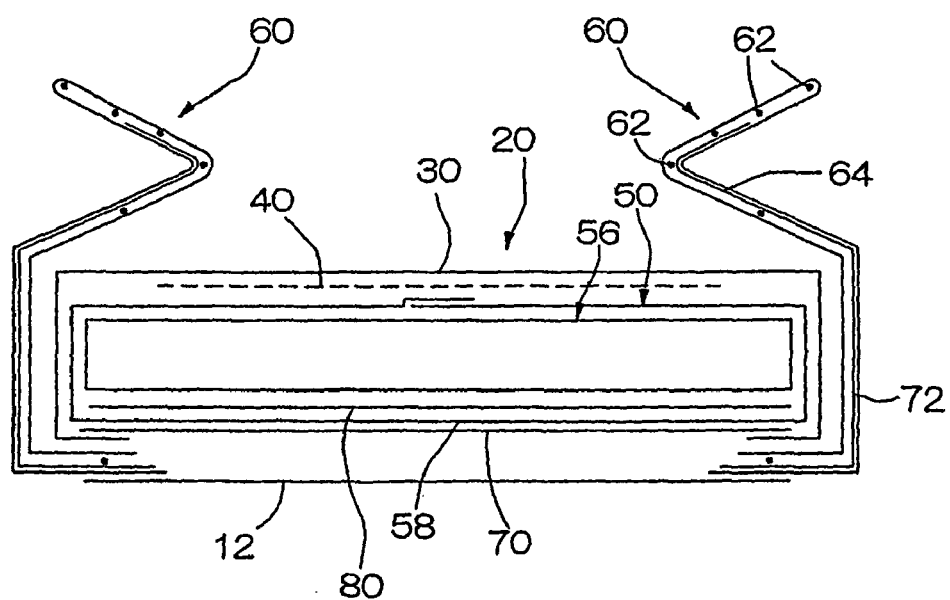
FIG. 3 is a plan view showing a pant-type diaper in a deployed state.

An absorbent body 20 according to the embodiment, as shown in FIG. 3, is provided with a top sheet 30 made of, for example, non-woven cloths allowing body fluids to permeate, an intermediate sheet (second sheet) 40, and an absorbent body 50 containing an absorbent core 56. Further, there is provided on the backside of the absorbent body 50 a body-fluid impermeable sheet (it is referred to as back sheet) 70 made of e.g., a plastic sheet. There is an exterior sheet 12 on the backside of this body-fluid impermeable sheet 70. Furthermore, there are provided barrier cuffs 60, 60 on both sides.

The top sheet 30 possesses properties of allowing body fluids to permeate. Thus, as materials of the top sheet 30, what exhibits this body-fluid permeability will suffice, and, for example, porous or non-porous non-woven cloths, or porous plastic sheets may be exemplified. Moreover, non-woven cloths out of these materials are not particularly limited in material fibers thereof. Examples of these non-woven cloths include olefin-based synthetic fibers such as polyethylene or polypropylene, polyester-based synthetic fibers, or polyamide-based synthetic fibers; regenerated fibers such as rayon or cupra; natural fibers such as cottons; or fiber blend using these fibers in combination. Further, non-woven cloths may be manufactured by any processing. Examples of processing methods include known methods of spun lace, spun bond, thermal bond and melt blown processes, and by needle punching. In case of requiring flexibility or drapability, span lace process is preferred. In case of requiring high bulking power or softness, thermal bond process is preferred.

Furthermore, a top sheet 30 may be formed of one sheet, or a laminated sheet obtained by not less than two sheets being bonded. Likewise, the top sheet 30 may be formed of one sheet or not less than two sheets in a planer direction.

To cause body fluids having been permeated to transmit to an absorbent body, it may be provided an intermediate sheet 40 normally referred to as "second sheet" having a higher transmission rate than that of the top sheet 30. This intermediate sheet not only allows body fluids to immediately transmit to the absorbent body to enhance an absorption performance, but also prevents "reversing" phenomenon of absorbed body fluids from the absorbent body, thus enabling to make the top sheet 30 in a dry state all the time.

Figure 20:
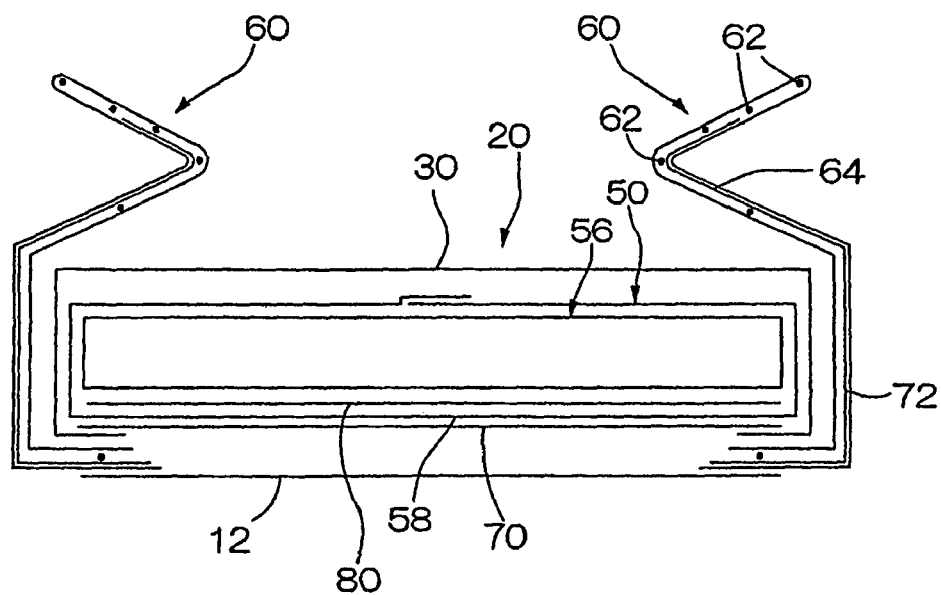
FIG. 20 is a sectional view showing another embodiment of an absorbent body.

An intermediate sheet (second sheet) 40 is interposed between a top sheet 30 and a covering sheet 58. As shown in FIG. 20, an embodiment with no intermediate sheet (second sheet) 40 can be employed.

An intermediate sheet 40 according to an illustrated embodiment is located centrally shorter than the width of an absorbent core 56, but it may be provided across its entire width. The longitudinal length of the intermediate sheet 40 may be the same as the length of the absorbent core 56, or may within a shorter length range with the region for receiving body fluids centered. A typical material of the intermediate sheet 40 is non-woven cloth of a superior permeability of body fluids.

Examples of materials of an intermediate sheet 40 may include the same material as a top sheet 30, spun lace, pulp non-woven cloth, mixed sheets of pulp and rayon, point bond or crepe papers. In particular, air-through non-woven cloth and spun-bond non-woven cloth are preferred.

The elasticity in front-back direction of products of an intermediate sheet is preferably 0.05 to 0.75 g·cm$^2$/cm in order to reduce or eliminate the occurrence of shuffling discomfort in the case of touched from the front side of a product. Herein, "elasticity in front-back direction of a product" means the one obtained as values in the case where a sample cut in length of 200 mm and width of 20 mm is folded in the range of DFE sensitivity 20, curvature 0.0 cm$^{-1}$ to 0.5 cm$^{-1}$ using a pure bending tester ("KES-FB2" manufactured by Kato Tech Co., Ltd.). A covering sheet is also likewise.

An absorbent body 50 includes an absorbent core 56 having a fiber aggregate opened tows and super absorbent polymer particles, and a covering sheet 58 covering at least the backside and sides of this absorbent core 56. Furthermore, there is provided a holding sheet 80 between the absorbent core 56 and the backside site (lower portion) of the covering sheet 58.

Figure 4:
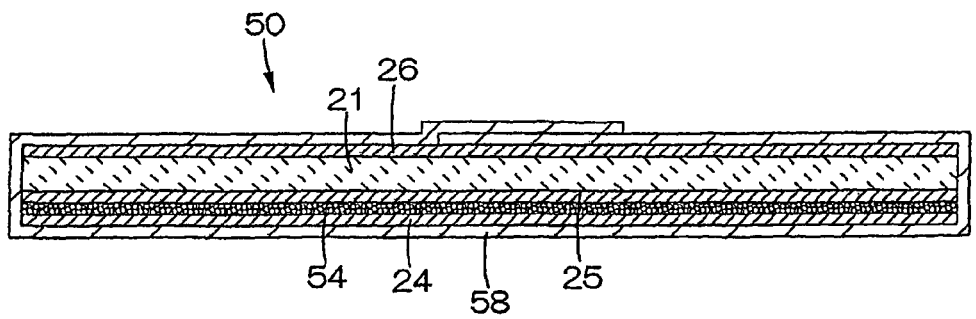
FIG. 4 is a sectional view showing a first preferred embodiment of an absorbent body.

FIG. 4 shows a first preferred embodiment of an absorbent body. This absorbent body 50 includes an absorbent core 56 having a fiber aggregate 21 and super absorbent polymer particles 54, and a covering sheet 58 covering at least the backside and sides of this absorbent core 56. The covering sheet 58 is applied with an adhesive 24 in a continuous plane at least on the entire surface or the substantially entire surface where super absorbent polymer particles are provided. Incidentally, "substantially entire surface" is referred to as 80% of the portions where super absorbent polymer particles are provided.

In further detail, a layer formed of super absorbent polymer particles 22 is provided via the adhesive 24 on the inside of the covering sheet 58, a layer formed of the fiber aggregate 21 is provided on the top thereof via the adhesive 25, and further the covering sheet 58 is bonded via the adhesive on the top of the fiber aggregate 21. The covering sheet 58 of the illustrated example is constructed to cover the fiber aggregate 21 and the super absorbent polymer particles 54 by being folded at both sides, but may employ an embodiment in which they are sandwiched between two vertical sheets to be packaged. As this covering sheet 58, as described below, preferably absorbent sheets such as crepe papers or non-woven cloths are used.

In addition, although not shown, there are provided on the entire surface or the substantially entire surface at least of the portion where super absorbent polymer particles are provided at a covering sheet 58 the portion to which an adhesive is applied, and a plurality of portions at which there is no adhesive surrounded by the portion applied with the adhesive. Thus, it may be constructed to include super absorbent polymer particles bonded with respect to the covering sheet 58 at the portion applied with the adhesive and super absorbent polymer particles resided at the portion with no adhesive.

In the case of applying an adhesive 24 in a continuous plane, curtain coating or roll coating may be used. In the case where there are provided the portion applied with an adhesive and a plurality of portions with no adhesive surrounded by the portions applied with the adhesive, spiral coating may be employed. As an adhesive 24, thermoplastic resins capable of being used in binders of the below-described fiber aggregate are preferably used. Further, it is preferable that part or whole of the super absorbent polymer particles 54 are adhered and fixed to the fiber aggregate 1 with adhesive 5.

In the present first example of an absorbent body, most super absorbent polymer particles 54 are bonded with respect to a covering sheet 58 with an adhesive 24, or a part of super absorbent polymer particles 54 are bonded with respect to the covering sheet 58 with the adhesive 24, as well as most super absorbent polymer particles 54 are contained in a closed space with no adhesive surrounded by the portions applied with the adhesive. Furthermore, a part or the whole of super absorbent polymer particles 54 are bonded with an adhesive 25 to the fiber aggregate 21. Thus, shuffling hand feeling and unwanted non-uniform absorbent characteristics can be effectively prevented. Moreover, a reference numeral 26 designates an adhesive for bonding the face opposite to the polymer side of the fiber aggregate 21 and the covering sheet 58 together.

Figure 5:
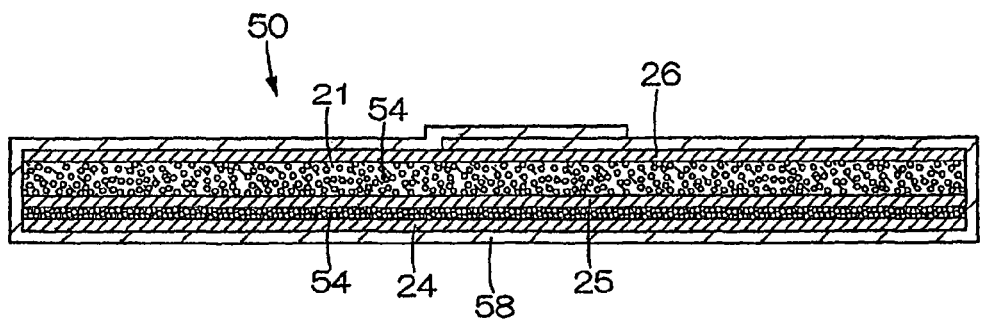
FIG. 5 is a sectional view showing a second preferred embodiment of an absorbent body.

FIG. 5 shows a second embodiment of an absorbent body, and differs at a point of allowing super absorbent polymers 54 to be held also in a fiber aggregate 21 to the first embodiment.

Figure 6:
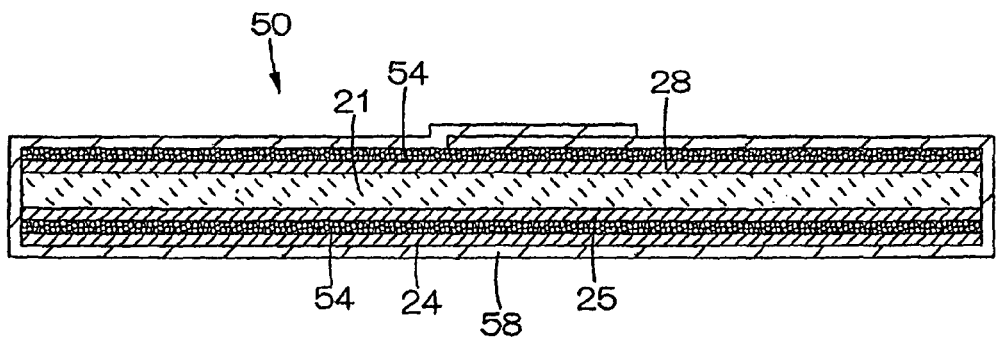
FIG. 6 is a sectional view showing a third preferred embodiment of an absorbent body.

FIG. 6 shows a third embodiment of an absorbent body, and differs at a point that there are provided on both vertical sides of a fiber aggregate 21 respective super absorbent polymers 54 with respect to the first embodiment in which there is provided on one side (lower side) of the fiber aggregate 21 the super absorbent polymers 54. In this case, the super absorbent polymers 54 positioned on the upper side of the fiber aggregate 21 can be bonded using an adhesive 28 with respect to the fiber aggregate 21.

Figure 7:
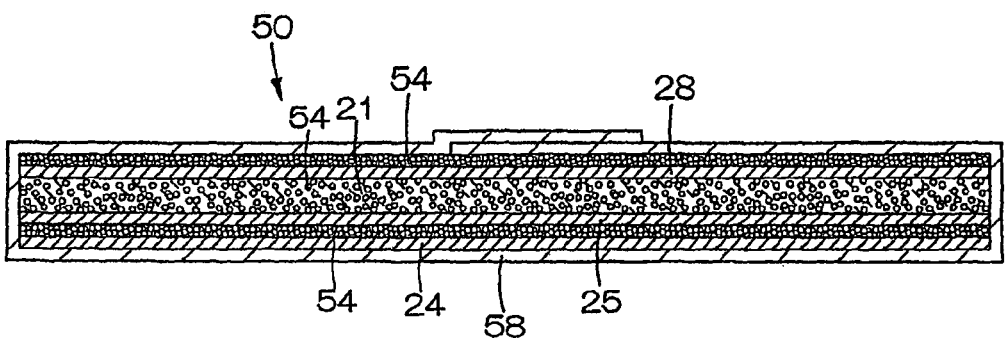
FIG. 7 is a sectional view showing a fourth preferred embodiment of an absorbent body.

FIG. 7 shows a fourth embodiment of an absorbent body, and is the one in which super absorbent polymers 54 are held also in a fiber aggregate 21 as is the second embodiment in the third embodiment.

Figure 8:
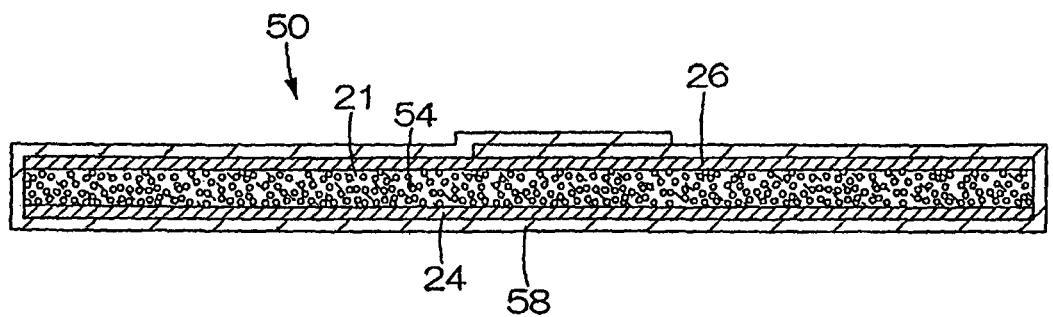
FIG. 8 is a sectional view showing a fifth preferred embodiment of an absorbent body.

FIG. 8 shows a fifth embodiment of an absorbent body, and is an embodiment in which super absorbent polymers 54 bonded to a covering sheet 58 in the second embodiment, and an adhesive 25 for bonding thereof are omitted, and super absorbent polymers 54 are held only in a fiber aggregate 21.

Figure 9:
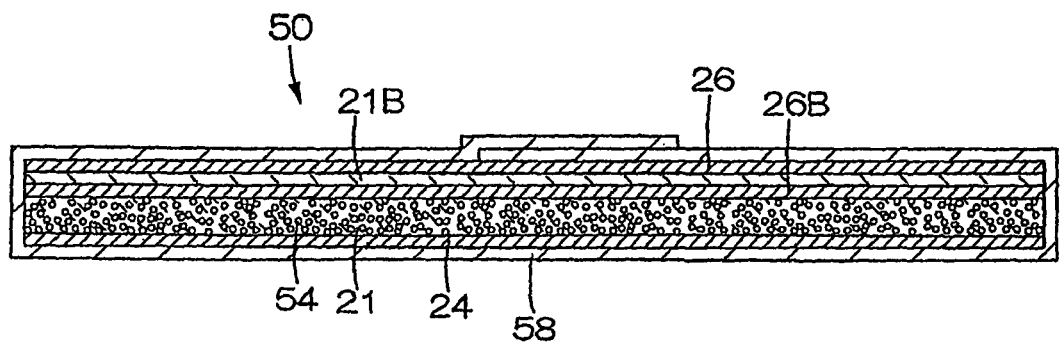
FIG. 9 is a sectional view showing a sixth preferred embodiment of an absorbent body.

FIG. 9 shows a sixth embodiment of an absorbent body, in which there is additionally provided a layer 21B solely of a fiber aggregate (with no super absorbent polymer 54) on a fiber aggregate 21 holding super absorbent polymers 54, as well as in which the fiber aggregate 21 that holds the super absorbent polymer 54 and the layer 21B solely with a fiber aggregate are bonded together with an adhesive 26B.

Figure 10:
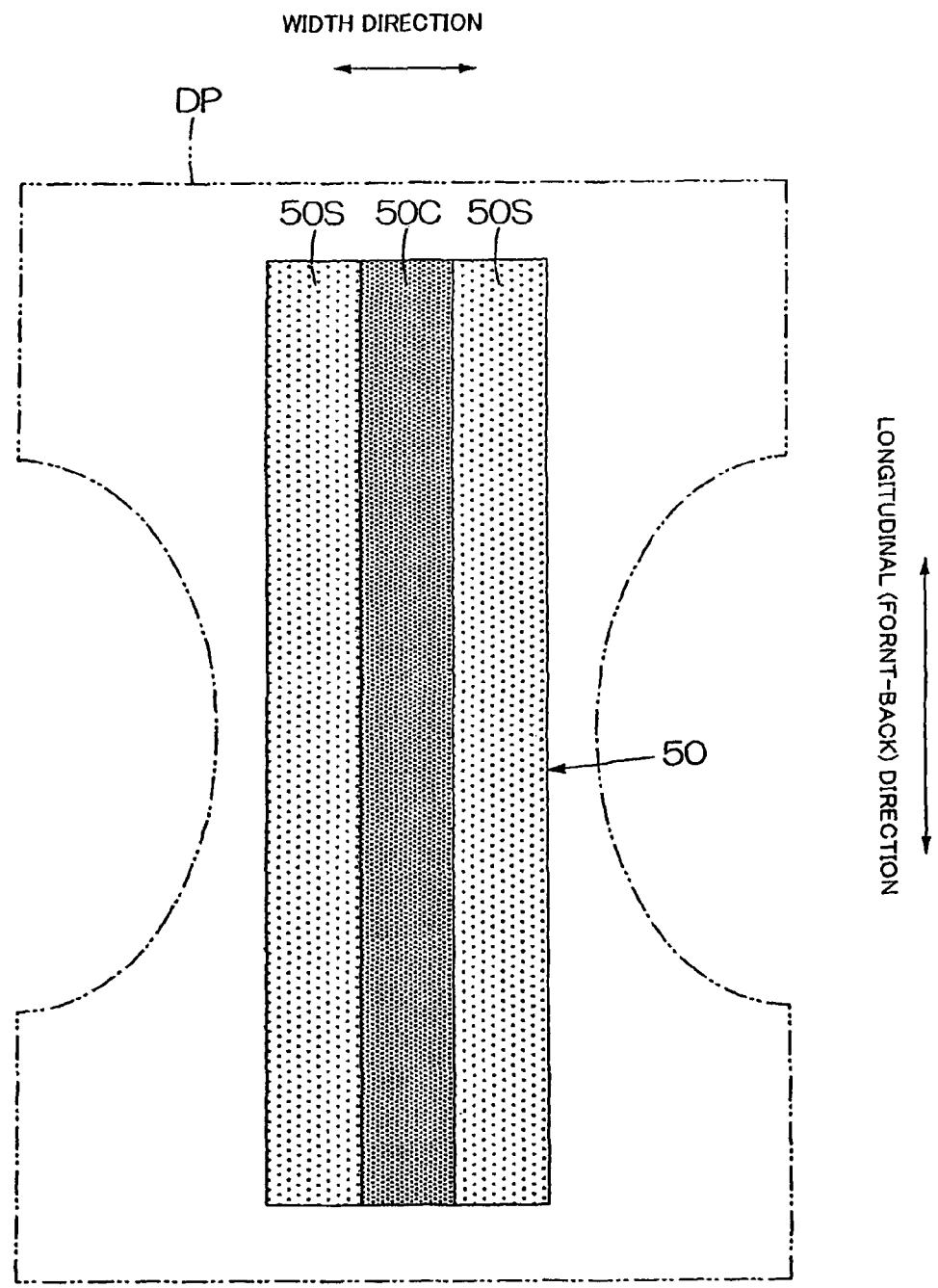
FIG. 10 is a plan view showing a seventh preferred embodiment of an absorbent body.
Figure 11:
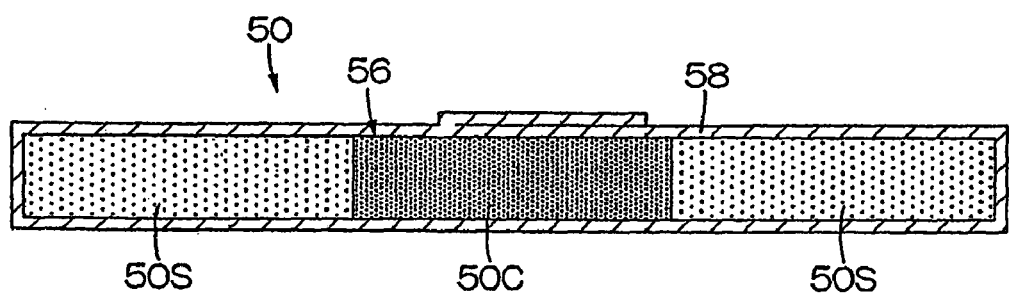
FIG. 11 is a sectional view showing the seventh embodiment of an absorbent body.

FIGS. 10 and 11 show a sixth embodiment of an absorbent body 50. This absorbent body 50 includes an absorbent core 56 having a fiber aggregate formed of tows made of fibers, and super absorbent polymer particles, and a covering sheet 58 covering these components, and is characterized in that there are provided the portion of a relatively large amount of super absorbent polymer particles and the portion of small amount thereof. These more or less amounts are shown with shades of dots. Owing to such construction, it is possible to achieve intended non-uniform absorption characteristics, particularly the amounts of absorption.

particularly as the illustrated example, it is a preferred embodiment that the amount of super absorbent polymer particles at a width directional intermediate part 50C of a fiber aggregate is larger than the amount of super absorbent polymer particles at both longitudinal side parts 50S of the fiber aggregate. In this case, when it is used in alignment with a width direction of an absorbent article (paper diaper DP in an the illustrated example), a larger amount of absorption at the intermediate part 50C in a width direction to which more body fluids are fed can be assured.

Figure 12:
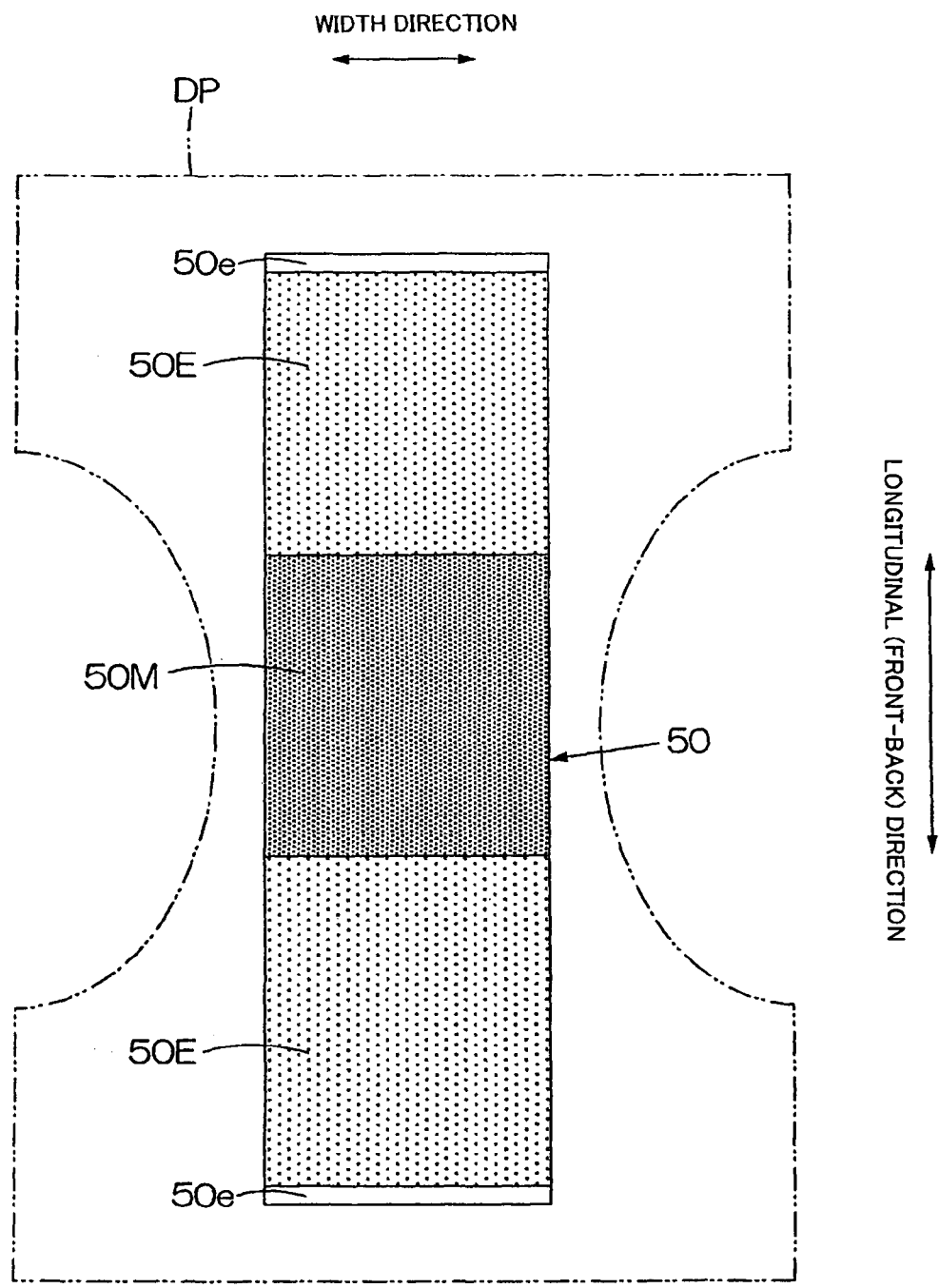
FIG. 12 is a plan view showing the seventh embodiment of an absorbent body.

Furthermore, as shown in FIG. 12, it is a preferred embodiment that the amount of super absorbent polymer particles at a longitudinal intermediate part 50M of a fiber aggregate is made larger than the amount of super absorbent polymer particles at a longitudinal front-back parts 50E of a fiber aggregate. In this case, when it is used in alignment with a longitudinal direction of an absorbent article (paper diaper DP in an illustrated example), a larger amount of absorption at the longitudinal intermediate part 50M to which more body fluids are fed can be assured.

In addition, it is a preferred embodiment that there is no super absorbent polymer particles at cut sites 50e at both longitudinal ends. When manufacturing, it is possible to prevent a shorter product life of cutter blades. An absorbent body according to such embodiment can be manufactured by setting application amounts of super absorbent polymer particles to be at three levels (much, less, and no), and repeating cycles consisting of much, less, and no.

On the other hand, in some cases, the amount of super absorbent polymer particles at both longitudinal end parts 50E, 50E may be made larger than the amount of super absorbent polymer particles at the longitudinal intermediate part 50M. Moreover, although in the illustrated example, an absorbent body 50 is longitudinally divided into three sections of an intermediate part and both end parts, it may be divided into two or not less than four sections to have different amounts of super absorbent polymer particles in respective sections, or the absorbent body 50 have amounts of super absorbent polymer particles continuously changed in a longitudinal direction.

In an absorbent body 50, super absorbent polymer particles may be held in a fiber aggregate or held on the fiber aggregate surface, or may be held in both. Furthermore, super absorbent polymer particles may be held partly on the fiber aggregate surface, and may be held in its entirety of the fiber aggregate.

Figure 13:
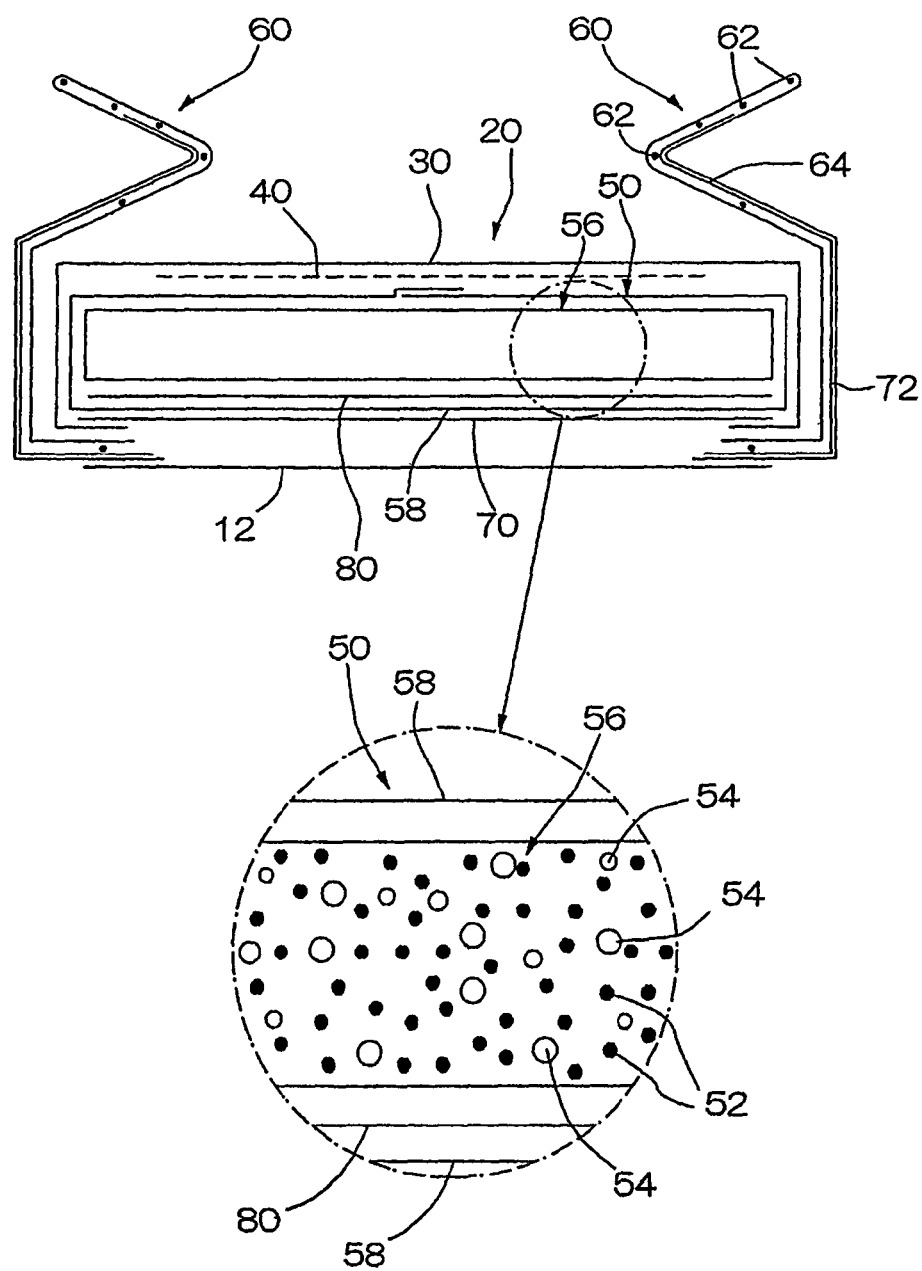
FIG. 13 is a sectional view showing the seventh embodiment of an absorbent body.

However, at least in the region of receiving body fluids, preferably super absorbent polymer particles (SAP particles) are dispersed substantially across the thickness with respect to a fiber aggregate. This state in which the super absorbent polymer particles are dispersed substantially across the thickness is conceptually shown as an enlarged view of a principal part of FIG. 13. Furthermore, reference numeral 52 in FIG. 13 designates a component fiber (filament) of a fiber aggregate.

Figure 14:
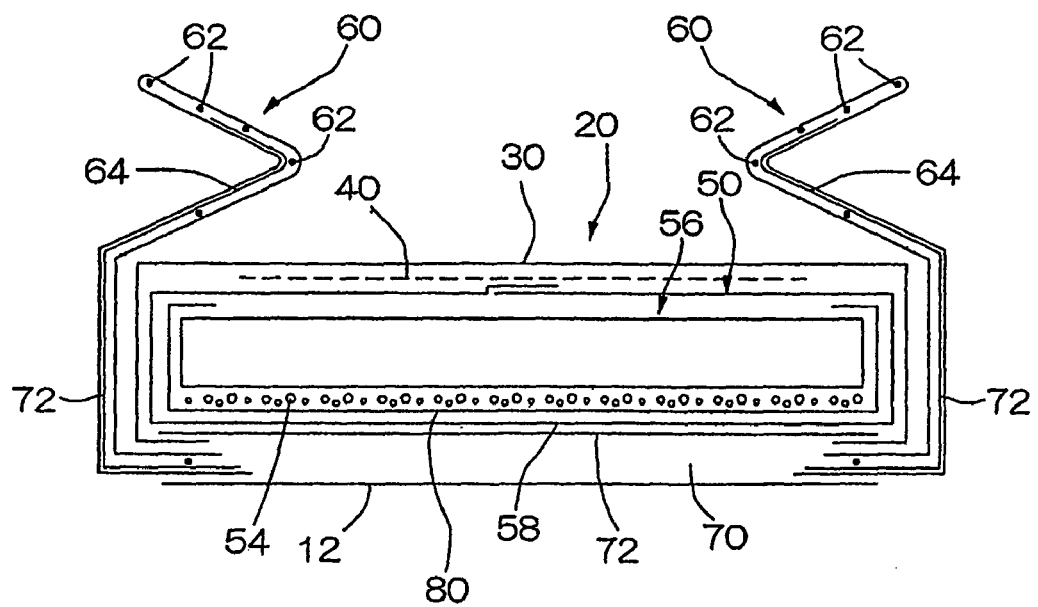
FIG. 14 is a sectional view showing the seventh embodiment of an absorbent body.

In case where there are no SAP particles at the upper, lower and intermediate portions of an absorbent core 56, it cannot be said to be "dispersed across the thickness." Therefore, embodiments of "dispersed across the thickness" include an embodiment in which SAP particles are dispersed "uniformly" across the thickness with respect to the fiber aggregate, and additionally an embodiment in which although they are "localized" at the upper, lower and intermediate portions, they are still dispersed in respective upper, lower and intermediates portions. In addition, an embodiment in which a part of SAP particles are not entered in a fiber aggregate, but remained on the surface thereof, an embodiment in which a part of SAP particles are passed through the fiber aggregate to be resided on a covering sheet 58, or an embodiment in which they are resided on a holding sheet 80 as shown in FIG. 14 are not to be excluded. Further, in the case of not considering gel blocking, SAP particles may be localized only at the upper or intermediate portions. In the case of considering no reversing, they may be localized only at the intermediate and lower portions.

Although in the seventh embodiment, there are larger or smaller amounts of super absorbent polymer particles at each part (hereinafter, referred to as dispersion density) in respect of at least one direction of a width direction, a longitudinal direction and a thickness direction of products, alternatively an embodiment in which amounts of super absorbent polymer particles are uniform in respect of all directions of a width direction, a longitudinal direction and a thickness direction of products may be employed.

Figure 15:
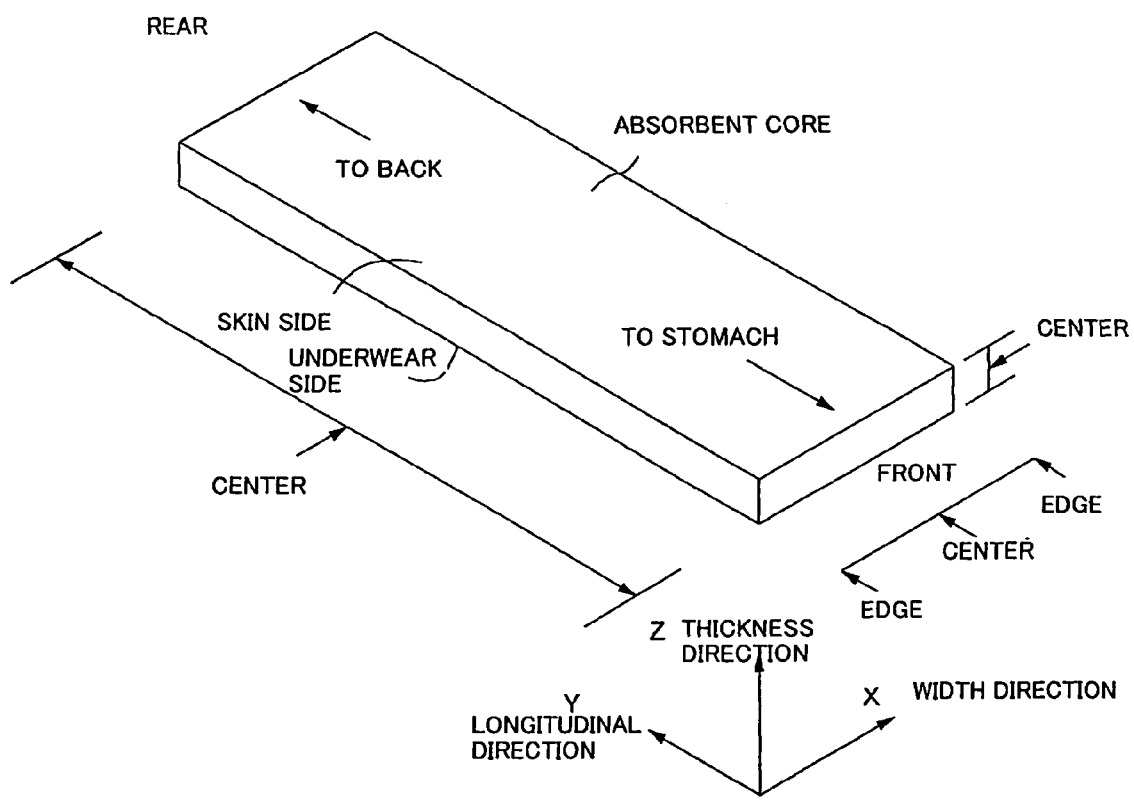
FIG. 15 is a schematic view for explaining directions of an absorbent body.

Embodiments "of super absorbent polymer particles of different magnitudes of dispersion densities" are shown as follows. Now, as shown in FIG. 15, in an absorbent core 56, when letting a width direction of a product X, a longitudinal direction Y, and a thickness direction Z, as shown in Table 1, the case of making a dispersion density of respective super absorbent polymer particles larger (higher) than that in the other regions is defined as "gathering", and the case of the dispersion density of super absorbent polymer particles is the same is defined as "uniform", specific advantages of each embodiment will be as shown in Tables 2 to 4. It is a matter of course that respective conditions can be used in combination.

[Table 1]

[Table 2]

[Table 3]

[Table 4]

Figure 16:
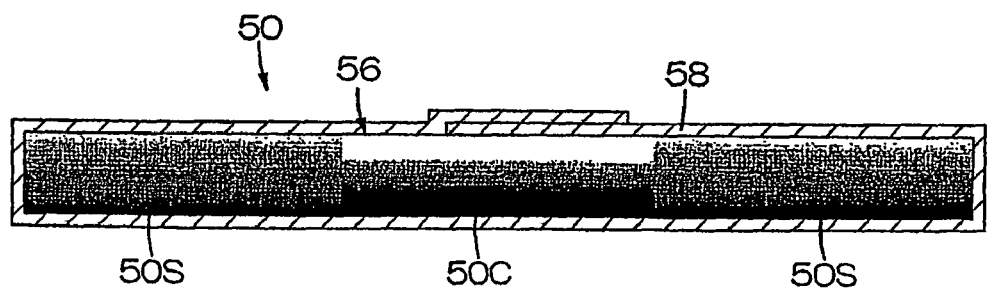
FIG. 16 is a sectional view showing an eighth preferred embodiment of an absorbent body.

Now, FIG. 16 shows an eighth embodiment of an absorbent body. This absorbent body 50 includes an absorbent core 56 containing a fiber aggregate and super absorbent polymer particles, and a covering sheet 58 covering these components, and is characterized in that there are provided the portion of a relatively high density of super absorbent polymer particles, and the portion of a relatively low density thereof. The higher or lower fiber densities are illustrated with gradation. In case where there are provided the portion of a relatively high density of super absorbent polymer particles and the portion of a relatively low density thereof in a fiber aggregate, it is possible to achieve intended non-uniform absorption characteristics, particularly the rates of absorption.

In particular, as in an illustrated example, it is a preferred embodiment that the density of super absorbent polymer particles at a width directional intermediate portion 50C is made higher than the density of super absorbent polymer particles at both width directional side portions 50S. In this case, achieved are such absorption characteristics as the absorption rate at the width directional intermediate portion 50C is low, and the absorption rate at both width directional side portions 50S is high. Thus, in the case of using this absorbent body in alignment with the width direction of an absorbent article, since much liquids are fed to the longitudinal intermediate portion at the width directional intermediated portion 50C, and spread around well therefrom, a wider area can be used for absorption. In addition, since the rate of absorption at both width directional side portions 50S is high, the so-called side leakage is prevented.

Figure 17:
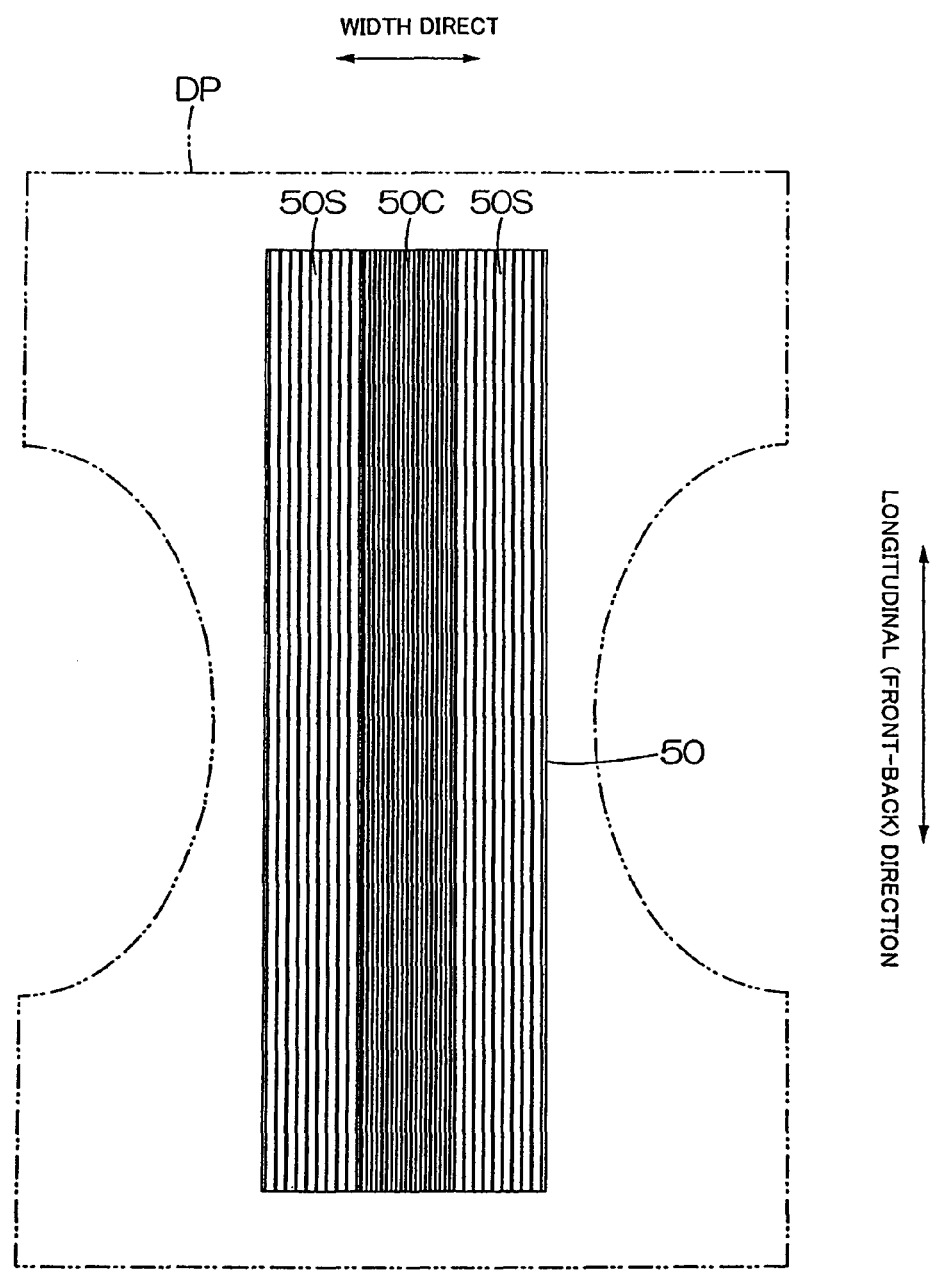
FIG. 17 is a sectional view showing a ninth preferred embodiment of an absorbent body.

Now, FIG. 17 shows a ninth embodiment of an absorbent body. This absorbent body 50 includes an absorbent core 56 containing a fiber aggregate and super absorbent polymer particles, and a covering sheet 58 covering these components, and is characterized in that there are provided the portion of a relatively high fiber density and the portion of a relatively low fiber density in the fiber aggregate. The magnitudes of these fiber densities are illustrated with the roughness and fineness of lines in the drawing. The fiber aggregate made of tows has characteristics of spreading liquids along a continuous direction of fibers, and this tendency comes to be marked as the density becomes higher. Thus, also by providing the portion of a relatively high fiber density and the portion of a relatively low fiber density in the fiber aggregate, it is possible to achieve intended non-uniform absorption characteristics of the absorbent body 50.

Such higher or lower fiber densities can be achieved by non-uniform opening such as partially strong opening at the time of manufacturing of a fiber aggregate, or by partially tying up a plurality of tows.

Particularly, as in the illustrated example, it is a preferred embodiment that the fiber density at a width directional intermediate parts 50C is made higher than the fiber density at both width directional side parts 50S. A fiber aggregate has such characteristics that the retention capacity of body fluids becomes higher in case of a lower fiber density, while spreading properties of body fluids becomes better in case of a higher fiber density. Therefore, when there are provided such different densities, body fluids are immediately spread at the width directional intermediate part 50C, and retention properties of body fluids are improved at both side parts 50S where no immediate spreading properties are required, thus to provide preferred characteristics to each site. More specifically, since spreading properties of body fluids at the width directional intermediate part 50C comes to be higher than spreading properties of body fluids at both width directional side parts 50S, in the case of using such absorbent body in alignment with the width direction of a body-fluid absorbent article, body fluids are likely to spread at the width directional intermediate part 50C where more liquids are fed, and thus a wider area can be used for absorption. In addition, since liquids are hard to spread at both width directional side portions 50S, the so-called side leakage is effectively prevented.

With no regard to how different fiber densities at both width directional side parts 50S and the width directional intermediate part 50C are, the fiber density at both side parts 50S is preferably 10 to 100 $g/m^3$, more preferably 20 to 70 $g/m^3$, most preferably 30 to 50 $g/m^3$. When the fiber density at both side parts 50S is too low, there is a risk of the occurrence of twisting in the width direction of a fiber aggregate. On the other hand, when the fiber density at both side parts is too high, there is a risk of providing discomfort to a user.

In the case of using an absorbent body 50 in an absorbent article, any side may be used as the side of receiving body fluids. In particular, in the first embodiment, it is preferred to use so that the fiber aggregate 21 side (upper side in the drawing) is the side of receiving body fluids.

Figure 18:
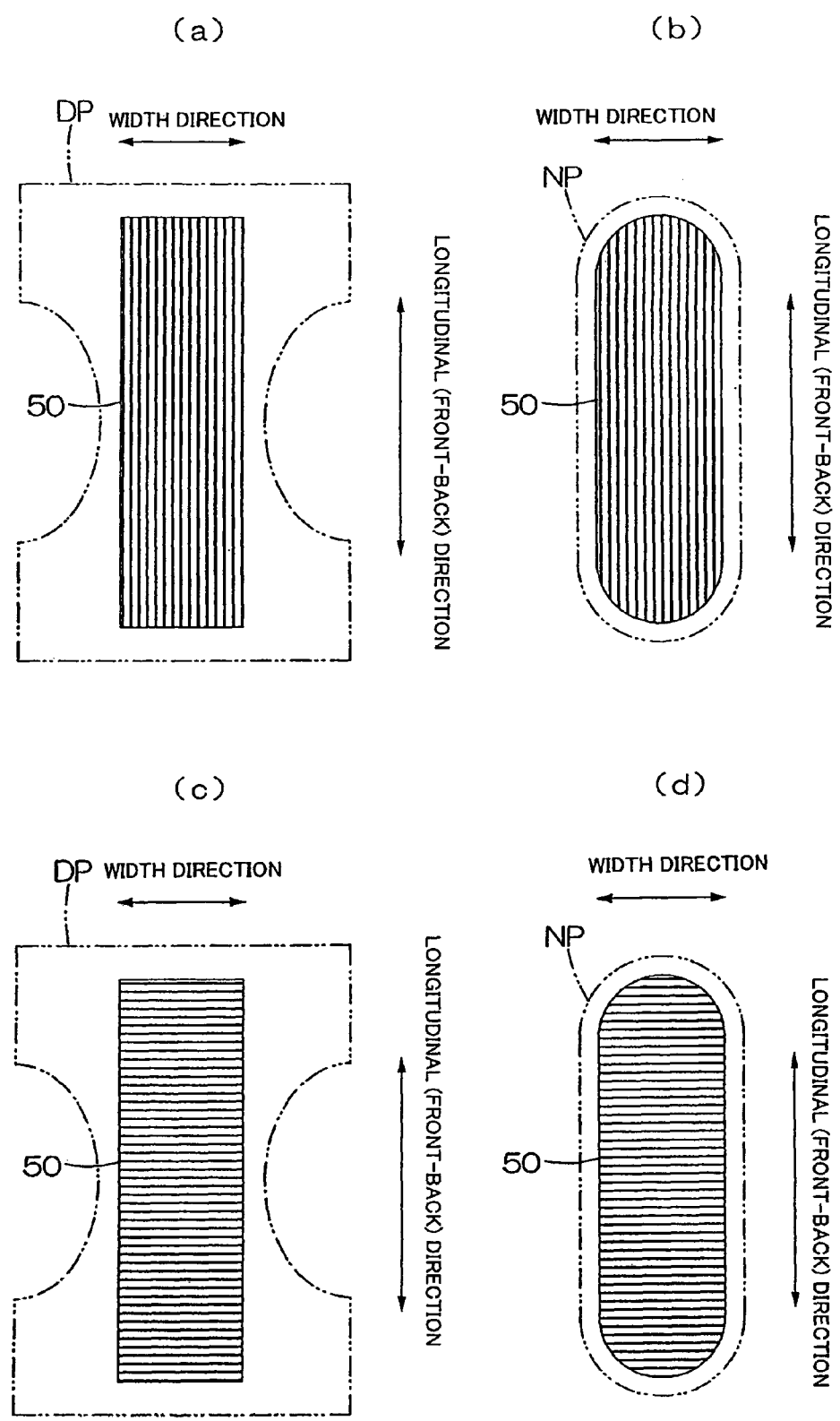
FIG. 18 is a plan view schematically showing the layout of an absorbent body.

Furthermore, FIG. 18 shows layout examples of an absorbent body in paper diapers DP or sanitary napkins NP. A fiber aggregate formed of opened tows have such characteristics that body fluids are likely to spread in a continuous direction (flow direction) of fibers, while body fluids are hard to spread in a direction orthogonal to the continuous direction of fibers. Therefore, an absorbent body 60, as shown in FIGS. 18 (a)(b), is preferably provided so that the continuous direction of fibers (illustrated with multiple lines) is aligned with the longitudinal direction (front-back direction) of articles. As shown in FIGS. 18 (c)(d), however, the absorbent body 60 may be provided so that the fiber continuous direction thereof is along the width direction of articles. When letting the continuous direction of fibers the longitudinal direction of articles, liquids will be immediately spread also in the longitudinal direction, and thus the entire surface of the absorbent body 50 will be effectively utilized.

A fiber aggregate is formed by the method of opening a tow (fiber bundle), being a bundle of filaments regarded substantially continuous fibers that is an aggregate of filaments. Examples of tow component fibers may include polysaccharides or its derivatives (cellulose, cellulose ester, chitin, chitosan, and the like), synthetic high polymers (polyethylene, polypropylene, polyamide, polyester, polylactam amide, polyvinyl acetate, and the like). In particular, cellulose ester and cellulose are preferred.

Examples of celluloses include plant body-derived cellulose such as cotton, linter, or wood pulp, or bacteria cellulose, and may include regenerated cellulose such as rayon. The regenerated cellulose may be spun fibers.

Examples of cellulose esters capable of being preferably employed may include organic acid esters such as cellulose acetate, cellulose butyrate, and cellulose propionate; mixed acid esters such as cellulose acetate propionate, cellulose acetate butyrate, cellulose acetate phthalate, and cellulose nitrate acetate; and cellulose ester derivatives such as polycaprolactone-grafted cellulose ester. These cellulose esters may be used alone or in combination. The viscosity-average degree of polymerization of cellulose esters is, for example, 50 to 900, preferably about 200 to 800. The average degree of substitution of cellulose esters is, for example, about 1.5 to 3.0 (e.g., 2 to 3).

The average degree of polymerization of cellulose esters may be, for example, about 10 to 1000, preferably about 50 to 900, more preferably about 200 to 800. The average degree of substitution of cellulose esters may be, for example, about 1 to 3, preferably about 1 to 2.15, more preferably about 1.1 to 2.0. The average degree of substitution of cellulose esters may be selected in respect of e.g., improved biodegradability.

Cellulose esters may be preferably organic acid esters (for example, esters with organic acids having about 2 to 4 carbons), most preferably cellulose acetate. The acetylation degree of cellulose acetate may be about 43% to 62% in many cases, but may be preferably about 30% to 50% in respect of superior biodegradability. Cellulose ester is most preferably cellulose diacetate.

Tow component fibers may contain various additives, for example, a heat stabilizer, a colorant, a lubricant, a retention aid, and a whiteness improver.

The fineness of tow component fibers may be, for example, 1 to 16 deniers, preferably 1 to 10 deniers, more preferably about 2 to 8 deniers. Tow component fibers may be non-crimped fibers, but preferably crimped fibers. The degree of crimps of crimped fibers may be, for example, 5 to 75 numbers, preferably 10 to 50 numbers, more preferably 15 to 50 numbers per one inch. Furthermore, there are many cases of using crimped fibers evenly crimped. When using crimped fibers, bulky and light-weighted absorbent core can be manufactured, as well as highly integral tow can be easily manufactured due to entanglement between fibers. The cross sectional shape of tow component fibers is not particularly limited, but may be any one of circular, elliptical, heteromorphic (for example, Y-shaped, X-shaped, I-shaped, and R-shaped) or hollow shapes. Tow component fibers may be used in the form of tow (fiber bundle) made by tying up, for example, 3,000 to 1,000,000 numbers, preferably about 5,000 to 1,000,000 numbers of mono-filaments. A fiber bundle is preferably formed of about 3,000 to 1,000,000 numbers of bundled continuous fibers.

Since tow is poor in entanglement between fibers, mainly to keep configuration, binders acting to bond or fuse contact portions of fibers. Examples of binders include plasticizing esters such as triacetin, triethylene glycol diacetate, triethylene glycol dipropionate, dibutyl phthalate, dimethoxyethyl phthalate, and triethyl citrate ester, and additionally various resin adhesives, particularly thermoplastic resins.

Thermoplastic resins to be used as binders are resins that exhibit adhesion by fusion and solidification, and include water-insoluble or low water-soluble resins and water-soluble resins. Water-insoluble or low water-soluble resins and water-soluble resins may be used together as necessary.

Examples of water-insoluble or low water-soluble resins include, olefin-based mono or copolymers such as polyethylene, polypropylene, ethylene-propylene copolymer, and ethylene-vinyl acetate copolymer; acryl resins such as polyvinyl acetate, polymethyl methacrylate, methyl methacrylate-acrylic ester copolymer, and copolymer of (metha) acrylic monomer and styrenic monomer; stylene-based polymers such as polyvinyl chloride, vinyl acetate-vinyl chloride copolymer, polystylene, and copolymer of stylene-based monomer and (metha) acrylic monomer; polyesters that may be denatured; polyamides such as nylon 11, nylon 12, nylon 610, and nylon 612, rosin derivatives (for example, rosin esters), hydrocarbon resins (for example, terpene resins, dicyclopentadiene resins, and petroleum resins); and hydrogenerated hydrocarbon resins. These thermoplastic reins may be used alone or in combination.

Examples of water-soluble resins include various water-soluble high polymers, for example, vinyl water-soluble resins such as polyvinyl alcohol, polyvinyl pyrolidone, polyvinyl ether, and copolymer of vinyl monomer and copolymerizable monomer having carboxyl groups, sulfonic groups or salts thereof, polyalkylene oxides, water-soluble polyesters, and water-soluble polyamides. These water-soluble reins may be used alone or in combination.

Thermoplastic resins may be added with various additives such as antioxidant, stabilizer such as ultraviolet absorber, filler, plasticizer, preservative agent, and mildewproofing agent.

However, to the utmost extent, the use of binder components interrupting the entry of super absorbent polymer particles should be avoided. It is the best to use no binder components interrupting the entry of super absorbent polymer particles.

Tow can be manufactured by known methods, so that no detailed descriptions will be made. Bale of tow of cellulose diacetate capable of being preferably used in an absorbent body 50 is available from Celanese Corporation or Daicel Chemical Industries, Ltd. The bale of tow of cellulose diacetate is about 0.5 g/cm$^3$ in density and 400 to 600 kg in total weight.

Tow is peeled from this bale, and opened in a wide strip shape so as to have a desired size and bulk. The width of tow to be opened may be selected as needed, for example, 100 to 2000 mm in width, preferably 150 to 1500 mm in width, most preferably about 100 to 300 mm of the width of an absorbent core of a product. Furthermore, by adjusting opening degrees of tow, the density of an absorbent core can be adjusted.

A fiber aggregate is preferably not more than 0.0075 g/cm$^3$, particularly preferably 0.0060 to 0.0070 g/cm$^3$ in fiber density when thickness is 10 mm. In case of excessively high fiber density, there will be less advantage in using a fiber aggregate formed by opening of tow, for example, light saving or thinning will be hard to achieve. Moreover, the basis weight of a fiber aggregate is preferably not more than 0.0075 g/cm$^2$, particularly preferably 0.060 to 0.070 g/cm$^2$. Excessively high basis weight of fibers eliminates the advantages of using a fiber aggregate formed by opening tow, and for example it becomes difficult to be light saving of thinning. The basis weight of fibers can be adjusted by selection of tows to be a raw fabric, or manufacturing conditions thereof.

Examples of opening methods of tow include the method in which tow is entrained about a plurality of opening rolls, and tow is gradually enlarged in width as tow goes on to be opened, the method of repeating tension (elongation) and relaxation (contraction) to be opened, and the method of widening and opening with the use of a compressed air.

The super absorbent polymer according to the present invention is preferably super absorbent polymer particles, and the super absorbent polymer particles in the present application include not only "particles" but also "powders". In terms of particle size, super absorbent polymer particles can employ those used in this type of absorbent articles as they are, for example, those of particle size of 20 to 850 μm. Specifically, super absorbent polymer particles of the following characteristics may be used.

mean particle size: about 350 μm
particle size distribution
850 μm on: 0%
500 μm on: 12.2%
250 μm on: 75.7%
180 μm on: 8.8%
106 μm on: 2.4%
106 μm pass: 0.9%
primary particle size: 110-120 μm The raw material of Super absorbent polymer particles may be used without particular limitations, but those of the amount of water absorption of not less than 50 g/g are preferred.

Super absorbent polymer particles include starched, cellulosic, or synthetic polymers, and may empoly saponified substances of starch-acrylate (salt) graft copolymers or starch-acrylonitrile copolymers, crosslinking substances of sodium carboxymethylcellulose, or acrylate (salt) polymers. Although the configuration of super absorbent polymer particles is preferably particulates that are normally used, other configurations may be used.

In addition, super absorbent polymer particles of the speed of water absorption of not more than 45 seconds are preferably used. When the speed of water absorption exceeds 45 seconds, the so-called reversing in which body fluids having been fed into an absorbent body are reversed outside the absorbent body is likely to occur.

In addition, super absorbent polymer particles of gel strength of not less than 900 Pa are preferably used. Whereby, by using tow, even in the case of a bulky absorbent core, sticky feeling after body fluids have been absorbed can be effectively suppressed.

The basis weight of super absorbent polymer particles may be suitably determined depending on the amount of absorption to be required for application of these absorbent bodies.

Thus, this basis weight cannot be said with absolute certainty, but may be, for example, not more than 400 g/m$^2$. In case of excessively less basis weight of polymers, absorption performance cannot be kept. On the contrary, in case of excessively more basis weight, not only effects will be saturated, but also the above-described shuffling discomfort will be provided due to excess super absorbent polymer particles.

If necessary, super absorbent polymer particles can be adjusted in dispersion density or the amount of dispersion in a planer direction of an absorbent core 56. For example, there may be dispersed more super absorbent polymer particles at an excretion site of body fluids than other sites. In the case of considering a sex difference, a dispersion density (amount) on the front side is made higher for men, and a dispersion density (amount) at the central portion is made higher for women. Furthermore, there may be provided the portions with no presence of polymers locally (for example, in spotted pattern) in the planer direction of an absorbent core 56.

When necessary, a plurality of super absorbent polymer particles of different particle size distributions may be prepared, and dispersed and projected in sequence in a thickness direction. For example, there are located spaced apart in a line direction a plurality of the below-described super absorbent polymer particle dispersion means 90, previously super absorbent polymer particles of small particle size distribution are dispersed and projected, and thereafter super absorbent polymer particles of large particle size distribution are dispersed and projected, whereby those of small particle size distribution can be distributed on the lower side of an absorbent core 56, and those of large particle size distribution can be distributed on the upper side. This embodiment is advantageous for super absorbent polymer particles of small particle size distribution to enter the deep portion in a fiber aggregate.

The portion between super absorbent polymers and a fiber aggregate decides absorption characteristics. As the weight ratio in a planer area of 5 cm×5 cm in the region of directly receiving body fluids in an absorbent core 56, super absorbent polymer particles/filament weight is preferably 1 to 14, particularly preferably 3 to 9.

On the other hand, as to the size of an absorbent core 56, a planer-projected area is preferably not less than 250 cm$^2$, preferably 400 cm$^2$ or more, and the thickness is 10 mm or below, preferably 0.5-10 mm, particularly preferably 1 to 5 mm. When the size of an absorbent core is within this range, it is possible to make it light saving and thinning, and it is extremely advantageous in order to improve a restoring force without the increase of weight, thickness, or costs. Further, an absorbent core is constructed to be preferably not more than 25 g, particularly preferably 10 to 20 g in weight. In particular, if it is 15 g or below, the light saving effect by use of fiber aggregate made of a tow becomes conspicuous.

The compression resilience RC of an absorbent core 56 is preferably 40 to 60%, preferably 45-60%, particularly preferably 50 to 60%. Whereby, an absorbent core itself can come to exhibit a sufficient restoring force. In addition, when the compression energy WC of an absorbent core 56 is 4.0 to 10.0 gf·cm/cm$^2$, preferably 4.-7.0 gf·cm/cm$^2$, since an article can be compressed to be compact at the same level or not less than the conventional level in packaging, it is preferred.

These compression characteristics may be adjusted by adjustment of the fiber density of a fiber aggregate by e.g., opening, selection of fiber materials, selection of types of binders such as plasticizers and adjustment of levels of processing, or combinations thereof.

Herein, compression energy (WC) is energy consumption in the case of pressing to 50 g (it is a thickness at this time in the embodiment) at the central portion of a test piece (holding sheet) cut in length of 200 mm and width of 50 mm.

This compression energy (WC) can be measured using a handy compression tester (KES-G5, manufactured by Kato Tech Co., Ltd.). Measurement conditions in the case of using this tester, SENS: 2, the type of a force gauge: 1 kg, SPEED RANGE: STD, DEF sensitivity: 20, pressed area: 2 cm$^2$, taking in interval: 0.1 (standard), STROKE SET: 5.0, and upper load: 50 gf/cm$^2$.

On the other hand, compression resilience (RC) is a parameter representing recoverability when fibers are compressed. Therefore, in case of high recoverability, compression resilience comes to be larger. This compression resilience can be measured using a handy compression tester. (KES-G5, manufactured by Kato Tech Co., Ltd.). Measurement conditions in the case of using this tester are the same as in the case of the above-mentioned compression energy.

As a covering sheet 58, tissue papers, particularly crepe papers, non-woven cloths, polyethylene laminate non-woven cloths, sheets with micro-pores therethrough may be used. In this regard, sheets through which no super absorbent polymer particles are slipped out are desired. In the case of using non-woven cloths instead of crepe papers, hydrophilic SMMS (spun bond/melt-blown/melt-blown/spunbond) non-woven cloths are particularly preferred, and polypropylene, polyethylene/polypropylene and the like may be used as materials thereof. A basis weight thereof is preferably 8 to 20 g/m$^2$, particularly preferably 10 to 15 g/m$^2$.

Figure 19:
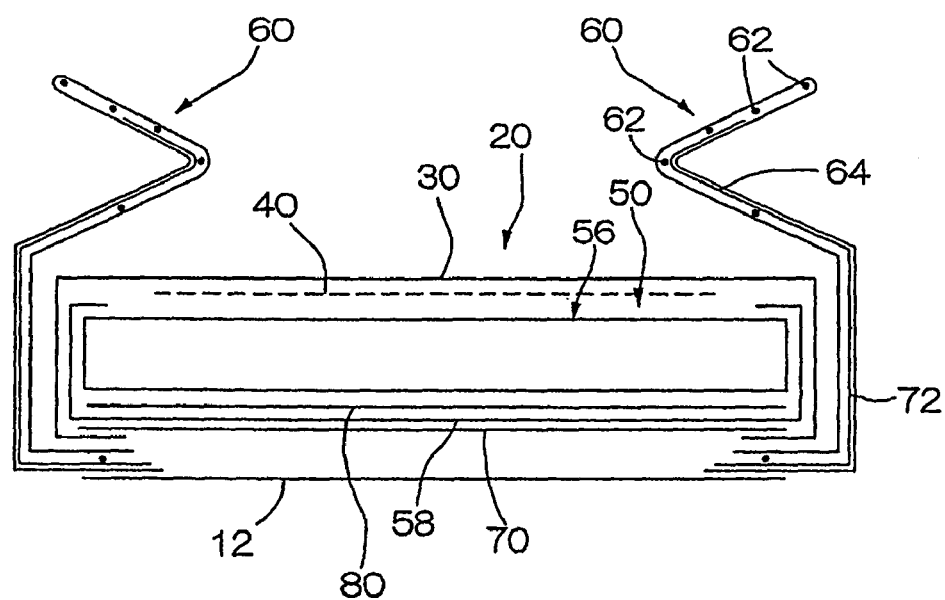
FIG. 19 is a sectional view showing another embodiment of an absorbent body.

This covering sheet 58, as shown in FIG. 3, may be in embodiment of enveloping the entire layer of a fiber aggregate and super absorbent polymer particles 54, and additionally, as shown in, for example, FIG. 19, may be in embodiment of covering only the backside and sides of this layer. Furthermore, not shown, the covering sheet 58 may be in embodiment that only the top and sides of an absorbent core 56 are covered with crepe papers or non-woven cloths, and the underside thereof is covered with a body fluid impermeable sheet such as polyethylene, or may be in embodiment that the top of an absorbent core 56 is covered with crepe papers or non-woven cloths, and the sides and underside thereof are covered with a body fluid impermeable sheet such as polyethylene (each material thereof will be the component of a covering sheet). As necessary, although the covering sheet 58 may be in embodiment that the layer of a fiber aggregate and super absorbent polymer particles 54 is sandwiched by vertical two-layer sheets, or in embodiment that the sheets are located only at the underside and top, movement of super absorbent polymer particles is hard to prevent, so that they are not desired embodiments.

There may be interposed between a holding sheet 80 and an absorbent core 56 super absorbent polymer particles 54 by e.g., dispersion thereof. There are some cases where super absorbent polymer particles 54 are slipped out of a fiber aggregate at the time of dispersion and projection to the fiber aggregate or at the process thereafter, or in the distribution process until consumers use. Concavo-convexes of super absorbent polymer particle groups having been slipped out of the fiber aggregate provide a shuffling discomfort when consumers touch them with hands when using. Then, there is interposed between an absorbent core 56 and a covering sheet 58 a holding sheet 80 having a holding function of absorbent polymers. This holding sheet 80 enforces the strength of papers insufficient solely with a covering sheet 58 such as tissue papers (crape papers), to reduce or prevent discomfort when consumers touch with hands at the time of using.

Furthermore, with reference to FIG. 14, conceptually is shown the case where there are provided super absorbent polymer particles under an absorbent core 56, or the case where super absorbent polymer particles having been contained in the absorbent core 56 are slipped out of a fiber aggregate, and gathered on a holding sheet 80 at stages from manufacturing until being used by consumers.

Materials of a holding sheet 80 are not particularly limited, but have only to function to hold absorbent polymers. Specifically, examples thereof include non-woven cloths, crimped pulps, low-absorbent cotton fibers (for example, non-degreased cotton fibers, degreased cotton fibers, rayon fibers processed with water-repellent agents or hydrophobic agents), polyethylene fibers, polyester fibers, acryl fibers, polypropylene fibers, silk, cotton, linen, nylon, polyurethane, and acetate fibers.

In the case of taking a non-woven cloth as a holding sheet 80, this holding sheet 80 may be non-woven cloth that is 0.01 to 10.00 gfcm/cm$^2$, preferably 0.01 to 1.00 gfcm/cm$^2$ in compression energy based on KES test, as well as 10 to 100%, preferably 70 to 100% in compression resilience. Further, the holding sheet 80 is preferably 0.05 to 0.75 g·cm$^2$/cm in elasticity in a front-back direction of a product in order to reduce or eliminate shuffling discomfort provided by super absorbent polymer particles. Herein, "elasticity in front-back direction of a product" means the one obtained as values in the case where a sample cut in length of 200 mm and width of 20 mm is folded in the range of DFE sensitivity 20, curvature 0.0 cm$^{-1}$ to 0.5 cm$^{-1}$ using a pure bending tester ("KES-FB2" manufactured by Kato Tech Co., Ltd.).

The reason why there is provided a holding sheet 80 is that absorbent polymers having been slipped off (slipped out) downward from the absorbent core 56 are held. Therefore, super absorbent polymer particles having been slipped out are brought in contact with users via a covering sheet 58 and a holding sheet 80, so that there is no risk of shuffling discomfort being transmitted to users. In particular, in case of non-woven cloths having the above-mentioned compression energy and compression resilience, functions as a holding sheet will be sufficiently exhibited.

Furthermore, since absorbent polymers having been slipped out are held by a holding sheet 80, and are not moved on a covering sheet 58, there is no fear of the occurrence of localization of absorption capacities. In particular, to prevent super absorbent polymer particles from moving on the holding sheet 80, there may be preliminarily applied on the holding sheet 80 e.g., hot melt adhesives having adhesion. Moreover, by making the top face of the holding sheet 80 (face opposite to the side to be used) a rough face, movement of super absorbent polymer particles on the holding sheet 80 may be prevented. Thus, examples of means of making rough or fuzzing include making a non-net face, not being a net face at the time of manufacturing non-woven cloths, marble machining, needle-punching, or brushing.

A holding sheet 80, as w shown in FIG. 3 and the like, may be located only below an absorbent core 56, or as shown in FIG. 14, may be go along the sides of the absorbent core 56 and turned up to the top thereof, to be extended. Furthermore, a plurality of holding sheets 80 may be used in a stack.

Although the above-mentioned example is the one in which there is provided a holding sheet 80 between an absorbent core 56 and a backside site of a covering sheet 58, the holding sheet 80 may be more backward than the covering sheet 58 (this embodiment is not shown), or a covering sheet 58 itself may be made to function as a holding sheet without an additional provision of a holding sheet 80. That is, if only there is provided a holding sheet on the backside with respect to an absorbent core 56, a shuffling discomfort in the case of being touched from the backside of a product will be reduced or will not occur.

A body fluid impermeable sheet 70 merely means a sheet located on the backside of an absorbent core 56, and in the present embodiment, is a sheet to interpose the absorbent core 56 between a top sheet 30 and this body fluid impermeable sheet 70. Thus, body fluid impermeable sheets are not particularly limited in materials thereof. Specifically, for example, olefin-based resins such as polyethylene or polypropylene, laminate non-woven cloths made by e.g., polyethylene sheet being laminated with a non-woven cloth, or non-woven cloths in which a water proof film is interposed to ensure a substantial liquid impervious properties (in this case, body fluid impermeable sheet is formed of a water-proof film and a non-woven cloth) are provided as an example. It may be a matter of course to be additionally provided as examples materials having liquid impervious properties as well as moisture permeability that are preferably used in recent years from the viewpoint of preventing sticky feeling. As sheets of these materials having liquid impervious properties as well as moisture permeability, may be provided as examples microporous sheets made by the process in which olefin-based resins such as polyethylene or polypropylene are admixed kneaded with an inorganic filler to mold sheets, and thereafter stretched in one or two axial directions.

A body fluid impermeable sheet 70 is extended on the face to be used in the form of the so-called wound around a forehead (not shown), thereby enabling to prevent side leakage of body fluids. In the present embodiment, this side leakage is prevented due to that there is interposed between double barrier sheets 64 forming barrier cuffs 60 a second body fluid impermeable sheet 72. According to this embodiment, the second body fluid impermeable sheet 72 is extended up to the rises of barrier cuffs 60, so that an advantage exits in that side leakage of body fluids rolling over a top sheet 30 and spread sideward or soft stools between the barrier cuffs 60, 60 can be prevented.

Barrier cuffs 60, 60 located at both sides of a product function to interrupt urines or soft stools rolling over a top sheet 30 and moved sideward, and to prevent side leakage, but are just additional elements.

The barrier cuffs 60 shown in the drawing are formed of double-layered barrier sheets, and configured to cover turned-in portions of a top sheet 30 from the backside of an absorbent core 56 to protrude on the front side. To interrupt urine rolling over the top sheet 30 and is moved sideward, particularly a body fluid impermeable sheet 70 are inserted at the sides between the double non-woven cloth sheets, and is extended on the way of the barrier cuffs 60 protruding to the front side.

In addition, although barrier cuffs 60 themselves can be designed in configuration as appropriate, in the illustrated example, elastic members, for example, rubber threads 62 are fixed under tension at tip portions and intermediate portions of protrusions of the barrier cuffs 60, and the barrier cuffs 60 are arranged to rise by an elastic constrictive force thereof in use states. Owing that the rubber threads 62 at the intermediate portion are positioned at the more central portion than the rubber threads 62, 62 at the tip portions, and fixed to the front and back end portions of a top sheet 30, as shown in FIG. 3, the barrier cuffs 60 are to be in embodiment to rise obliquely toward the central portion at the base portions, and to rise obliquely outward at the tip portions from the intermediate portions.

Materials of barriers sheets may be the ones having properties of permeating body fluids or the ones having properties of not permeating body fluids, and types thereof are not particularly limited. For example, the same materials as exemplified as a top sheet 30 and a body fluid impermeable sheet 70 may be used. In respect of e.g., preventing rash due to poor feel or friction, however, non-woven cloths are preferred, and bulky non-woven cloths such as air-through nowoven cloths are more preferred.

Furthermore, depending on functions to be considered important, respective water-repellent non-woven cloths or hydrophilic non-woven cloths may be used alone or in combination. For example, in case of considering important penetration prevention of body fluids or improvement in feel, preferred are water-repellent non-woven cloths, for example, water-repellent non-woven cloths coated with silicon-based, paraffin-based, alkyl chromic chloride-based water repellent agents. On the contrary, in case of considering important absorption of body fluids, hydrophilic non-woven cloths, non-woven cloths made of e.g., hydrophilic natural fibers, synthetic fibers, and regenerated fibers, as well as non-woven cloths made by hydrophilic-processing non-hydrophilic fibers with hydrophilizing agents.

Elastic members have only to be elastic, and types thereof are not particularly limited.

For example, elastic hot melt, elastic films, rubber threads, and flat rubbers may be provided as an example. Examples of materials thereof may include styrene-based, olefin-based, urethane-based, ester-based rubbers, or foams of polyurethane, polyethylene, polystyrene, styrene butadiene, silicone, polyester or the like.

Figure 21:
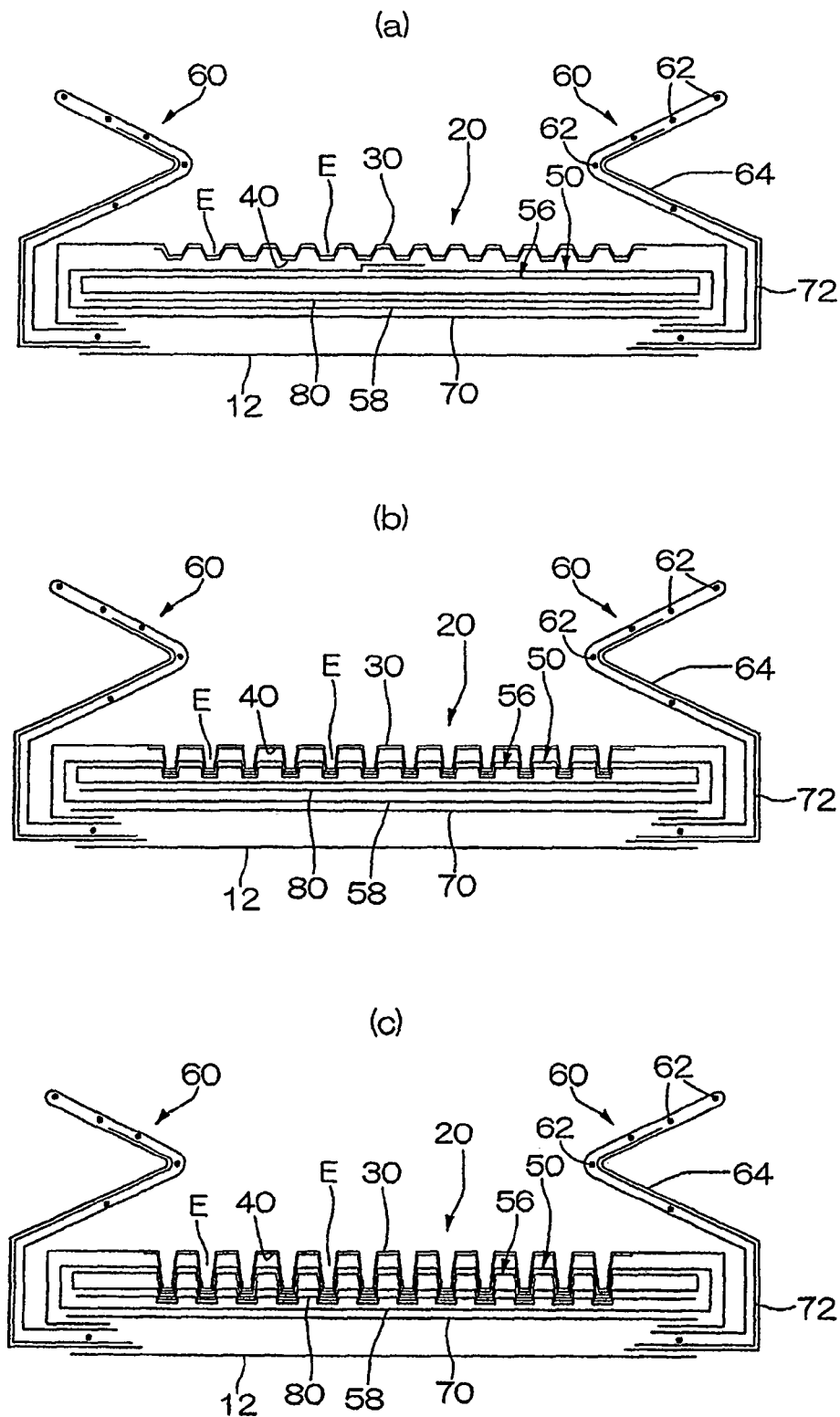
FIG. 21 is a sectional view showing another embodiment of an absorbent body.

There may be formed concaves E by embossing in a thickness direction from the front side of a top sheet 30. In this case, in addition to that embossed concaves E are formed only at the top sheet 30, as shown in FIG. 21 (*a*), embossed concaves E may be formed at both the top sheet 30 and an intermediate sheet 40; as shown in FIG. 21 (*b*), embossed concaves E may be formed so as to extend from the front side of the top sheet 30 to a part or substantially the whole in a thickness direction of an absorbent core 56; or as shown in FIG. 21 (*c*), embossed concaves E may be formed so as to extend from the front side of the top sheet 30 to a holding sheet 80. To allow embossed concaves E to form at both the top sheet 30 and the intermediate sheet 40, an intermediate sheet 40 is preferably within the range of 8 to 40 g/m$^2$ in basis weight, and preferably within the range of 0.2 to 1.5 mm in thickness, and a top sheet 30 is preferably within the range of 15 to 80 g/m$^2$ in basis weight, and preferably within the range of 0.2 to 3.5 mm in thickness in respect that sufficient embossing can be made on the conditions of not impairing liquid impervious properties.

In addition, embossed concaves may be formed only at the intermediate sheet 40 without formation of concaves at the top sheet 30, embossed concaves may be formed only at the absorbent core 56 without formation of concaves at the top sheet 30 and the intermediate sheet 40, or embossed concaves may be formed only at the absorbent core 56 without formation of concaves at the top sheet 30, the intermediate sheet 40 and the covering sheet 58.

Concaves E function to induce and spread body fluids in an extended direction thereof. Therefore, in case where the concaves E are made to be continuous substantially in grooves (including the case in which a plurality of concaves are aligned spaced apart to form one groove), body fluids will roll over the concaves E on the front side layer to be spread before reaching an absorbent core, and thus a wider portion of the absorbent core can be used for absorption. Accordingly, the absorption capacity of the entire product will be increased, to obtain an absorbent article in which leakage or reversing from sides due to an insufficient absorption capacity is hard to occur.

On the other hand, although an absorbent core 56 made of tow is likely to be lower in rigidity as compared with conventional pulp articles, rigidity is increased when embossed concaves are formed at the absorbent core 56, thus to be preferred. Although not shown, to increase rigidity of an absorbent body 50, it is also a preferred embodiment in which embossed concaves are formed in a thickness direction from the backside (the opposite side with respect to a top sheet 30) of the absorbent core 56. To form these concaves at the backside, embossing can be done integrally from the backside of a holding sheet 80, a covering sheet 58, a body fluid impermeable sheet 70 or an exterior sheet 12 up to the absorbent core 56. Furthermore, although these concaves on the backside are preferably formed along with the concaves E on the front side, only the concaves on the backside may be formed without formation of the concaves E on the front side. In the case of providing concaves on both the front side and the backside, the shapes of the concaves may be common on the front and back sides, or may be different on the front and back sides.

Embossed concaves function to induce and spread body fluids in an extended direction, and further to improve rigidity. Therefore, the embodiments of embossed concaves are desired to determine taking these effects into consideration. For example, concaves may be continuous substantially in grooves (including the case where a plurality of concaves are aligned spaced apart to form one groove), as well as a plurality of concaves may be formed spaced apart in a dotted manner. Furthermore, in terms of planar patterns, may be employed embodiments in which groove-like or dotted concaves are formed in a longitudinal direction, a width direction, in lattice of combination thereof, in a zigzag manner reciprocating in a width direction (staggered), or in irregular patterns of products. In addition, suitable embodiments such as pin-like, Mt. Fuji-like, and bellows-like patterns may be employed.

Furthermore, respective components of an absorbent body 20 are fixed to each other with hot-melt adhesives and the like. In the case of application of adhesives, there may be intentionally provided applied portions and non-applied portions thereof at bonded surfaces. Moreover, adhesives can be applied by the methods of curtain coating, spiral coating, slot coating, control-seam coating (omega-shaped coating), or bead coating.

Figure 22:
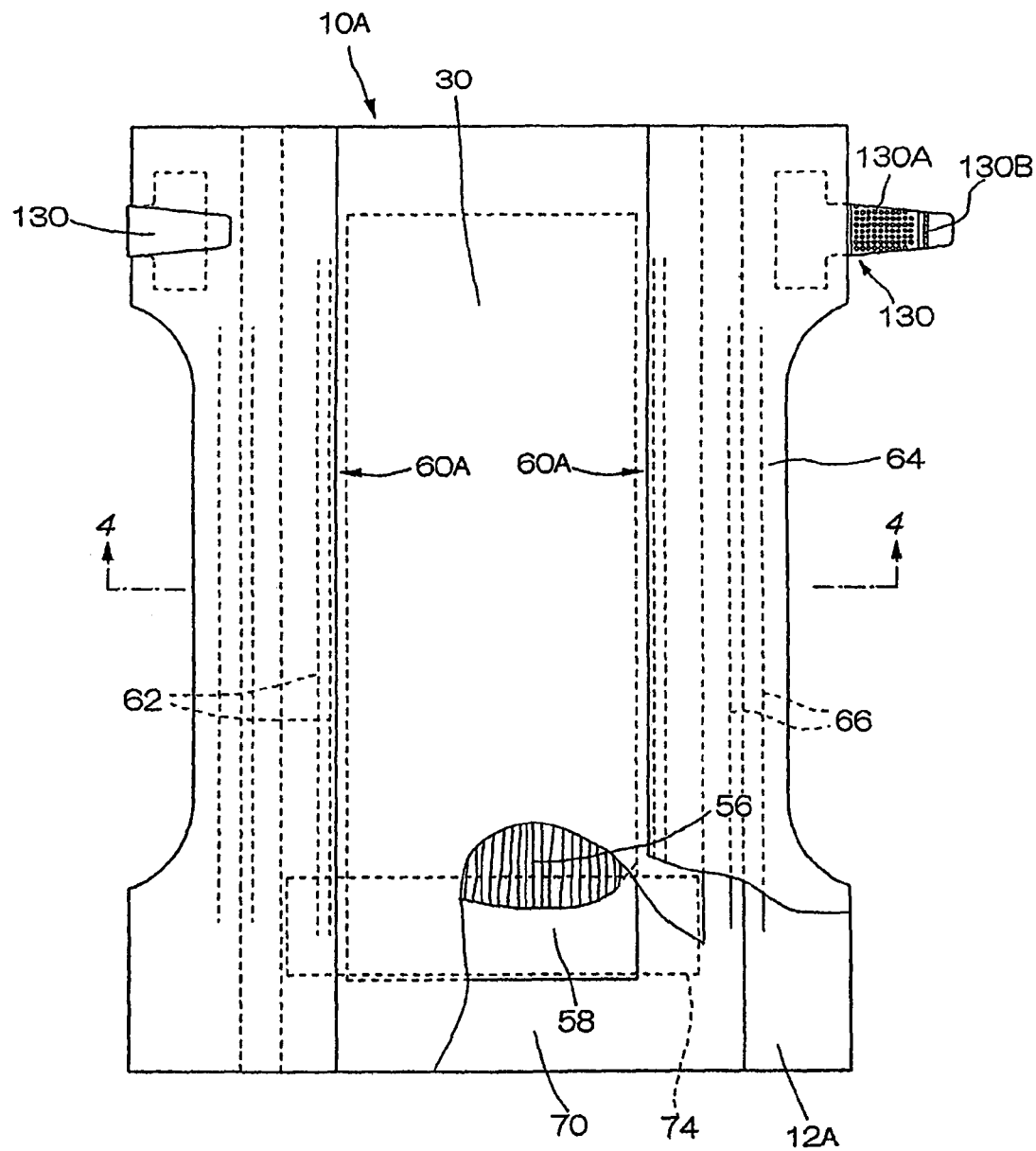
FIG. 22 is a plan view showing a tape-type diaper in a deployed state.
Figure 23:
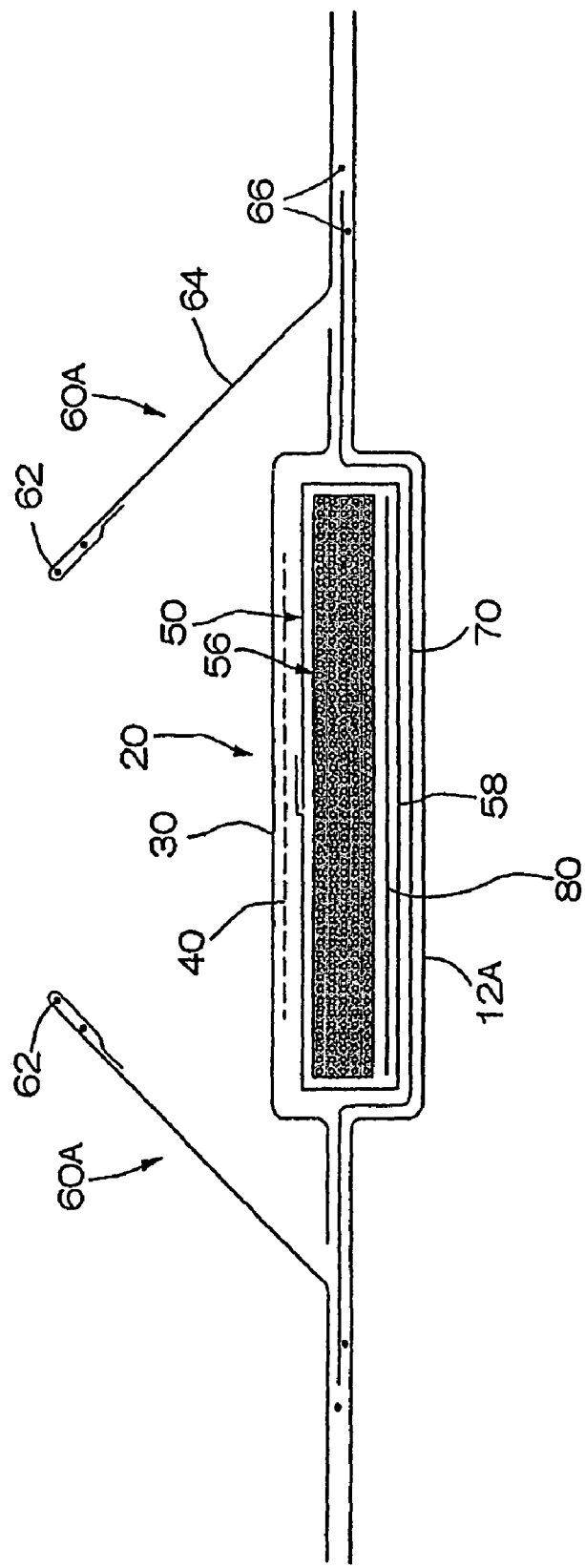
FIG. 23 is a sectional view taken along the line 4-4 of FIG. 22.

On the contrary, FIGS. 22 and 23 show an example of tape-type disposable diapers. FIG. 23 is a view taken along the line 4-4 in FIG. 22, and illustrates an absorbent body 20 in rather exaggerated way.

A tape-type disposable diaper 10A is a diaper which includes fastening pieces attached to both side ends on the backside of the diaper, and includes hook elements at fastening faces of these fastening pieces, as well as in which a back sheet forming the backside of the diaper is to be a non-woven cloth laminate, and hook elements of fastening pieces can be engaged with any point on the surface of the back sheet when the diaper is worn.

An absorbent body 20 is the one in which an absorbent core is interposed between a top sheet 30 and a body fluid impermeable sheet 70. This absorbent core 56 is enveloped at its entirety by a covering sheet 58 made of tissue paper, and is rectangular viewed in a plane. There is provided a holding sheet 80 between the absorbent core 56 and the covering sheet 58.

Furthermore, there is interposed an intermediate sheet 40 between the top sheet and the absorbent core 56. The body fluid impermeable sheet 70 is a rectangle wider than the absorbent core 56, and there is provided outward thereof a back sheet 12A made of non-woven cloth having an hourglass shape.

A top sheet 30 is a rectangle wider than an absorbent core 56, extended rather outward from the side edges of the absorbent core 56, and fixed to a body fluid impermeable sheet 70 with hot-melt adhesives.

There are formed at both side portions of a diaper barrier cuffs 60A protruding to the side to be used. These barrier cuffs 60A are formed of a barrier sheet 64 made of non-woven cloth continuous substantially in a width direction, and elastic members, for example, rubber threads 62 as one or plural numbers of elastic members around legs formed of rubber threads. Reference numeral 130 designates fastening pieces of hook and loop fasteners.

The interior of barrier sheets 64 has a leading end of fixing in a position spaced apart from the side edge of a top sheet 30, and fixed with e.g., hot-melt adhesives at the outward portions in a width direction from this fixing leading end to the extended edge of a body fluid impermeable sheet 70. The exterior of the barrier sheet 64 is fixed to a back sheet 12A at the underside thereof with e.g., hot-melt adhesives. Further, there are provided elastic members for gasket cuffs, for example, rubber threads 66.

The leading end fixed to a body fluid impermeable sheet 70 of the interior of the barrier sheets 64 forms an uprising end of the barrier cuffs 60A. Around the legs, the insides from these uprising ends are free portions not fixed to a product body, and these free portions are to rise up by an elastic constrictive force provided by rubber threads 62.

In the present example, by using hook and loop fasteners as fastening pieces 130, these fastening pieces 130 can be mechanically fastened with respect to a back sheet 12A. Thus, the so-called target tape can be omitted, as well as fastened positions with the fastening pieces 130 can be selected without restraint.

Fastening pieces 130 are bonded with, for example, adhesives at the bases of fastening backings made of plastics, poly laminate non-woven cloths, papers and the like, and include hook elements 130A on the tip sides. The hook elements 130A are bonded to the fastening backings with adhesives. The hook elements 130 include multiple engaging pieces on the outside thereof. There is included a temporary adhesive part 130B on the more distal side than the hook elements 130A. By the temporary adhesive parts 130B being bonded to the barrier sheets 64 at the final stage of product assembly, it is arranged to prevent the tip sides of the fastening pieces 130 from being peeled off. When using, the temporary adhesive parts 130B are peeled off against the adhesive force thereof, and the tip sides of the fastening pieces 130 are brought to the front body. The fastening backings are exposed on more distal sides than the temporary adhesive parts 130A to be tab parts to be grabbed.

There is provided on the inside of a back sheet 12A on the opening side of a front body a target printed sheet 74 as a design sheet. There is provided a target printing where designs to be targets of positions of fastening hook elements 130A of the fastening pieces 130 are made so as to be capable of being viewed through the back sheet 12A from the outside.

When a diaper is worn, the diaper is worn around a human body in a boat form, and then an elastic constrictive force from rubber threads 62 are exerted, so that the barrier cuffs 60A rise up by the elastic constrictive force provided by the rubber threads 62 around the legs.

The space surrounded by uprising portions forms the space in which urine or soft stools are confined. When urinated in this space, these urines are passed through a top sheet 30 to be absorbed in an absorbent core 56, as well as solid components of soft stools are prevented from being passed over with the uprising portions of the barrier cuffs 60A acting as barriers. If urines should pass over the distal uprising edges of the uprising portions to be leaked, side leakage is prevented owing to the stop function of planer bearing portions.

In the present embodiment, barrier sheets 64 forming respective uprising cuffs are desired not to have liquid permeability but to be substantially liquid impervious (may have liquid semi-permeability). Further, the surface sheet (unwoven fabric laminated body) of the present invention may be silicone-processed to have liquid repellent properties. In any event, the barrier sheets 64 and the back sheet 12A have air permeability respectively, as well as the barrier sheets 64 and the back sheet 12 are preferably sheets of anti-water pressure characteristics of not less than 100 mm $H^2O$ respectively. Whereby, air permeability is exhibited at the width directional sides of products, thus enabling to prevent sticky feeling of users.

Other points, for example, fabrics to use at each part are the same as the case of the above-described pant-type paper diaper, so that descriptions dare to be omitted.

Figure 24:
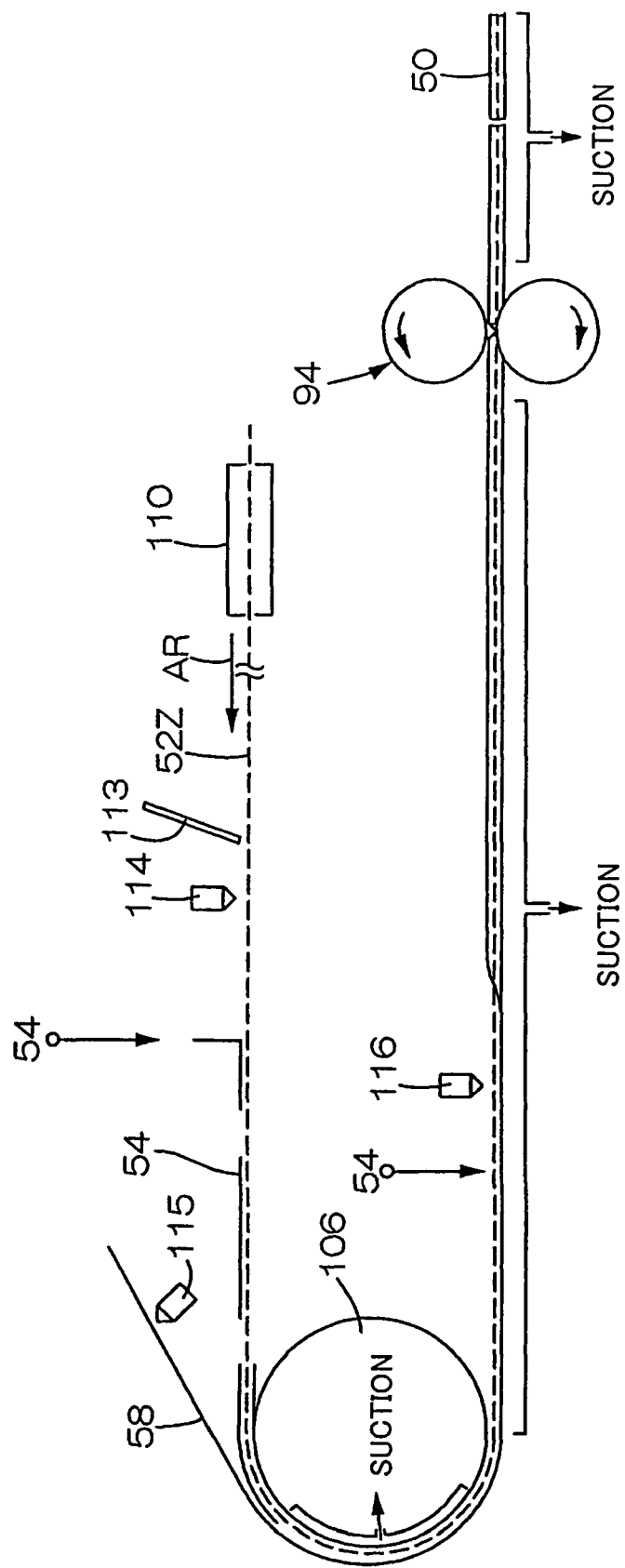
FIG. 24 is a schematic view showing a manufacturing facility example of an absorbent body.
Figure 25:
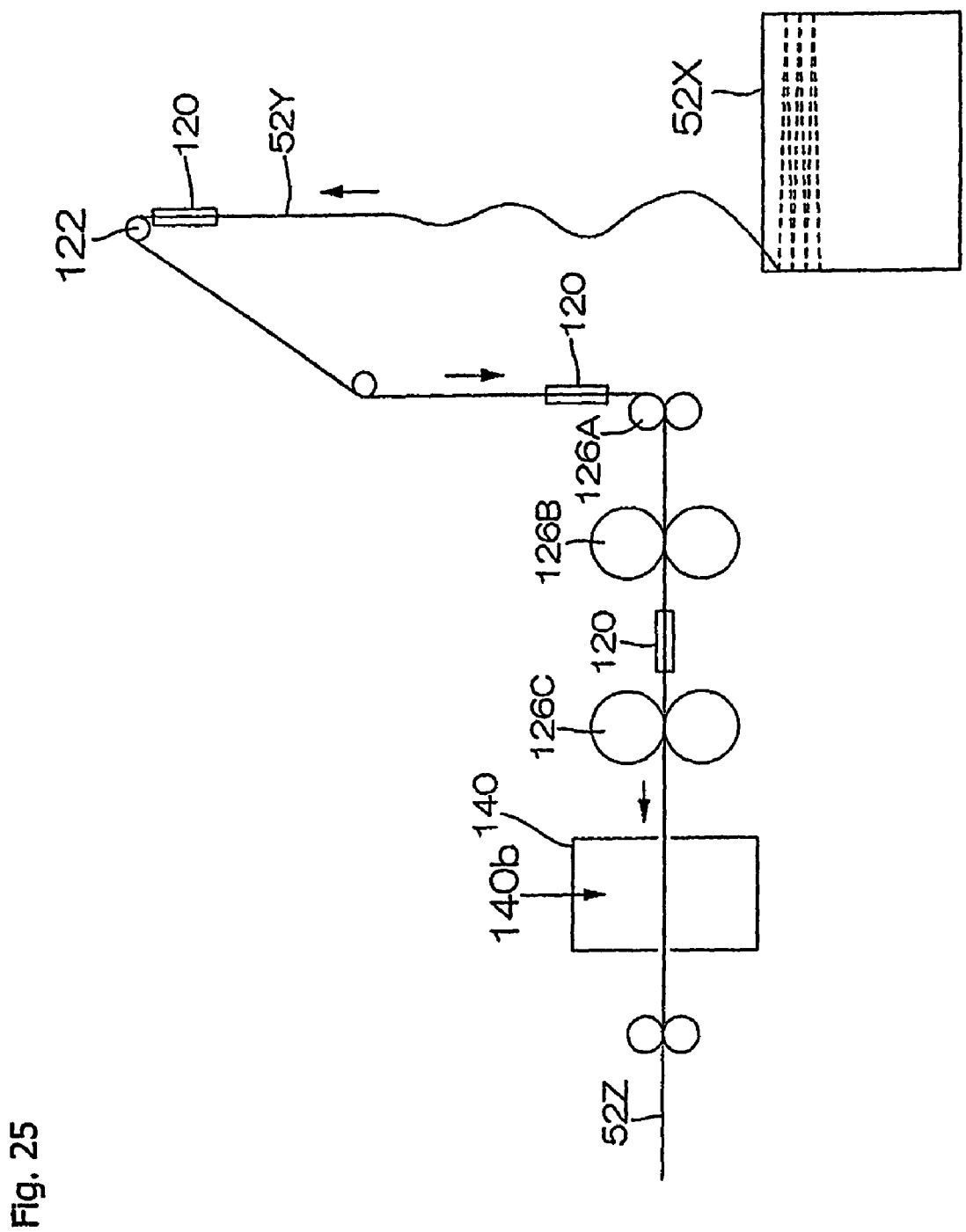
FIG. 25 is a schematic view showing an opening apparatus example.

Now, manufacturing facility examples of an absorbent body will be described. FIG. 24 shows a manufacturing facility example of an absorbent body, in which a fiber aggregate 52Z of a continuous strip shape that is opened in a desired width and density. Upon opening, for example, as shown in FIG. 25, a tow 52Y is fed out in sequence from a tow bale 52X, in this conveying process, is sequentially passed through widening and opening means 120 using a compressed air and an opening section where there are a plurality of combined opening nip rolls 126A, 126B, 126C which circumferential speeds come to be higher as the rolls are positioned more downstream, to be widened and opened, thereafter passed through a binder adding box 140, and applied with a binder 140b (for example, and the box is filled with mist of triacetin), to obtain a fiber aggregate 52Z of a desire width and density. This opening line can be arranged to directly connect to the absorbent body manufacturing line of FIG. 24, and to feed the fiber aggregate 52Z having been manufactured directly to the absorbent body manufacturing line.

A fiber aggregate 52Z having been fed to the absorbent body manufacturing line may be applied with adhesives prior to application of super absorbent polymers. Thus, in an illustrated example, there is located an adhesive applicator 114 upstream of the position of dispersing polymers in a conveyor line. As adhesives, adhesives made of thermoplastic reins (specific examples are as described above) may be preferably used. The adhesives may be applied in a continuous plane by curtain coating or roll coating. There may be provided using spiral coating the portion applied with adhesives and a plurality of portions with no adhesives that are surrounded with the portions applied with adhesives. The amount of application of adhesives may be determined as appropriate, and is preferably not less than g/m$^2$ in the normal case. However, in case of too much application, since the movement of super absorbent polymers is prevented, it is preferably determined to be in the range of 1 to 10 g/m$^2$.

Upon application of adhesives, in the case where opening means 110, 120 utilizing a compressed air are provided on the upstream side of the adhesive applicator, leaked compressed air AR flows into the adhesive applicator 114 along a fiber aggregate 52Z, and thus there is a risk of disturbing the feed of adhesives or making the adhesives dry. Therefore, preferably there is provided a shield 113 upstream of the adhesive applicator 114, and a compressed air AR is interrupted. This shield 113 is preferably disposed at least on the side of the adhesive applicator 114 of a fiber aggregate 52Z.

The fiber aggregate 52Z applied with an adhesive is subsequently dispersed with super absorbent polymer particles 54 on the top face by super absorbent polymer particle dispersing means. This dispersion may be achieved, for example, by merely causing super absorbent polymer particles to drop with one's own weight with respect to the fiber aggregate 52Z.

Figure 26:
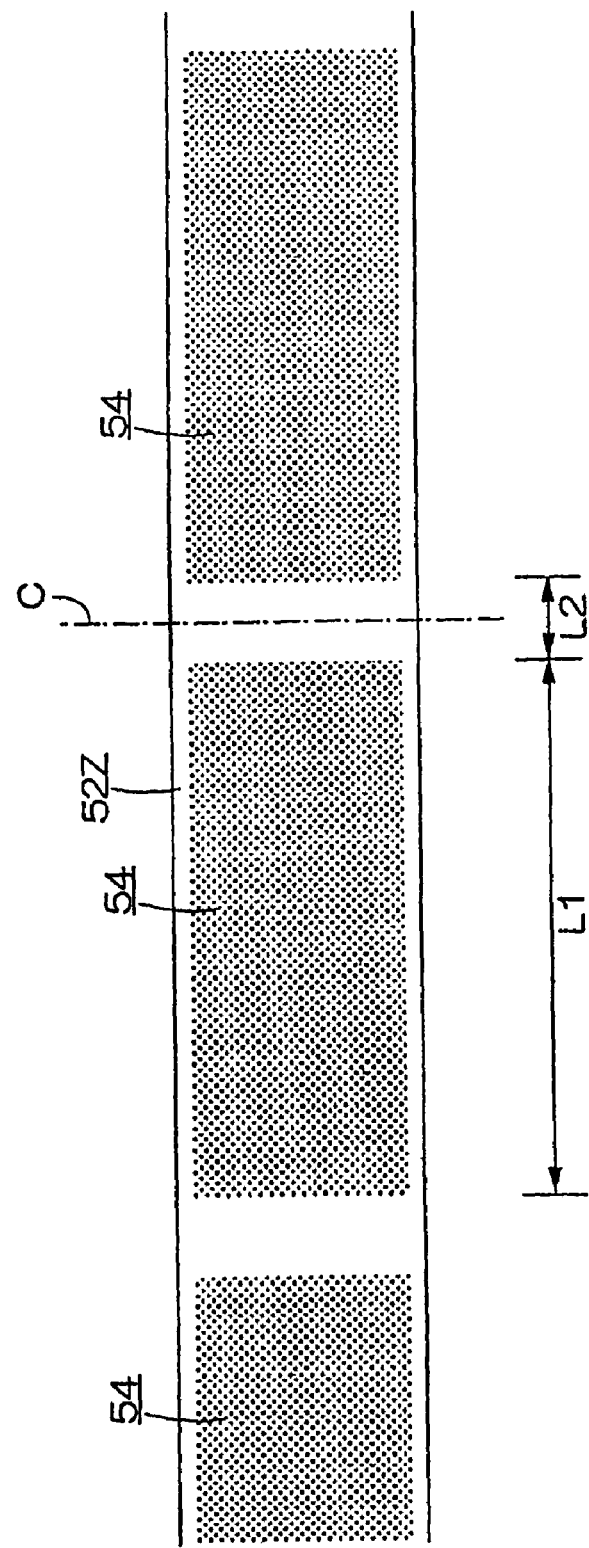
FIG. 26 is a schematic view showing the dispersion state of super absorbent polymer particles.

In this process, as needed, the dispersion amount of super absorbent polymer particles 54 may be periodically changed. Specifically, it is one preferred example in which the dispersing state and the non-dispersing state are repeated alternately, and then there are provided alternately in a conveyor direction the portion applied with super absorbent polymer particles 54 and the portion not applied therewith (super absorbent polymer particles are intermittently applied in a conveyor direction). In this case, as shown in FIG. 26, particularly preferably almost no super absorbent polymer particles 54 are dispersed at cut points C to be cut thereafter. In specific, particularly preferably, cut points C are determined spaced apart at intervals of a suitable length L1 that is rather shorter than the length of one absorbent body, for example, 10 to 30 cm in a conveyor direction, the portions of a length L2 inclusive of sufficient cut margins, for example, about 5 to 20 mm with these cut points C centered are brought in the state in which super absorbent polymer particles 54 are substantially absent across the width, and then cutting is done. Like this, the application process and the cutting process of super absorbent polymer particles 54 are harmonized, whereby as obvious from the below-described examples, much longer product life will be achieved as compared with the case of cutting at the portion provided with the super absorbent polymer particles 54.

There may be provided the portion of a large application amount and the portion of a small application amount by utilizing the periodical change of application amounts of super absorbent polymer particles 54. Further, application amounts may be continuously increased or decreased as well. In this case, may be employed an embodiment in which no super absorbent polymer particles are dispersed at cut points, as well as application amounts are increased as application points approach to the central portion in a conveyor direction between cut points.

In subsequent, although a fiber aggregate 52Z to which super absorbent polymer particles 54 have been dispersed is just rolled with a rolling roll, and fed to the subsequent process, it is a preferred example in which absorption is also made simultaneously with rolling with the use of a vacuum roll 106. This vacuum roll 106 have suction holes in the outer circumferential wall, and is arranged to suck with a suction pump, not shown, from the inside over a predetermined circumferential extent thereof (extent substantially on the left half in an illustrated example). The fiber aggregate dispersed with the super absorbent polymer particles 54 is guided while being guided on the outer circumferential surface by means of the vacuum roll 106. Furthermore, in this process, by making suction through suction holes of the vacuum roll 106, an atmosphere is passed from the application side of super absorbent polymer particles 54, through the fiber aggregate 52Z, to the opposite side (vacuum roll 106 side). By this passing force of gas, the super absorbent polymer particles 54 are made to move into the fiber aggregate 52Z.

In a particularly preferred embodiment, super absorbent polymer particles 54 are dispersed onto a fiber aggregate 52Z, and thereafter sheets such as a covering sheet 58 are further put thereon. In this case, in a vacuum roll 106, suction is made from the side opposite to the side of the fiber aggregate on which the sheet 58 is put on. Like this, when the sheet 58 is put on at the time of suction, as compared with the case with no sheet, a stronger suction force is exerted on the super absorbent polymer particles 54, thus enabling the super absorbent polymer particles 54 to efficiently move and disperse into an internal part of the fiber aggregate 52Z. Examples of these sheets include sheets having liquid permeability such as crepe papers, non-woven cloths, and perforated sheets, and liquid impervious sheets such as polyethylene films. Although, in the illustrated example, this sheet is only a covering sheet 58, in the case where there is provided the above-described holding sheet 80, a holding sheet, not shown, may be provided with the covering sheet 58, and suction may be done in the state in which these sheets are overlapped with the fiber aggregate 52Z.

To fix super absorbent polymer particles 54 to a fiber aggregate 52z, adhesives are applied to the fiber aggregate 52z before the super absorbent polymers are provided, as well as, not shown, adhesives may be applied to the fiber aggregate 52z after the super absorbent polymer particles 54 have been fed as well as before the super absorbent polymer particles 54 are allowed to move into the fiber aggregate 52z, that is, in the illustrated example, adhesives may be applied to the fiber aggregate 52z in the process from being fed with the super absorbent polymer particles 54 until entering the vacuum roll 106.

Furthermore, in the case where super absorbent polymer particles are dispersed on a fiber aggregate 52z, and thereafter sheets such as a holding sheet 80 and a covering sheet 58 are further put thereon, there may be provided in a sheet feed path with respect to a vacuum roll 106 an adhesive applicator 115, and adhesives may be preliminarily fed to a face to be the fiber aggregate 52z side of a sheet 58. In case of employing this embodiment, the super absorbent polymer particles 54 that are exposed on the surface of the fiber aggregate 52z are fixed to the sheet 58 via adhesives, and the super absorbent polymer particles 54 not having been bonded yet will be moved into an internal part of the fiber aggregate 52z by later suction. However, since there are a risk of the occurrence of such defects resulted from the adhesion of adhesives in the downstream facilities as adhesives are adhered to the vacuum roll 106 to lead to the occurrence of clogging, preferably adhesives dare not to be applied with respect to the sheet 58.

Furthermore, there may be provided an applicator 116 of adhesives on the side of a fiber aggregate 52z being exposed (the side opposite to the sheet 58, being the top in the drawing) downstream of a vacuum roll 106, and adhesives may be fed with respect to the fiber aggregate 52z after having been sucked, that is after the super absorbent polymer particles 54 have been moved. Incase of employing this embodiment, the super absorbent polymer particles 54 having been moved to the side opposite to the side on which polymers have been applied in the fiber aggregate 52z out of applied super absorbent polymer particles 54 can be fixed. Moreover, in the case where an additional sheet is put on the exposed side of the fiber aggregate 52z, or both sides of a covering sheet 58 are folded around both ends of the fiber aggregate 52z to cover, the super absorbent polymer particles 54 having been moved to the exposed side of the fiber aggregate 52z can be fixed with respect to this sheet 58.

These adhesives may be applied alone or in combination. As adhesives, adhesives made of thermoplastic resins (as specifically described above) may be preferably used.

Further, a fiber aggregate 52z applied with super absorbent polymers 56 like this, for example, is covered with an additional sheet, or covered around both ends with both side portions of a sheet 58 to be folded with the use of a sailor, and thereafter cut in a predetermined length to be each absorbent body 50.

On the other hand, the amount distribution of super absorbent polymers, the density distribution of super absorbent polymers, and the fiber density distribution with respect to a fiber aggregate 52z are preferably uniform for general purposes. In the case of intending to exhibit special absorption characteristics, however, preferably there may be provided relatively more portions and relatively less portions, or relatively higher portions and relatively lower portions depending on the purpose thereof.

In specific, upon polymer dispersion, there maybe provided the portions of relatively large dispersion amount and the portions of relatively small dispersion amount in a planar direction. In particular, in absorbent articles, there are many cases where the amount of absorption is required to increase at the width directional central portion of an absorbent body. In this case, when polymers are dispersed, the super absorbent polymers may be dispersed so that the amount of super absorbent polymers at the width directional central portion of a fiber aggregate 52z is larger than the amount of super absorbent polymers at both width directional side portions of the fiber aggregate 52z.

Furthermore, upon polymer dispersion, the super absorbent polymers may be dispersed so that the amount of super absorbent polymers at the longitudinal central portion (at the longitudinal central portion of a part to be each absorbent body) of a fiber aggregate 52z is larger than the amount of super absorbent polymers at the front and rear portions in the longitudinal direction of the fiber aggregate 52z. Such dispersion can be achieved by periodically changing the amount of dispersion of the super absorbent polymer particles as described above.

In addition, by providing higher suction portions and lower suction portions at a vacuum roll 016, since the larger amount of super absorbent polymers are positioned on the vacuum roll 106 side as they are positioned in higher suction, there may be provided the portions of relatively high density of super absorbent polymers and the portions of relatively low density thereof in a fiber aggregate. For example, suction at the vacuum roll 106 is made to exert in more strength (or may be in a longer suction time period) with respect to the width directional intermediate portion of a fiber aggregate 52z than both width directional side portions of the fiber aggregate 52z, thereby, as in the above-described eighth embodiment, the density of super absorbent polymers at the width directional central portion of the fiber aggregate 52z can be made higher than the density at both width directional side portions of the fiber aggregate 52z. In such structure, since the absorption rate at the width directional central portion of the fiber aggregate 52z becomes lower, and the absorption rate at both width directional side portions becomes higher, in the case of use in absorbent articles, liquids are likely to spread all over the absorbent body, that is spreading properties are improved.

Furthermore, since in a fiber aggregate 52z made of tow, liquids are likely to flow along the continuous direction of fibers, by providing relatively high fiber density portions and relatively low fiber density portions, special absorption characteristics can be provided. Such arrangement may be achieved by e.g., partially strong opening at the time of manufacturing of the fiber aggregate 52z, or by partially using a bundle of a plurality of tows. As a specific example, as in the above-described ninth embodiment, it is a preferred embodiment in which the fiber density at the width directional central portion of the fiber aggregate 52z, which is formed of tow, is made higher than the fiber density at both width directional side portions. Since in a fiber aggregate 52z made of tow, liquids are likely to flow along the continuous direction of fibers, more liquids will flow along the continuous direction of fibers at the width directional central portion of the fiber aggregate 52z.

In addition, no movement of super absorbent polymer particles 54 utilizing a passing force of gas maybe done. Such embodiment, as shown in FIG. 24, maybe achieved by applying the super absorbent polymer particles 54 to a fiber aggregate on the downstream side of a vacuum roll 106, or by omitting the suction by means of the vacuum roll 106.

Furthermore, super absorbent polymer particles 54 may be applied upstream of a vacuum roll 106, as well as the super absorbent polymer particles 54 may be applied to the fiber aggregate 52z also downstream of the vacuum roll 106. In this case, the super absorbent polymer particles 54 may be applied both on the upstream side ant the downstream side of the vacuum roll 106 all over the portion to be one absorbent body; or the super absorbent polymer particles 54 are applied upstream of the vacuum roll 106 with respect to a part of the portion to be one absorbent body, and the super absorbent polymer particles 54 are applied downstream of the vacuum roll 106 with respect to the other portions.

Moreover, as needed, in the case where super absorbent polymer particles 54 are applied downstream of a vacuum roll 106, particularly downstream of the vacuum roll 106 e.g., in the case where the super absorbent polymer particles 54 are applied to a fiber aggregate 52z downstream of the vacuum roll 106, at substantially the whole or a part of a conveyor line in an application position and after, suction is done from the underside via a sheet 58 and the fiber aggregate 52z, thus allowing the polymers to move further into the fiber aggregate 52z.

Figure 30:
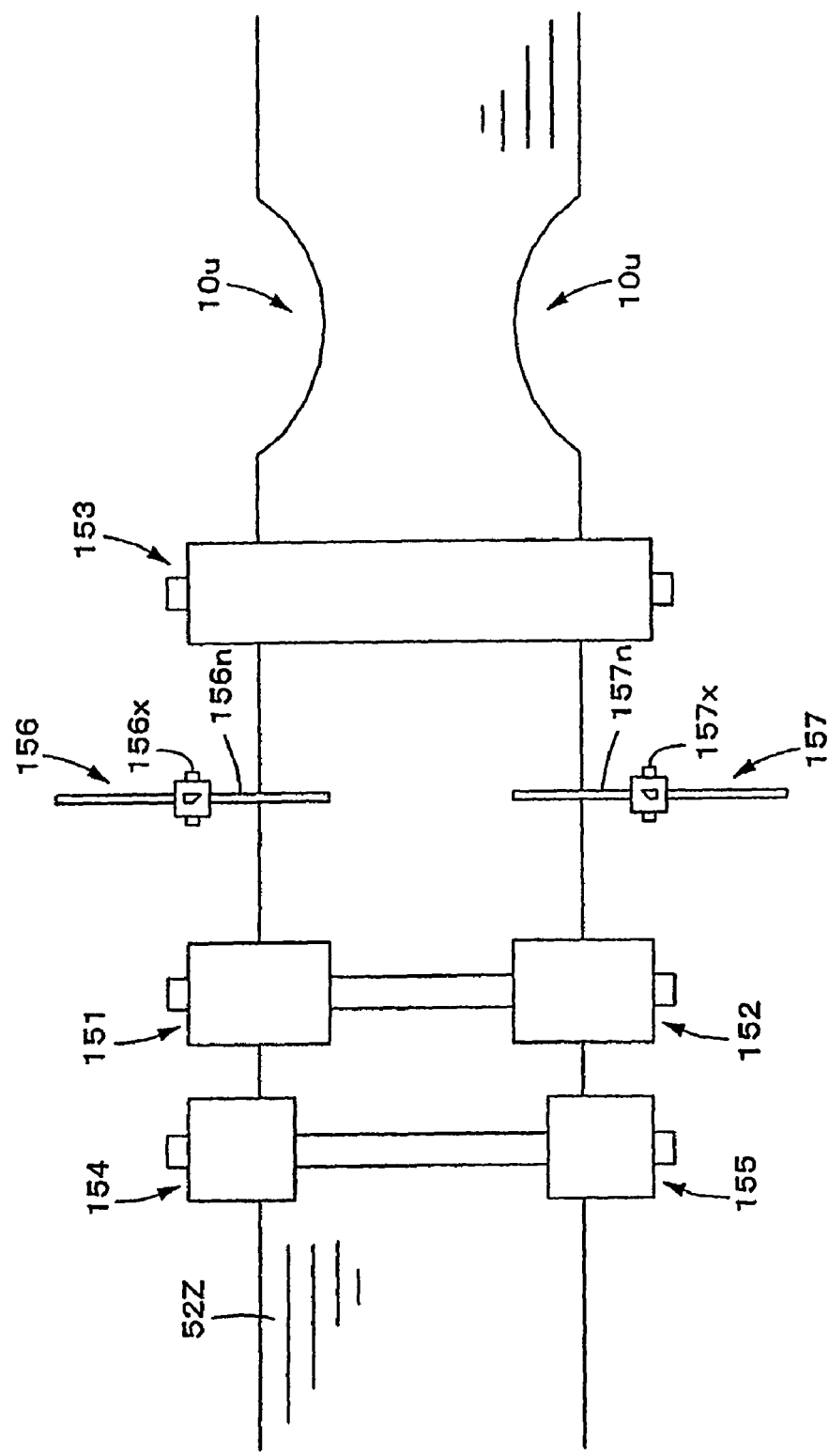
FIG. 30 is a plan view schematically showing an example of absorbent body manufacture facility according to another preferred embodiment.
Figure 31:
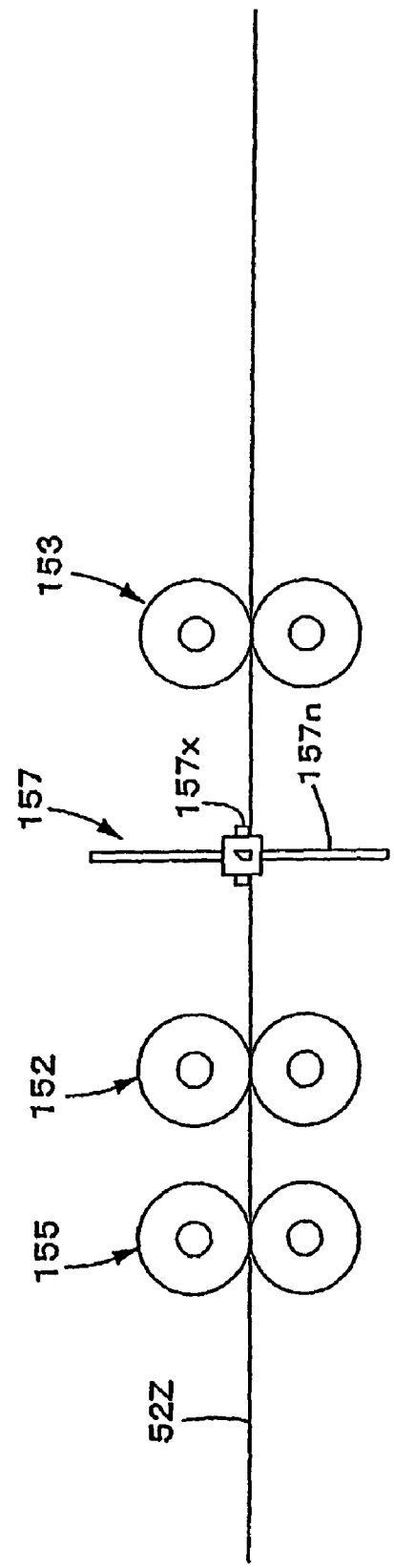
FIG. 31 is a front view schematically showing an example of manufacture facility according to another preferred embodiment.

Next, an example of manufacture facility of an absorbent body according to the present preferred embodiment using a fiber aggregate obtained by the facility shown in FIG. 25 is explained hereinafter. FIG. 30 and FIG. 31 show an example of manufacture facility according to the present preferred embodiment, and the continuous band shaped fiber aggregate 52z made of a tow of desired width and density is supplied. Therefore, this manufacture line is connected directly to the fiber aggregate manufacture line mentioned previously, and the manufactured fiber aggregate 52z can be supplied directly to the manufacture line.

In the present preferred embodiment, in state where expansion force is given along the longitudinal direction to the end in the width direction of the fiber aggregate 52z, a notch is put in the end in the width direction. Therefore, in the illustrated facility example, upstream side nip rolls 151, 152 that pinch the end in the width direction of the fiber aggregate 52z supplied continuously are arranged respectively at both the ends in the width direction of the fiber aggregate 52z, and at further downstream side, downstream side nip roll 153 that pinches the entire width direction of the fiber aggregate 52z is arranged, and by the nip pressure of the upstream nip rolls, the transfer speed of the end in the width direction of the fiber aggregate, between the upstream side nip rolls and the downstream side nip roll, becomes slower than that at the center portion in the width direction. By this speed difference, expansion force is given to the end in the width direction of the fiber aggregate 52z along the longitudinal direction.

The expansion force added to the end in the width direction of the fiber aggregate 52z may be appropriately set by adjusting the nip pressure of the upstream side roll, and in the normal case, when the center portion in the width direction is made as 100%, it is larger than 100% and it is preferable to set it at 300% or below, in particular 200% or below.

Figure 32:
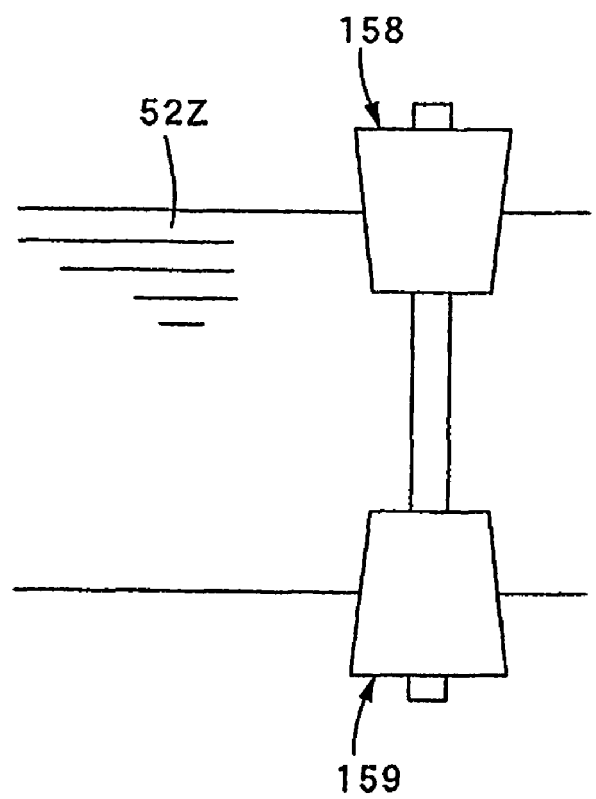
FIG. 32 is a plan view schematically showing an example of another upstream side roll in manufacture facility according to another preferred embodiment.

In order to form a concave portion 10u where the notch width becomes wider toward both the ends like for example V shape, U shape or the like, it is preferable to give the expansion force so as to become larger toward the end edges in the width direction. Therefore, plural stages of upstream side rolls are arranged in the line stream direction (in the illustrated example, nip roll stages shown by reference codes 151, 152, and in roll stages shown by reference codes 154, 155), nipping is made by more nip rolls toward the end edges in the width direction in the fiber aggregate 52z. Further, as shown in FIG. 32, as the upstream side rolls, elastic nip rolls 158, 159 that have a shape where outer diameter becomes larger toward the end in the width direction of the fiber aggregate 52z may be employed.

Further, between the upstream side nip rolls 151, 152, and the downstream side nip roll 153, cutting means 156, 157 are arranged respectively. The cutting means 156, 157 are structured of cutting blades 156n, 157n for putting a notch along the width direction to the end in the width direction of the fiber aggregate 52z, and driving means of the cutting blades not illustrated. In more details, at both the edges of the line (fiber aggregate), rotating shafts 156x, 157x are arranged respectively along MD direction, and the cutting blades 156n, 157n are arranged so as to protrude in the radial direction of the respective rotating shafts 156x, 157x, and when the rotating shafts 156x, 157x are rotated by the driving means not illustrated, the respective cutting blades 156n, 157n that rotated together therewith go from above to below of the end in the width direction of the fiber aggregate 52z and cutting is made. The number of the cutting blades 156n, 157n may be determined appropriately, but in the illustrated example, plural ones are arranged at constant intervals in the rotation direction. And the rotation speed may be adjusted appropriately according to the line speed and intervals of cutting positions.

In manufacture, in the sate where to both the ends in the width direction of the fiber aggregate 52z passing between the upstream side nip rolls 151, 152 and the downstream side nip roll 153, expansion force according to the nip pressure of the upstream side nip rolls 151, 152 is applied, by the cutting means 154, 155, a notch along the width direction is put in the end in the width direction of the fiber aggregate 52z. By this notch, the expansion force added to both the ends in the width direction of the fiber aggregate 52z is released, and portions with notches contract in the longitudinal direction so as to be away from each other, and a concave portion 10u that is concave to the center portion in the width direction is formed at both the ends in the width direction of the fiber aggregate 52z respectively. In this manner, even in the fiber aggregate 52z made of a tow, it is possible to form the concave portion 10u along the leg position in extremely easy manner.

Figure 33:
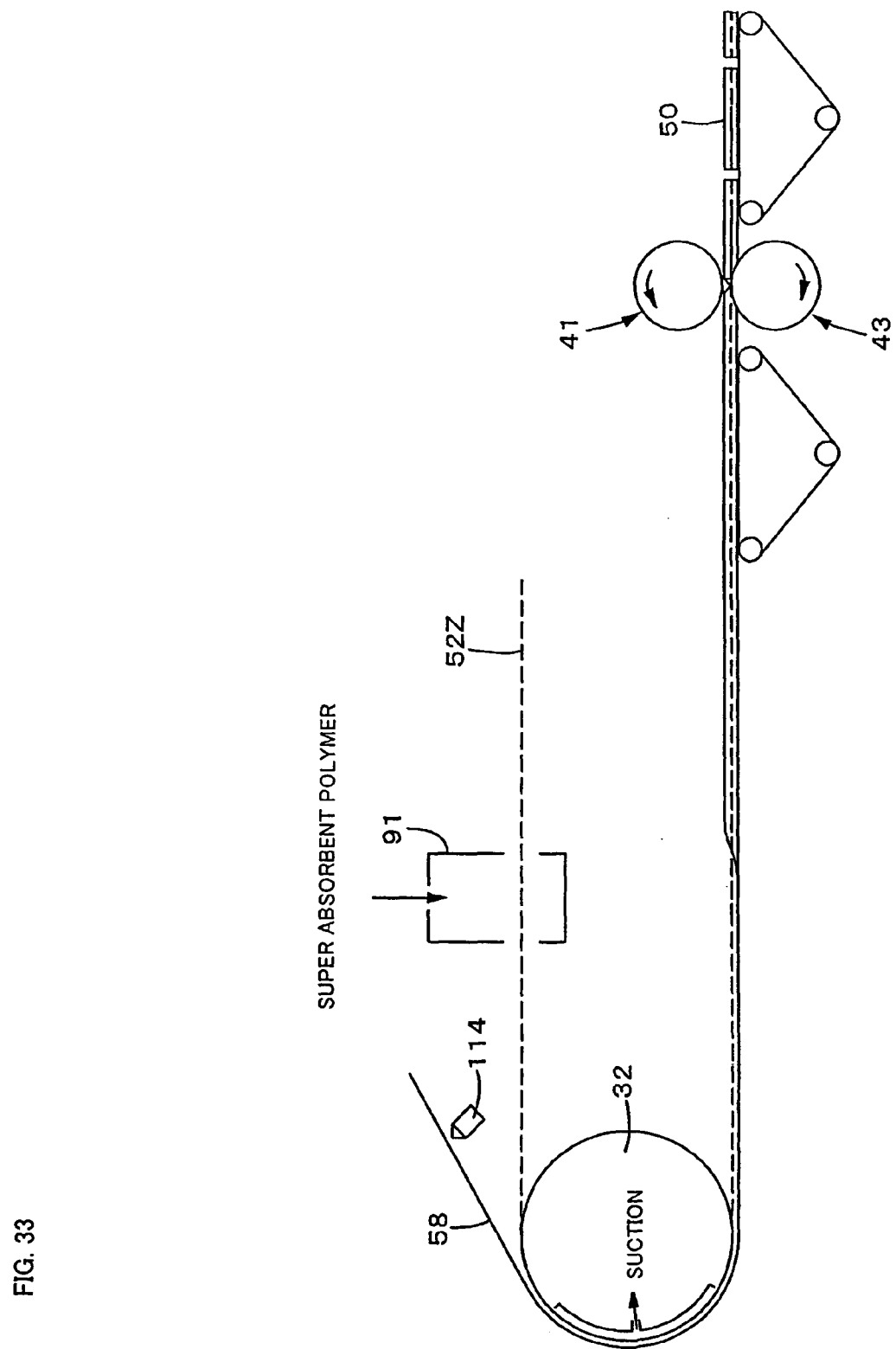
FIG. 33 is a schematic view showing a manufacture flow of absorbent body according to another preferred embodiment.

The fiber aggregate 52z with the concave portion 10u formed therein in this manner is made into individual absorbent body as shown in for example FIG. 33, and then supplied to a product assembly line not illustrated, and can be assembled in as absorbent body of a diaper and a sanitary napkin.

That is, in the example shown in FIG. 33, the fiber aggregate 52z with the concave portion 10u formed therein is sent first to a polymer spray box 91, where super absorbent polymer particles are sprayed onto the upper surface. The spray amount (dispersion quantity) of the super absorbent polymer particles may be determined appropriately according to the absorption amount required for applications of the absorbent body as mentioned previously.

In preferable embodiment, then, the fiber aggregate 52z to which the super absorbent polymer particles have been sprayed is sent to a suction drum 32. The suction drum 32 has an intake hole in outer circumferential wall, and is sucked by suction pump not illustrated from inside over the circumferential specified range (range of roughly left half in the illustrated example). The fiber aggregate to which the super absorbent polymer particles have been sprayed is contacted outer circumferential surface and guided by the suction drum 32. And, in this process, suction is made from the intake hole of the suction drum 32, and atmosphere is passed from the giving side of the super absorbent polymer particles through the fiber aggregate to the opposite side, and by passing force thereof, the super absorbent polymer particles are moved into the fiber aggregate.

In the illustrated embodiment, the fiber aggregate is wrapped with a sheet, and adhesive is applied to cut portions in the inside of the sheet. After the super absorbent polymer particles are sprayed onto the fiber aggregate 52z, further the covering sheet 58 is put thereon. In the case not to perform suction, a simple method may be adopted where the fiber aggregate is put on the sheet, and the super absorbent polymer particles are sprayed thereon. As this covering sheet 58, crape paper, unwoven fabric, fluid permeable sheet such as punched sheet and the like, fluid impermeable sheet such as polyethylene film and the like may be employed.

Further, an adhesive applicator 114 is arranged in the sheet supply route to the fiber aggregate 52z, and as for the covering sheet 58, adhesive is applied to the surface to become the fiber aggregate 52z side by the adhesive applicator 114, and set to the upper surface of the fiber aggregate 52z. As the adhesive, adhesive made of thermoplastic resin (concrete example as mentioned above) may be used preferably.

Figure 34:
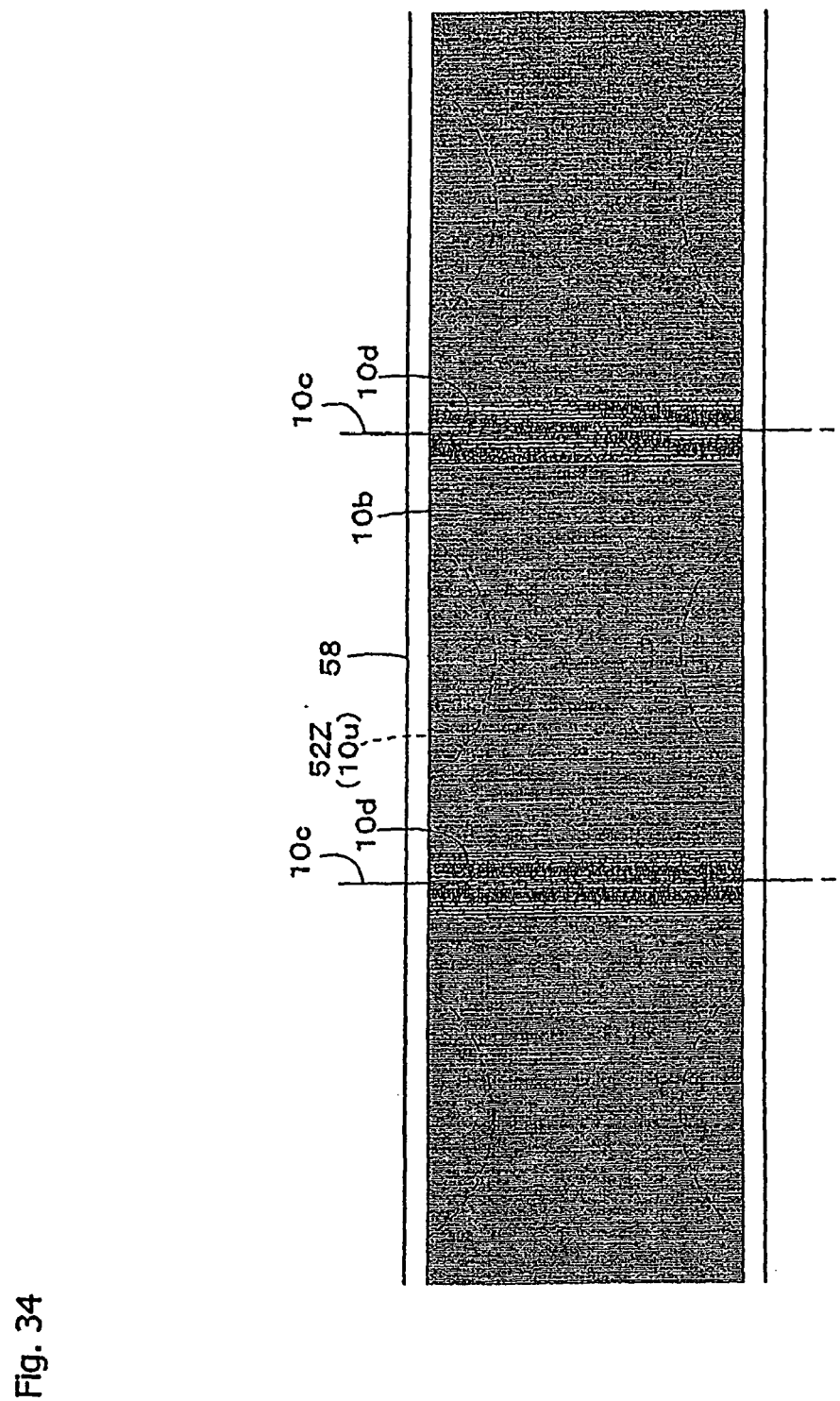
FIG. 34 is a plan view schematically showing an example of adhesive application to a sheet.
Figure 35:
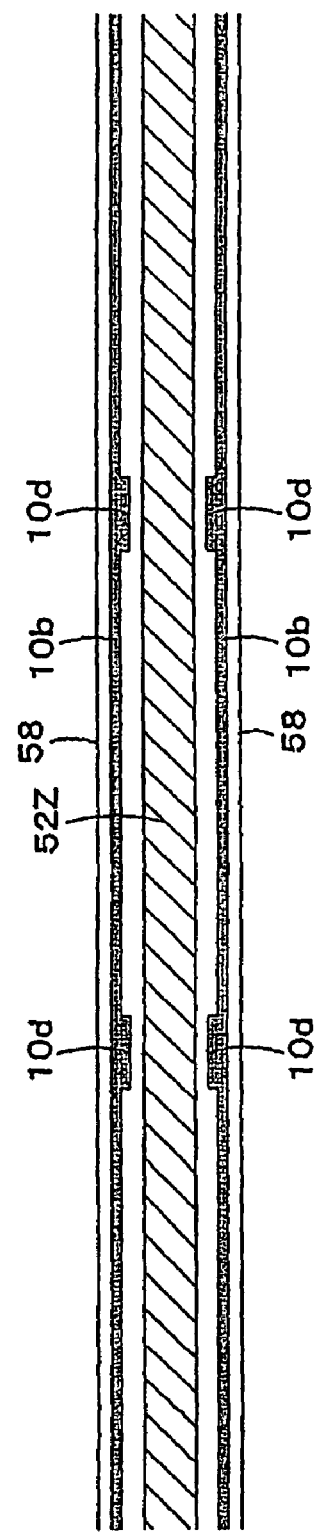
FIG. 35 is a vertical cross sectional view schematically showing an example of adhesive application to a sheet.

This adhesive is, in the illustrated embodiment, applied to at least the range including portions to be cut (cut schedule portions) for making absorbent body individual. This application amount is 2 g/m² or higher, preferably 5 g/m² or higher for increasing the securement of pressure bonding to be described later herein. The adhesive may be applied to part including the cut schedule portions, that is, may be applied intermittently in MD direction, but also may be applied on continuous plane. In this case, the super absorbent polymer exposing on the surface of the fiber aggregate 52z is fixed via the adhesive to the covering sheet 58. From viewpoints of the securement of pressure bonding and the fixation of super absorbent polymer, as shown in FIG. 34 and FIG. 35, it is preferable that adhesive 10b is applied continuously in MD direction, and the application amount of only the cut portion 10c is increased. In the figure, to the adhesive increased portion is marked with reference number 10d. In this case, the application amount may be changed in one applicator 114, but it is preferable that applicators for continuous application and intermittent application are arranged together, and adhesive for fixing super absorbent polymer particles is applied continuously by the former, and intermittent application is made to cur schedule portions by the latter.

Further, with regard to the application of the adhesive 10d in the cut schedule portion 10c, it is a preferable embodiment that as shown in FIG. 36(a), the adhesive 10d is applied to the cut schedule portion in the inside of the covering sheet 58, with the same application width as the design width of the fiber aggregate 52z to be secured at least, and the fiber aggregate 52z opened in width of this application width or more is adhered via the adhesive 10d to the inside of the covering sheet 58. In this case, after adhesion, as shown in FIG. 36(b), the fiber aggregate 52z will contract, but by restraint work by the adhesive 10d, it will not contract to the application width of the adhesive 10d or below. Accordingly, the dimension stability in the width direction of the fiber aggregate 52z is increased.

Figure 36:
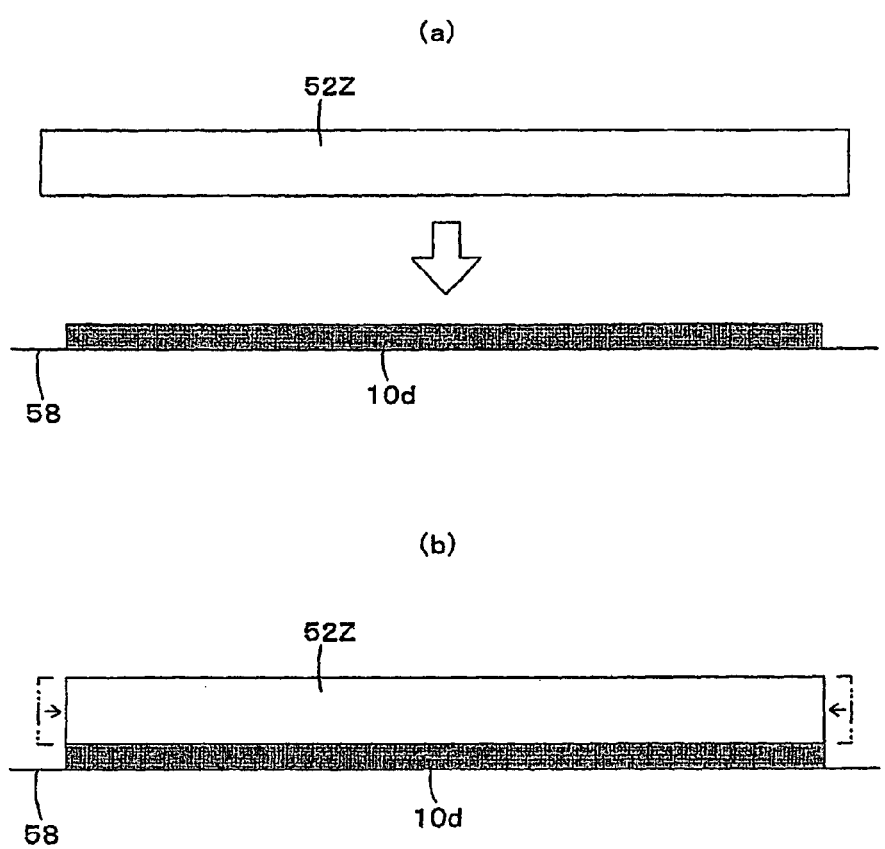
FIG. 36 is a schematic view showing an example of adhesive application to a sheet.

Further, this adhesive 10d, in the example shown in FIG. 36, given to the surface opposite to both the sides in the thickness direction of the fiber aggregate 52z among the inside of the covering sheet 58, however it may be applied only to the surface to become one side in the thickness direction of the fiber aggregate 52z.

On the other hand, the fiber aggregate 52z adhered via the adhesives 10b, 10d to the inside of the covering sheet 58 is, for example, covered with a separate sheet or as shown in the figure both the edges of sheet 58 are folded back by sailor with both the ends of the fiber aggregate 52z running around and covered, and cut at the cut schedule portions sequentially, and made into an individual absorbent body 50 with a specified length.

Figure 37:
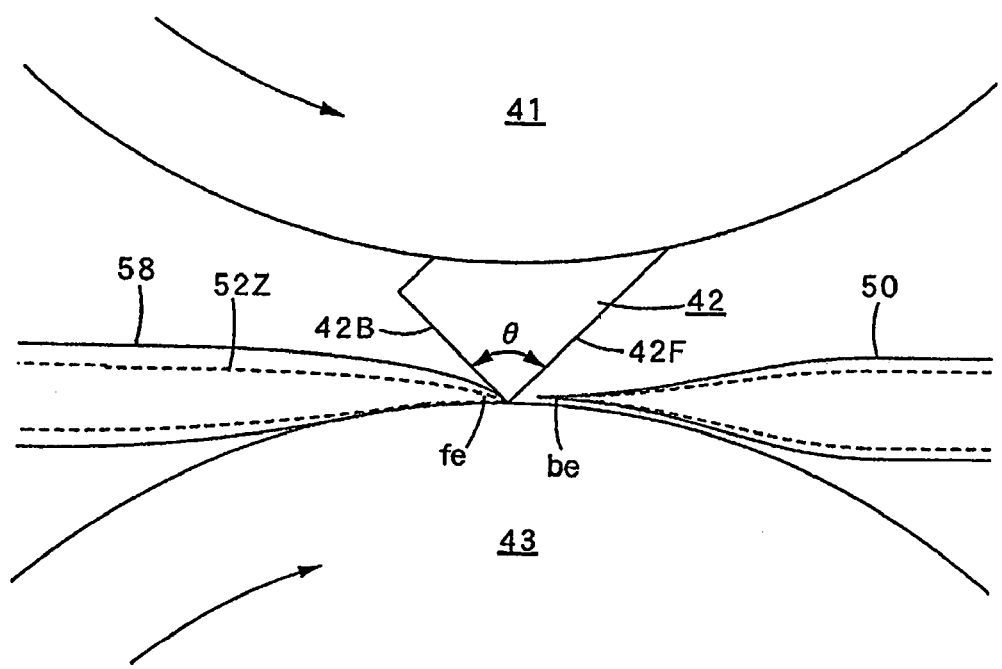
FIG. 37 is an enlarged view of a cutter roll portion.

At this cutting, in especially preferred embodiment, at the same time with cutting, the end portion formed by cutting is pressure bonded. In assumption of the case of continuous process in manufacture line, in concrete as shown in FIG. 33 and FIG. 37, it is preferable to use pressure bonding means that includes a cutter roll 41 where a blade edge 42 expanding along the roll width direction is protruded, and the angle θ between the front surface and the back surface in the rotation direction of the blade edge 42 is 90 degrees or more, and an anvil roll 43 that contacts the blade edge. When the fiber aggregate 52z covered with the covering sheet 58 is made to go between the cutter roll 41 and the anvil roll 43, cutting is made by the blade edge 42 of the cutter roll 41, and downstream side end of individualized absorbent body 50, and upstream side end of absorbent body to be individualized next are formed. And, at the same time with this cutting, downstream side end portion be of individualized absorbent body 50 and upstream side end portion fe of absorbent body to be individualized next are pressure bonded by front surface 42F and back surface 42B in the rotation direction of the blade edge 42.

Figure 38:
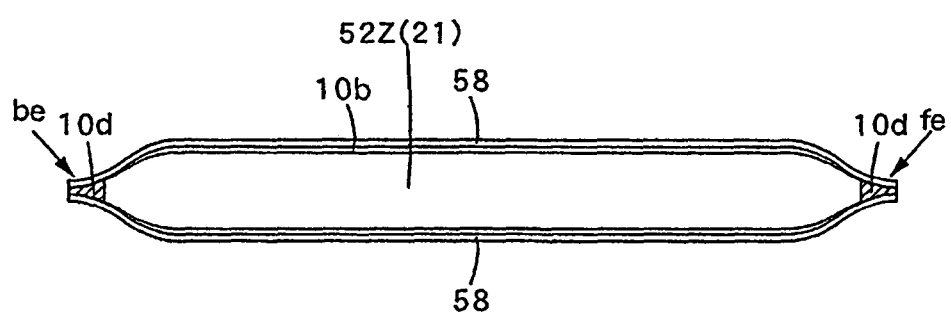
FIG. 38 is a schematic view showing the vertical cross section of an absorbent body.

Thus, as shown in FIG. 38, an absorbent body 50 of the structure where both the ends in the longitudinal direction are formed by cutting, and as for both the end portions fe, be in the longitudinal direction, the fiber aggregate 52z is pinched in the covering sheet 58 and these are pressure sealed by use of adhesive 10d is manufactured.

Figure 39:
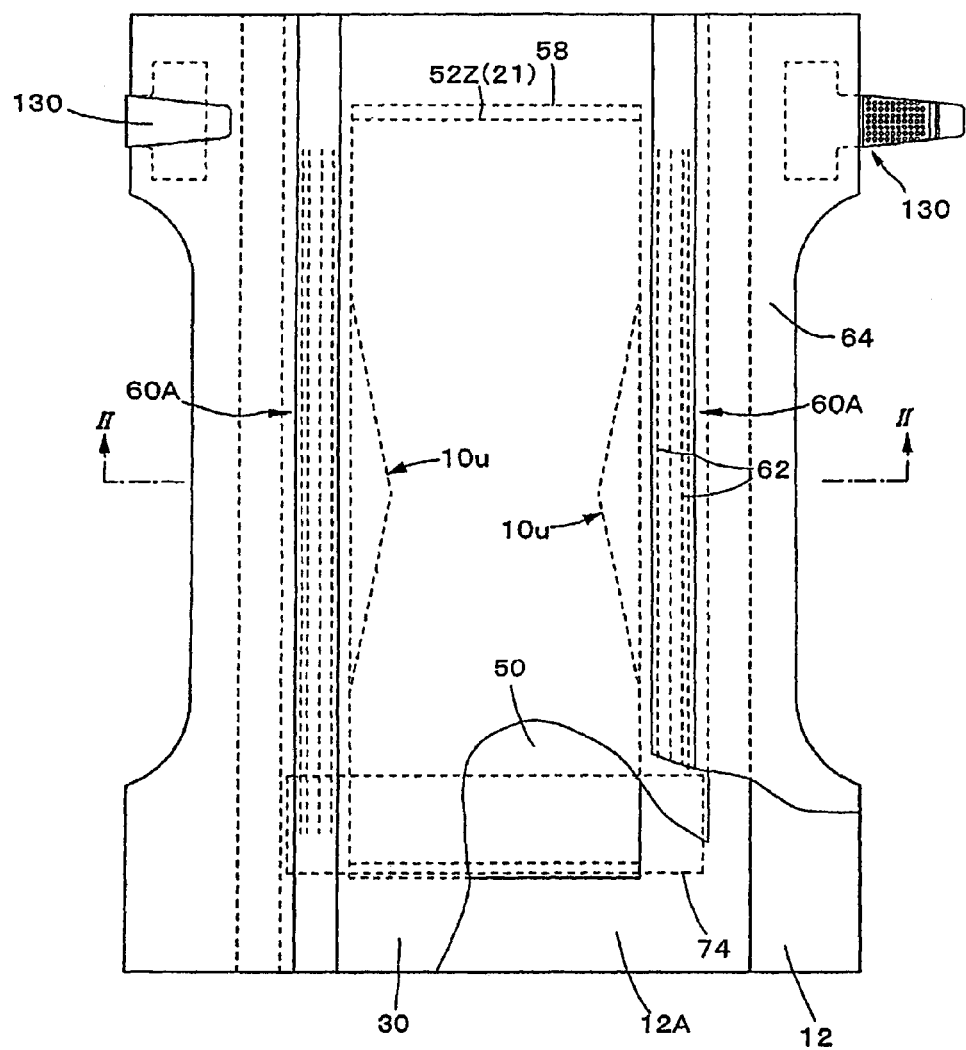
FIG. 39 is a plan view showing a paper diaper in a deployed state.
Figure 40:
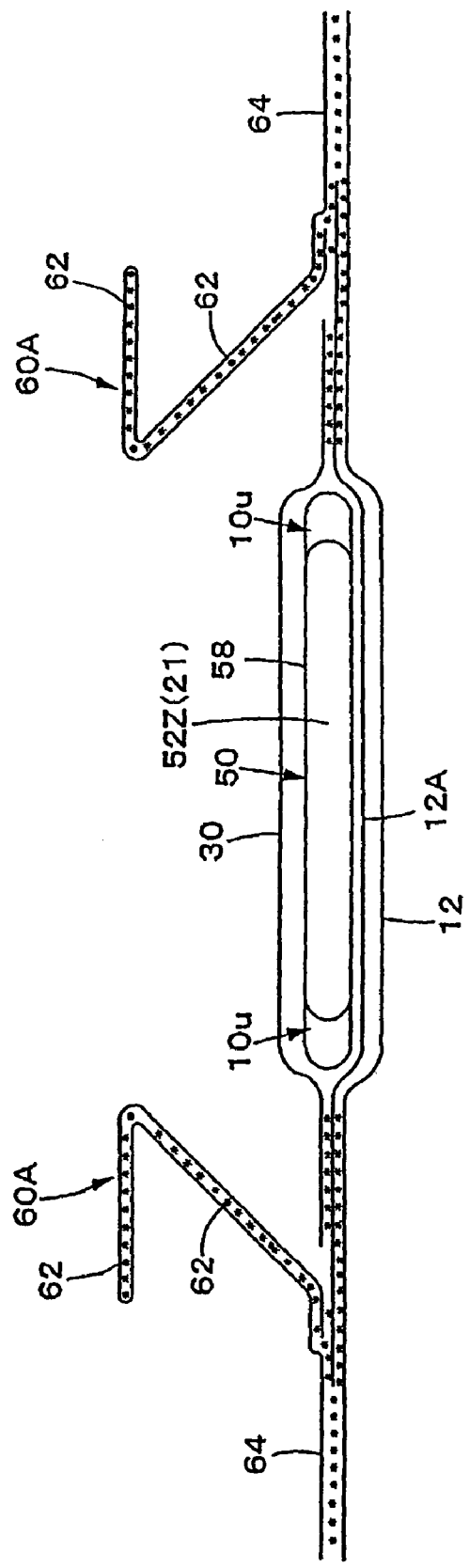
FIG. 40 is a sectional view at II-II line in FIG. 39.

FIG. 39 and FIG. 40 show an example where the absorbent body 50 including the fiber aggregate 52z is applied to a paper diaper, where the absorbent body 50 according to the present invention is arranged between a fluid permeable fluid permeable top sheet 30 positioned at skin side of user, a substantially fluid impermeable fluid impermeable sheet positioned at the outside of product, and a completely fluid impermeable fluid impermeable back sheet 12A made of for example polyethylene and the like.

The absorbent body 50 is equipped with the fiber aggregate 52z made of a tow, where the fiber continuous direction is set so as to be along the longitudinal direction. The fiber aggregate is packaged with a fluid permeable sheet 58 such as crape paper and the like, and super absorbent polymer is filled in the inside of this covering sheet 58. The super absorbent polymer particles may be arranged between the fiber aggregate 52z and the covering sheet 58, and in the fiber aggregate 52z. At both the ends in the width direction at the center in the longitudinal direction in the fiber aggregate, a concave portion 10u that is concave to the center side in the width direction is formed. Such a fiber aggregate 52z may be manufactured by the manufacturing method according to the present invention mentioned previously. The concave portion 10u of the fiber aggregate 52z may be made into U shape as illustrated, V shape and other appropriate shapes. This concave portion shape may be adjusted by appropriately setting expansion force, by use of the manufacturing method according to the present invention mentioned previously.

The back sheet 12A is rectangular and wider than absorber element, and at the outer portion thereof, an outer sheet 12 made of hourglass shaped unwoven fabric is arranged. On the other hand, the fluid permeable top sheet 30 is rectangular and wider than absorber element, and expands slight outer than the side edges of the absorber element, and is fixed to the back sheet 12A by hot melt adhesive and the like (fixation portion concerning the present preferred embodiment including this fixation portion shown by *).

At both the sides of the diaper, leg portion barrier cuffs 60A protruding to user side are formed. The barrier cuffs 60A are structured of a side sheet 64 made of unwoven fabric continuous in substantially width direction, and elastic expanding component, for example elastic expanding components 62 around foot as one made of rubber thread or plural rubber threads as shown in the figure. It is preferable that the side sheet 64 is not fluid permeable but substantially fluid impermeable (semi permeable), and for example, it may be water repellent by silicon processing to unwoven fabric.

At putting on a diaper, since the diaper is put on to the body in form of boat, and contraction force of respective elastic expanding components 62, 62, . . . , works, at leg portion, the barrier cuffs 60A stand up by contraction force of the respective elastic expanding components 62, 62, . . . . Space surrounded by standup portion forms space to entangle body fluid such as urine or the like. Body fluid discharged into this space is absorbed into the absorbent body 50 via the top sheet 30, and the standup portion of the barrier cuffs 60A becomes barrier, and leakage of body fluid from both the sides is prevented.

The paper diaper of the illustrated embodiment has a belly side portion and a back side portion, and stopper pieces 130 are arranged at both the side ends in part of either the belly side portion or the back side portion (back side in the illustrated example), and the stopper piece 130 at one part is engaged to other part (target tape 74 at the belly side in the illustrated example), thereby a belly portion opening portion and a pair of leg portion opening portions are formed. It is so-called a tape fixing type paper diaper, but it is needless to say that the present invention may be applied also to a pants type paper diaper where both the side ends of belly side and back side are jointed beforehand, and other body fluid absorbent articles.

On the other hand, in the present preferred embodiment too, in the same manner as in the preferred embodiment shown in FIG. 18(*a*) and FIG. 18(*b*), it is preferable to arrange the fiber aggregate so that the fiber continuous direction of the tow thereof should be along the longitudinal direction (anteroposterior direction) of the product, however, it may be arranged so that the fiber continuous direction of the tow thereof should be along the width direction of the product as in the preferred embodiment shown in FIG. 18(*c*) and FIG. 18(*d*).

Figure 41:
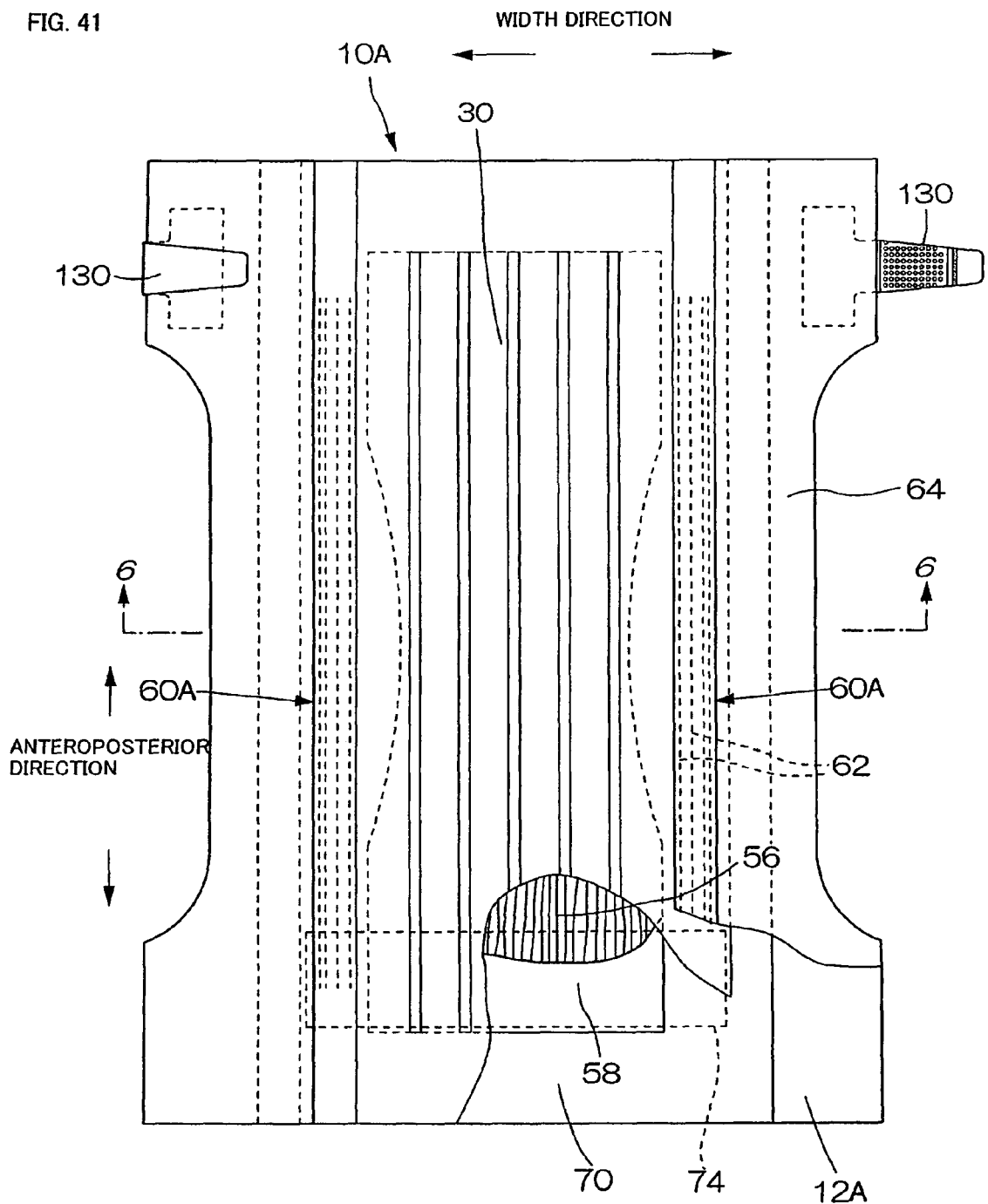
FIG. 41 is a plan view showing a paper diaper in a deployed state.
Figure 42:
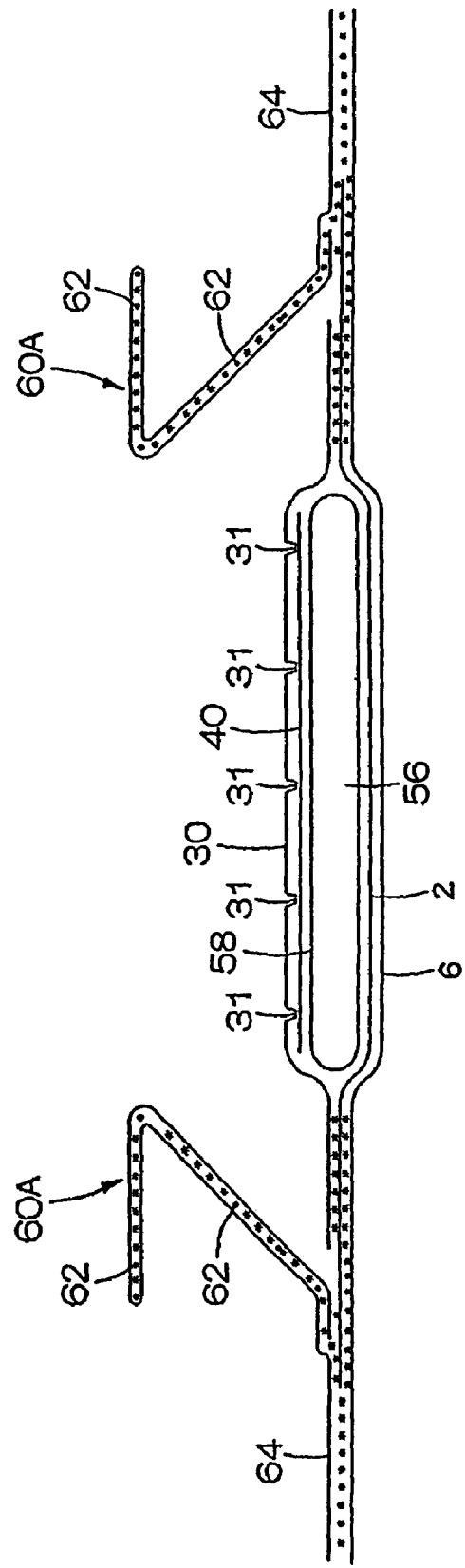
FIG. 42 is a sectional view at II-II line in FIG. 41.

As shown in FIG. 41 and FIG. 42, in order to improve the fluid dispersion, a slot 31 in a continuous line shape may be arranged in one or tow or more, or all of the layers arranged at the front surface side of the absorber core 56, that is, the top sheet 30, the intermediate sheet 40, and the covering sheet 58. When the slot 31 is arranged in the top sheet 30, it is advantageous in that body fluid can be dispersed in earlier stage. Further, when the slot is arranged in the intermediate sheet 40 or the covering sheet 58, it is advantageous in that fluid can be dispersed in a position farther from the skin, and the wet sense can be eased. In consideration of the balance between easy manufacture and effects, it is preferable to arrange the slot 31 in only the top sheet 30 or the intermediate sheet 40, or in both the sheets 30, 40.

The embodiment of the slot 31 may be determined appropriately in consideration of mainly the dispersion direction of body fluid, and for example, the following embodiments may be adopted:

(1) Embodiment where the slot 31 is arranged along the anteroposterior direction of the product as shown in FIG. 41

Figure 43:
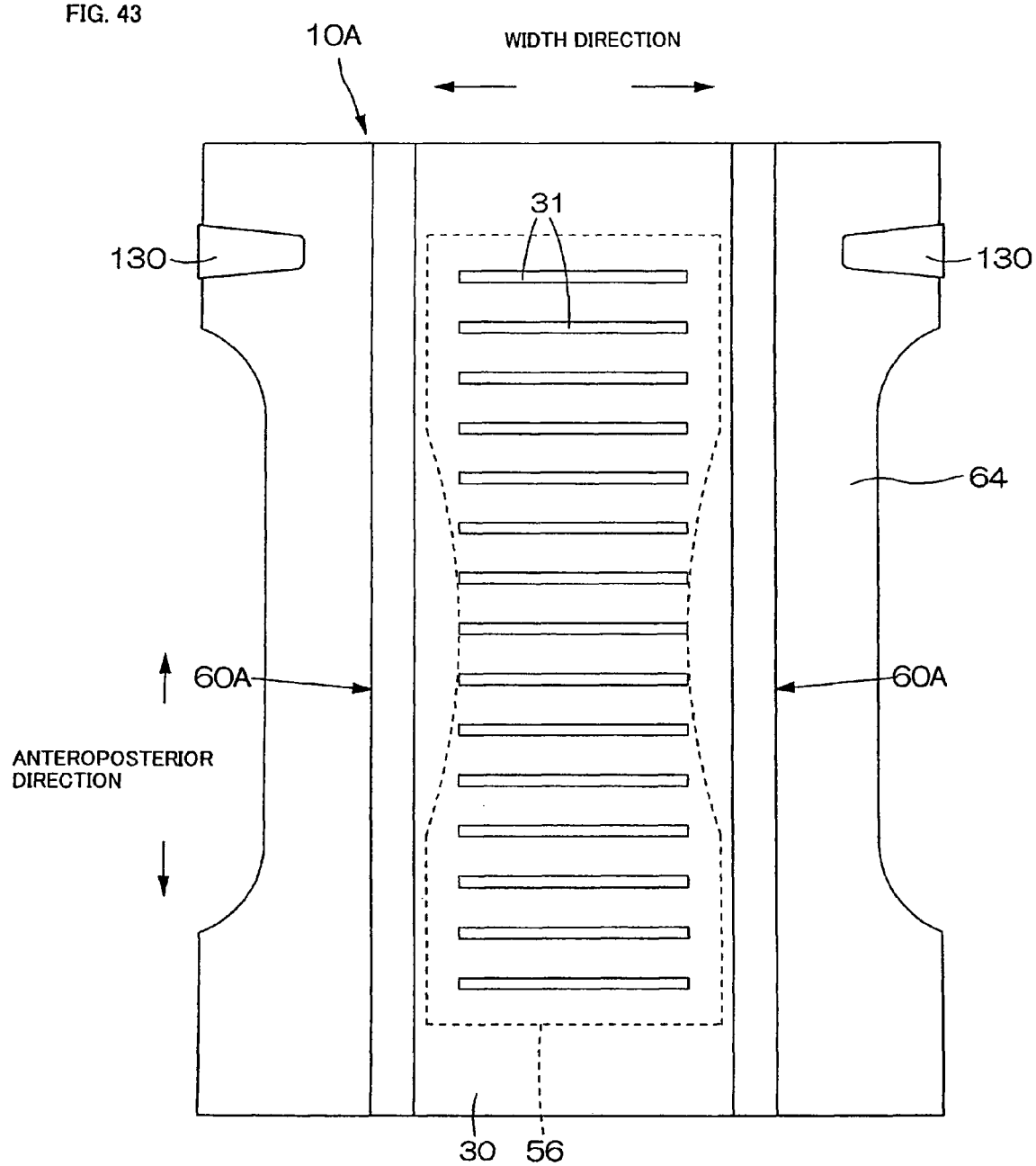
FIG. 43 is a plan view showing another example of a paper diaper.

(2) Embodiment where the slot 31 is arranged along the width direction of the product as shown in FIG. 43

(3) Embodiment where plural slots 31 are arranged at appropriate intervals as shown in FIG. 41 and FIG. 42

Figure 44:
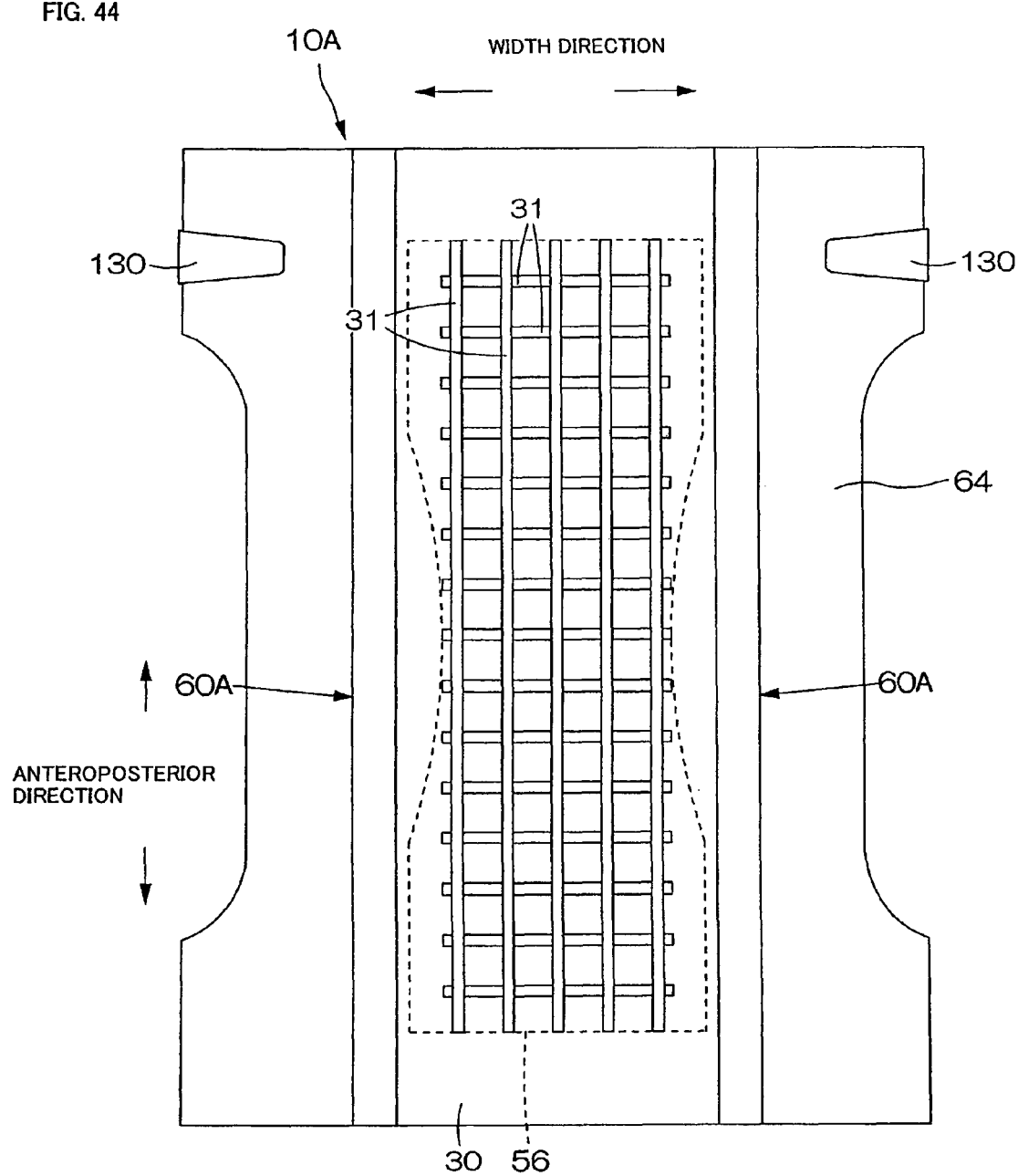
FIG. 44 is a plan view showing still another example of a paper diaper.

(4) Embodiment where plural slots 31 along the anteroposterior direction of the product and plural slots 31 along the width direction of the product are arranged to intersect mutually as shown in FIG. 44 (that is, embodiment where the slots 31 are arranged in a reticular pattern)

Figure 45:
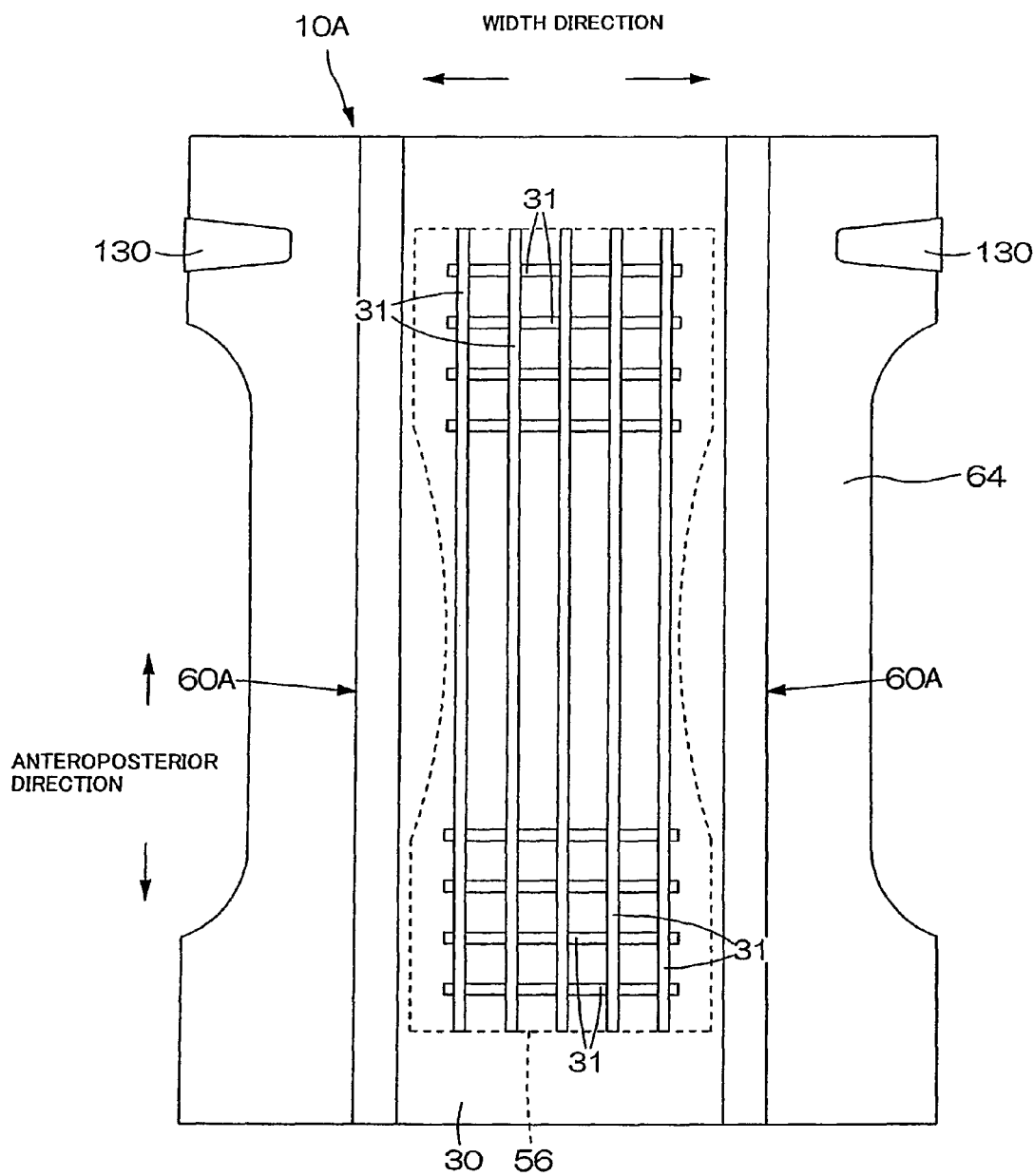
FIG. 45 is a plan view showing further still another example of paper diaper.

(5) Embodiment where plural slots 31 are arranged along the anteroposterior direction of the product, and a slot 31 along the width direction of the product is arranged in only the anteroposterior sides of the products as shown in FIG. 45

Figure 46:
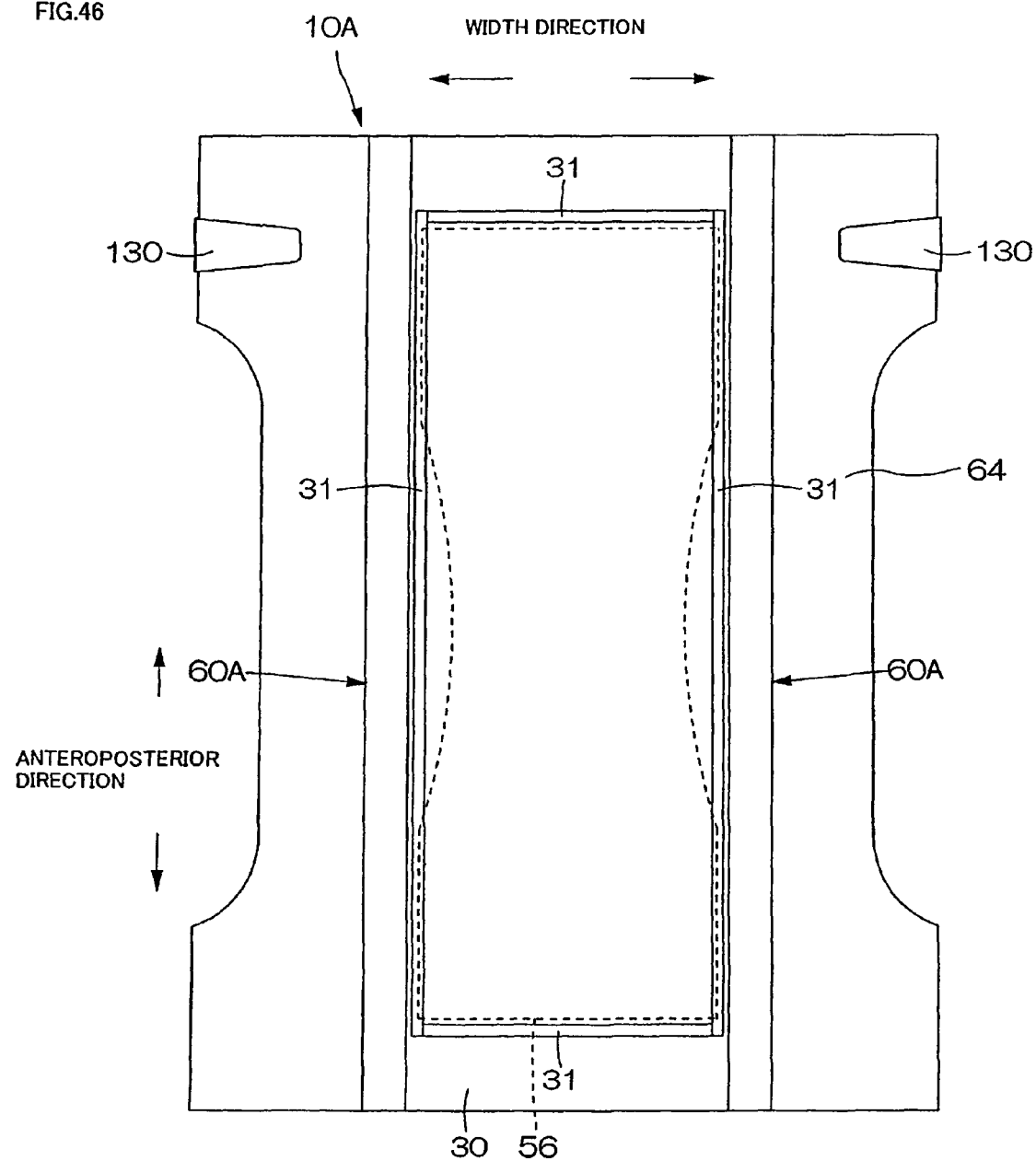
FIG. 46 is a plan view showing still another example of a paper diaper.

(6) Embodiment where the slot 31 is arranged in form of a ring to entangle the excretion position as shown in FIG. 46

The range of the slot 31 arrangement may be determined appropriately in consideration of the dispersion range of body fluid, and for example, the following embodiments maybe adopted.

(a) Entire range or roughly entire range of the objective sheet (for example, 800 or more by area ratio)

Figure 47:
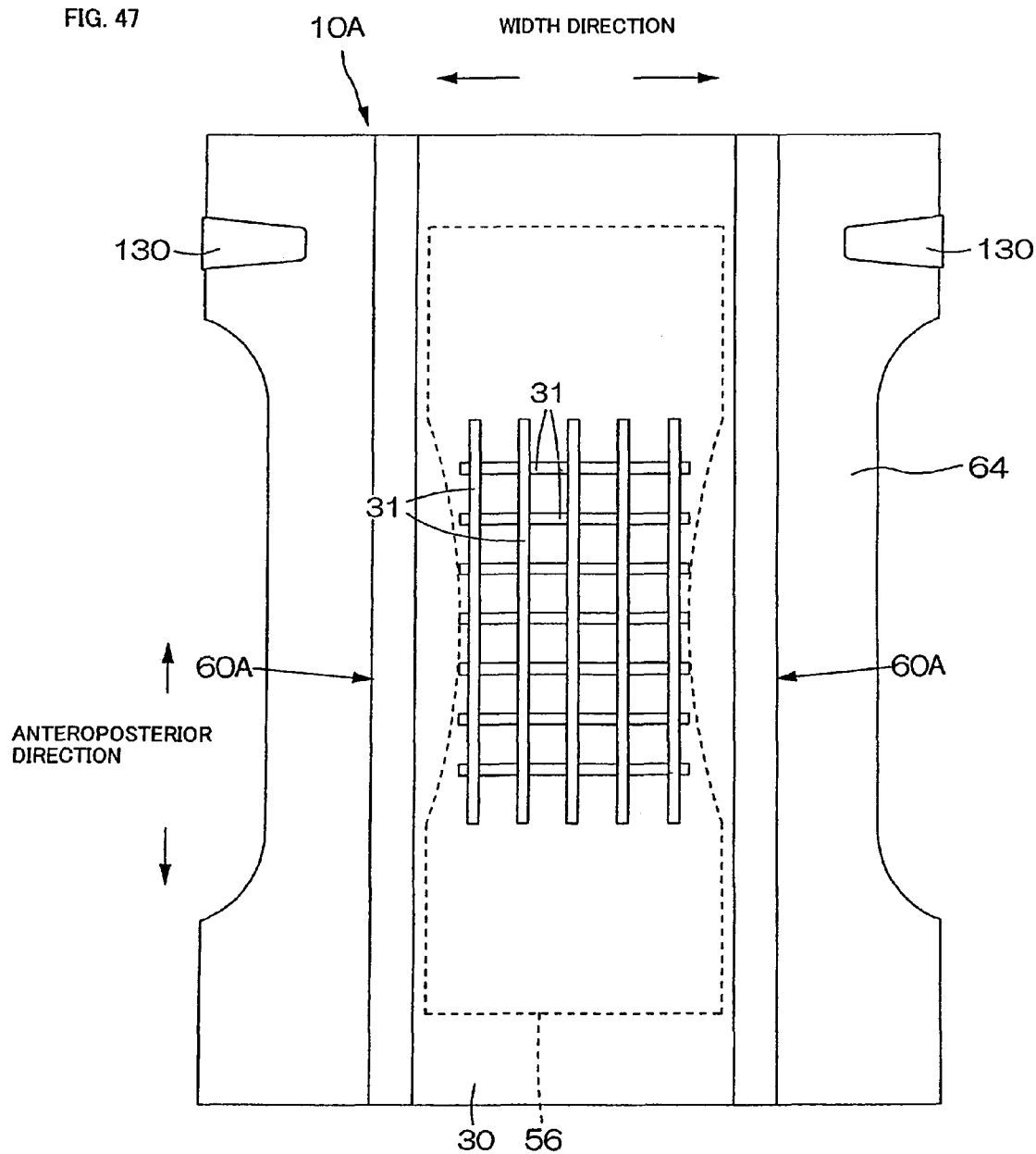
FIG. 47 is a plan view showing further still another example of paper diaper.

(b) Part of the objective sheet, for example only the center portion in the anteroposterior direction of the product or the width direction or only both the ends, as shown in FIG. 47

(c) Range to overlap at least the absorbent body 3, as shown in FIG. 41 and the like The number of the slot 31 may be determined appropriately, and one slot may be all right, however, it is preferable to arrange plural ones, especially three or more, in particular it is preferable to arrange three slots or more along the anteroposterior direction of the product.

The length, width, depth of the slot 31, and the interval in the case of arrangement of plural slots may be determined appropriately. These dimensions cannot be determined in uniform manner, but for normal embodiments of a paper diaper and a sanitary napkin, the length of the slot 31 is preferably 50 mm-1000 mm, and further preferably 70 mm-700 mm. And, the width of the slot 31 is preferably 0.5 mm-50 mm, and further preferably 1 mm-20 mm. Further, the depth of the slot 31 is preferably 0.05 mm-10 mm, and further preferably 0.1 mm-5 mm. Furthermore, the interval of the slots 31 is preferably 0.5 mm-150 mm, and further preferably 1 mm-50 mm.

Figure 48:
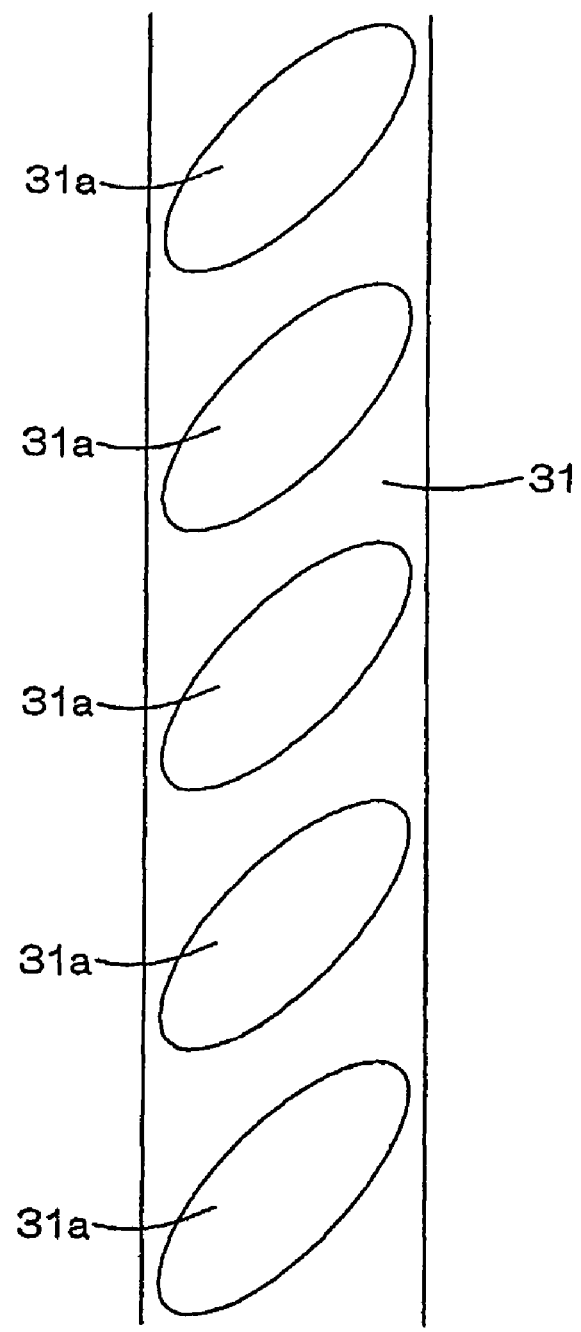
FIG. 48 is a plan view showing an example of a slot by compression processing.

The slot 31 may be formed by manufacturing a raw material itself so as to have the slot 31 (for example, manufacturing it in a cross sectional wave shape or the like), but it is preferable to form the slot by performing compression processing such as emboss processing or the like to objective component in an appropriate process. In this case, the slot 31 may be formed in a continuous line pattern, or as shown in FIG. 48, a pattern of many repeated compression portions 31*a* in spot shape may be adopted, and the compression portions 31a come to close mutually, and thereby continuous like shape slot 31 may be formed.

In the case where slots 31 are arranged in plural sheets, shapes of the slots 31 may be made different. For example, in the top sheet 30, the slot 31 may be expanded in the anteroposterior direction of the product, and in the intermediate sheet 40, the slot 31 may be expanded in the width direction.

Next, other preferred embodiments are explained in details on the basis of the example applied to a tape stopper type paper diaper, however it is needless to say that the present invention may be applied also to a pants type paper diaper, a sanitary napkin, and other body fluid absorbent articles.

Figure 49:
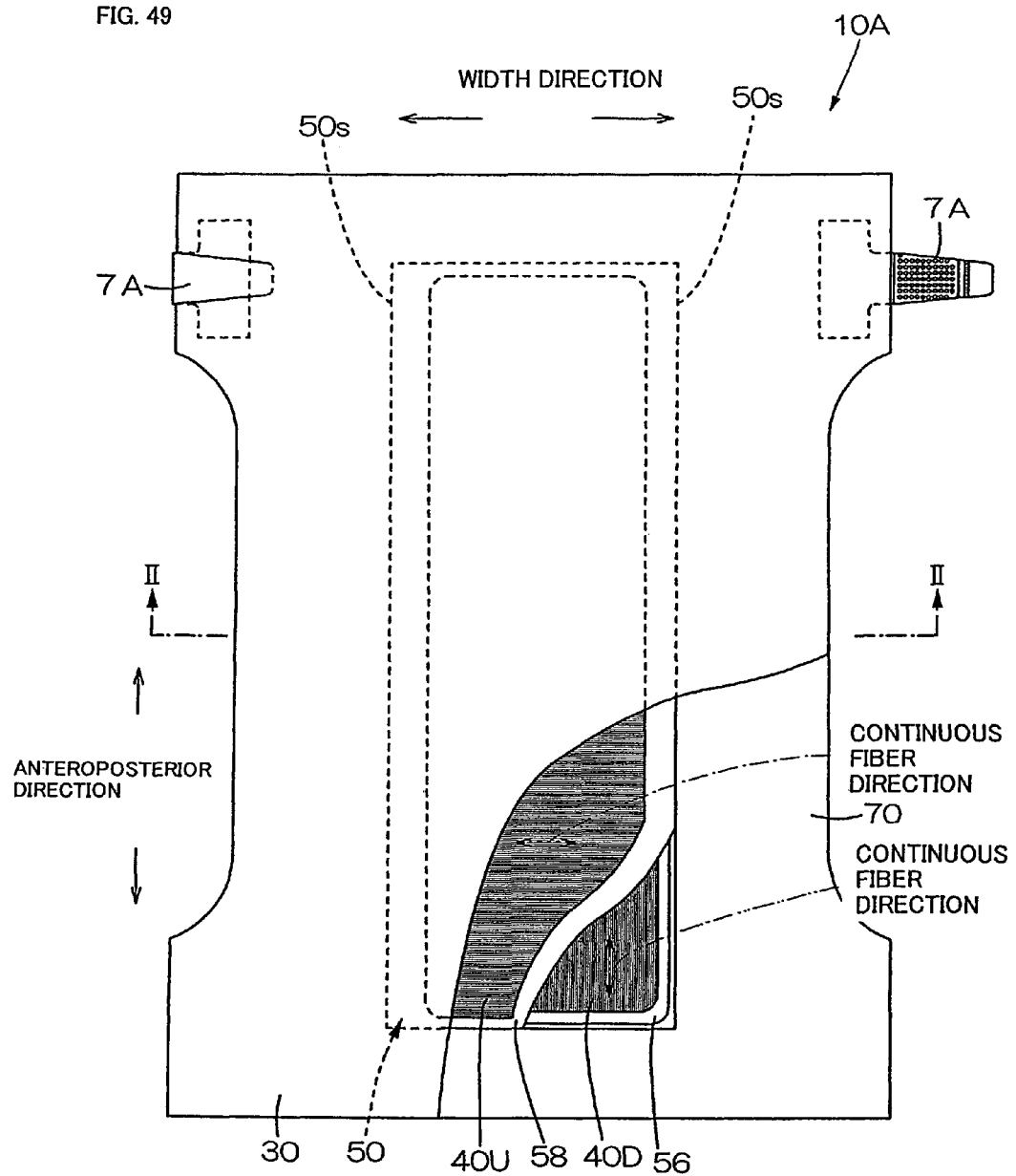
FIG. 49 is a plan view showing a stopper type diaper according to another preferred embodiment.
Figure 50:
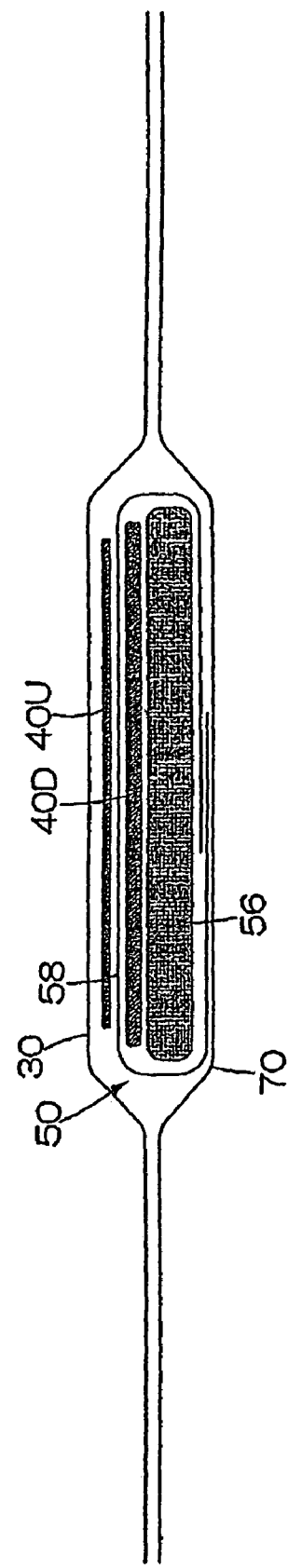
FIG. 50 is a cross sectional view at II-II line in FIG. 49.

FIG. 49 and FIG. 50 show a tape stopper type paper diaper 10A as an objective of the present invention. In this paper diaper 10A, between the fluid permeable front surface (top) sheet 30 positioned to the skin side of user, and a fluid impermeable back surface sheet 70 that is position in the outside of the product, and is substantially fluid impermeable, an absorbent body 50 that is for example rectangular or preferably hourglass and has a certain degree of rigidity is arranged.

The back surface sheet 70 is rectangular and wider than the absorbent body 50. At the outer portion thereof, an outer sheet made of unwoven fabric or the like may be arranged for improving feeling. The back surface sheet 70 may be formed by a plastic film such as a polyethylene film and the like.

On the other hand, the front surface sheet 30 is rectangular and wider than the absorbent body 50, and expands outer than the side edge 50s of the absorbent body 50, and is adhered to the back surface sheet 70 by hot melt adhesive and the like. As the front surface sheet 30, various unwoven fabrics such as span bond unwoven fabric, air through unwoven fabric, SMS unwoven fabric, point bond unwoven fabric and the like, a plastic film such as a polyethylene film and the like, and laminated unwoven fabric where a plastic film and unwoven fabric are laminated may be employed. Further, raw materials of a net shape of plain woven threads such as nylon, polyethylene telephthalate and the like may be employed too.

Between the front surface sheet 30 and the absorbent body 50, for the purpose of swiftly dispersing body fluid passing the front surface sheet 30 to a wide range or swiftly moving it to the absorbent body 50 and so forth, a second (intermediate) sheet 40U is arranged. In a body fluid absorbent body product according to the present preferred embodiment, this second sheet 40U is structured of a fiber aggregate made of a tow (hereinafter, the fiber aggregate as this second sheet is referred to also as second fiber aggregate). This second fiber aggregate is arranged so that the continuous fiber direction should be in the direction along the width direction of body fluid absorbent article, and body fluid reaching the second sheet 40U via the front surface sheet 30 is dispersed in the width direction of a body fluid absorbent article 10A by the second sheet 40U and moved to the absorbent body 50.

In the absorbent body 50, at the side of the front surface sheet 30 of the absorber core 56, a fiber aggregate 40D different from the second sheet 40U is arranged in lamination (hereinafter, the fiber aggregate structuring the absorbent body is referred to also as first fiber aggregate), and these are covered with a fluid permeable sheet 58, for example crape paper, unwoven fabric, punched sheet and the like. The first fiber aggregate 40D, different from the second sheet (second fiber aggregate) 40U, is arranged on the absorber core 56 so that the continuous fiber direction should be in the anteroposterior direction of the body fluid absorbent article 10A. Accordingly, body fluid reaching the first fiber aggregate 40D via the second sheet 40U and the crape paper 58 and the like is dispersed in the anteroposterior direction of the body fluid absorbent article 10A and moved to the absorber core 56 and absorbed and held therein.

That is, in the body fluid absorbent article 10A according to the present preferred embodiment, between the front surface sheet 30 and the absorber core 56, the second fiber aggregate 40U and the first fiber aggregate 40D make a laminated structure, and, the fiber continuous direction of the second fiber aggregate 40U is arranged so as to be along the width direction of the body fluid absorbent article 10A, and the fiber continuous direction of the first fiber aggregate 40D is arranged so as to be along the anteroposterior direction of the body fluid absorbent article 10A. Accordingly, body fluid taken into the body fluid absorbent article via the front surface sheet 30 is first dispersed in the width direction of the body fluid absorbent article 10A by the second sheet 40U, then goes into the crape paper 58 and further is dispersed in the anteroposterior direction by the first fiber aggregate 40D and reaches the absorber core 56. Consequently, it is possible to receive body fluid in the wide range of the absorber core 56, and there is no decline in absorption arising from body fluid being absorbed intensively at a certain portion of the absorber core 56. Further, it is possible to absorb body fluid in every corner of the absorber core 56 laconically.

Herein, the second fiber aggregate 40U as the second sheet and the first fiber aggregate 40D as the absorbent body structural body may be fiber assemblies of a same structure, or the fiber diameter and opening degree thereof may be different. These may be designed appropriately.

On the other hand, in the absorber core 56, super absorbent polymer is inhered. Meanwhile, super absorbent polymer may be inhered in the first fiber aggregate 40D. As the super absorbent polymer, carboxymethyl cellulose, polyacrylic acid and salt thereof, acrylic acid salt polymer bridge, starch—acrylic acid graft copolymer, starch—actylonitryl graft copolymer hydrolysate, poloxyethylene bridge, carboxymethyl cellulose bridge, partially bridged water swelling polymer of polyethylene oxide, polyacryl amid and the like, or copolymer of isobutylene and maleate may be employed preferably. Those to which anti blocking agent is added to restrain blocking due to moisture absorption may be employed too. Further, as the super absorbent polymer, there are various types such as powder, particle, granule, pellet, sol, suspension, gel, film, unwoven fabric and the like, and these may be used in the present preferred embodiment, and especially particles are used preferably.

Meanwhile, though not illustrated, it is needless to say that the art for arranging elastic expanding components such as rubber threads used in absorbent article such as stopper type paper diaper and the like may be employed.

Figure 51:
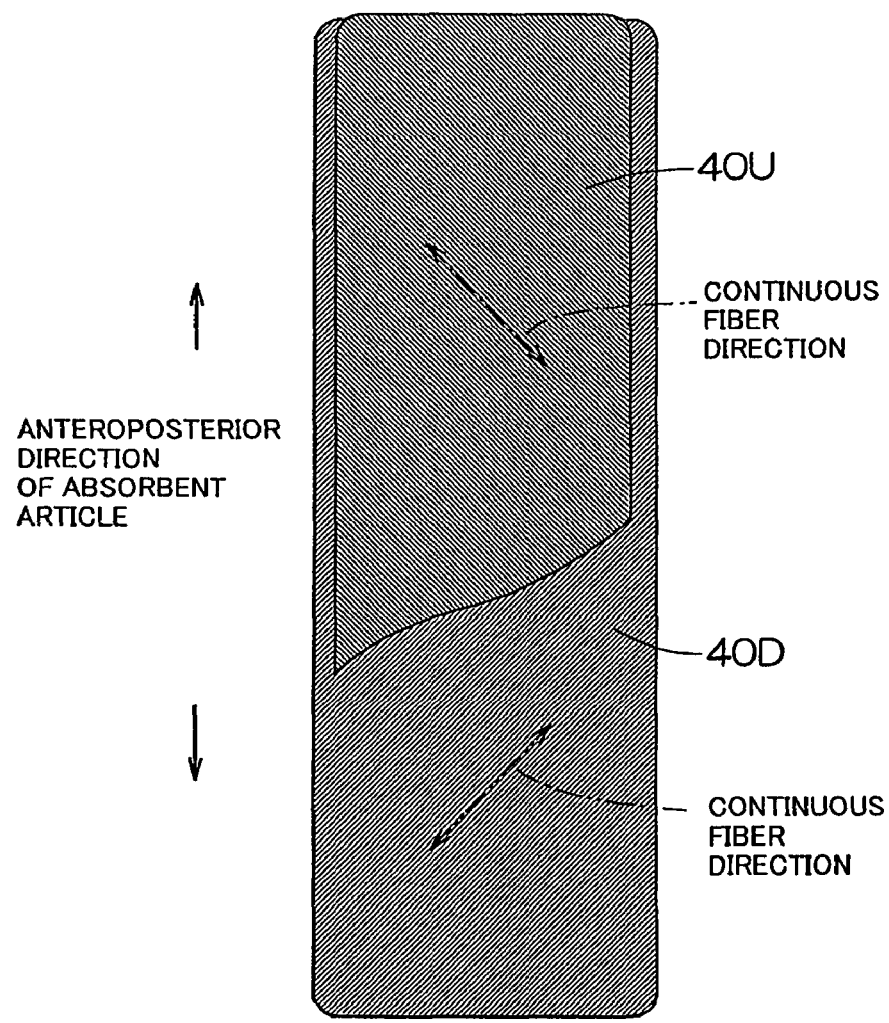
FIG. 51 is a schematic view showing a lamination style of a fiber aggregate layer.

In the above embodiment, shown is the body fluid absorbent article 10A where the respective continuous fiber directions of the second sheet (second fiber aggregate) 40U and the absorber structure (first fiber aggregate) 40D are laminated and arranged so as to roughly cross in the anteroposterior direction, the width direction, but in the present invention, the continuous fiber directions of respective layers are not necessarily to cross. But it is all right if two layers or more of fiber aggregate layers are arranged between the fluid permeable sheet and the absorber core, and the continuous fiber directions thereof are different. For example, as shown in FIG. 51, the second fiber aggregate 40U of the second sheet and the like is arranged so that the continuous fiber direction thereof (chain line in the figure) should have an angle of 45 degrees roughly left diagonally to the anteroposterior direction of absorbent article, and the first fiber aggregate 40D of the absorber structure and the like is arranged so that the continuous fiber direction thereof (two-dot chain line in the figure) should have an angle of 45 degrees roughly right diagonally to the anteroposterior direction of absorbent article, thus a structure where respective fiber assemblies are laminated may be employed. Further, the previous structure is the structure of a body fluid absorbent article equipped with two layers of fiber aggregate layers of the second sheet (second fiber aggregate) 40U and the first fiber aggregate 40D, between the fluid permeable sheet 30 and the absorber core 56, meanwhile, three layers or four layers of fiber aggregate layers may be arranged between the fluid permeable sheet 30 and the absorber core 56.

Figure 52:
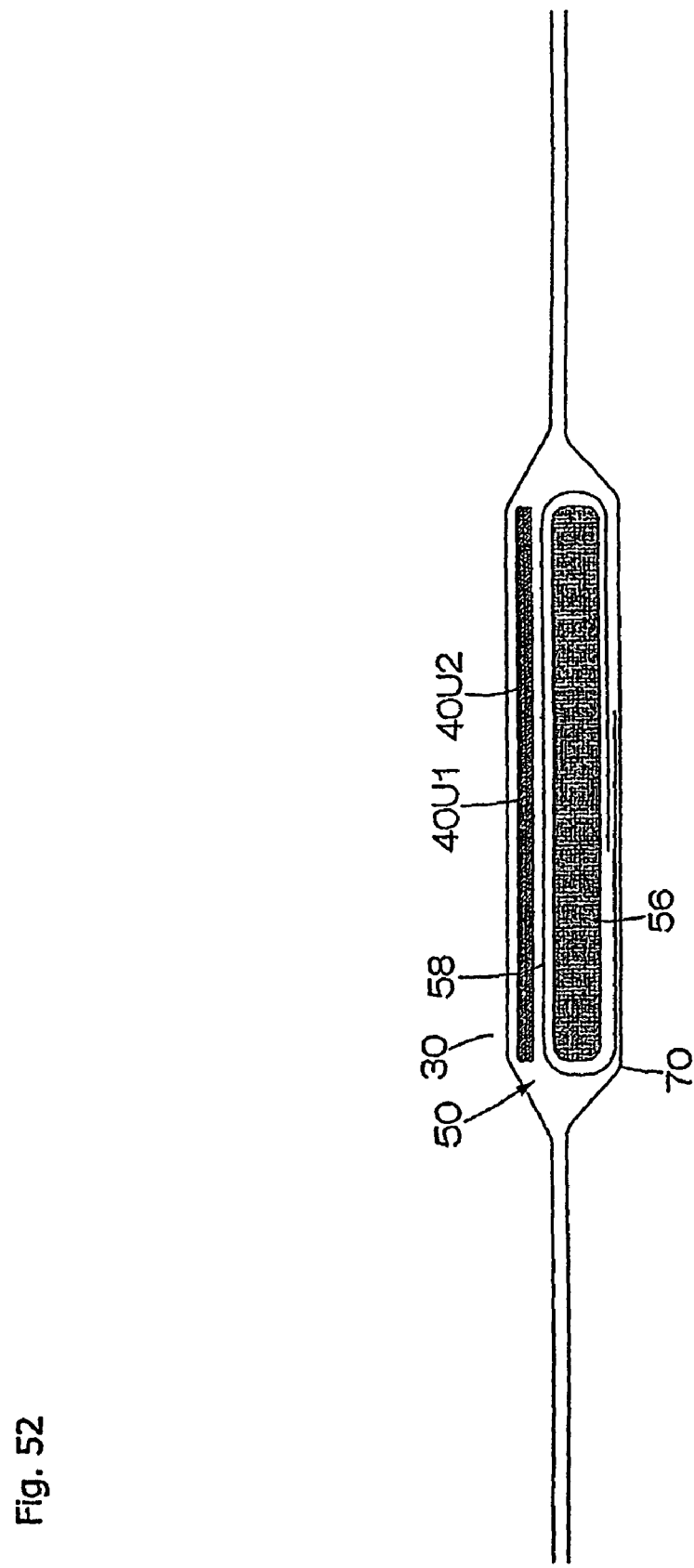
FIG. 52 is a schematic view showing a section of a body fluid absorbent article according to another preferred embodiment.

Further, in the previous structure, two layers of fiber aggregate layers are structured by use of fiber assemblies in the absorbent body structure 40D and the second sheet 40U, as the cross sectional view in FIG. 52, a second sheet 40U where fiber assemblies 40U1, 40U2 of different continuous fiber directions are laminated and arranged may be arranged between the absorbent body 50 and the fluid permeable sheet 30.

Figure 53:
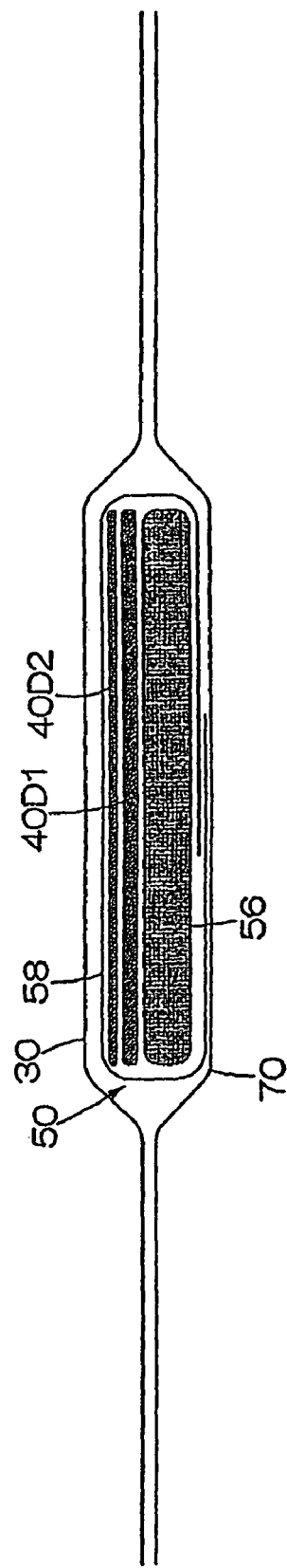
FIG. 53 is a schematic figure showing a section of a body fluid absorbent article according to still another preferred embodiment.

As shown in FIG. 53, an absorbent body 50 where fiber assemblies 40D1, 40D2 of different continuous fiber directions are laminated and arranged may be arranged at the side of the fluid permeable front surface sheet 30 of the absorber core 56. In this structure, though not illustrated, a second sheet may be arranged separately, and as the second sheet in this case, besides the fiber aggregate, no hole or hole opened unwoven fabric, short fiber or long fiber unwoven fabric, mesh shaped film and the like may be employed. When unwoven fabric is used, water retaining fibers such as rayon or cellulose derivative and the like may be included in unwoven fabric, or hydrophilic agent may be added. When unwoven fabric is used, it is preferable that the fiber density is smaller than the fiber density of the front surface sheet 1, for example, those of the fiber density exceeding 2.1 dtex, especially those of the fiber density exceeding 2.1 dtex and 11.0 dtex or below may be used. As the raw material of unwoven fabric used in the second sheet of this embodiment, polypropylene, polyester, polyethylene telephthalate, polyamide, nylon, rayon, vinylon, acryl and the like may be used, and in the case by direct method, those made of polypropylene, polyethylene telephthalate, nylon fiber may be employed preferably. For conjunction of short fibers, by wet method, dry method (air ray method or card method), span lace method and the like, point adhesion by heat or adhesive, crossing by water flow or needle or the like may be employed. Unwoven fabric made of composite fiber of core/shell, side by side structure may be listed up, and as this composite fiber, polyethylene telephthalate/polyethylene, polypropylene/polyethylene, polypropylene/polypropylene and the like may be listed up.

The concrete structure, manufacture method and the like of fiber assemblies (first fiber aggregate and second fiber aggregate) that can be used in the present preferred embodiment are same as those described in the column mentioned above (fiber aggregate), therefore they are omitted herein.

EXAMPLES

1. Experiment 1

Using a fiber aggregate including no super absorbent polymers (basis weight 0.000 g/cm$^2$) and a fiber aggregate of 0.020 g/cm$^2$ of super absorbent polymers, cutting was repeated until the blade of a cutter is nicked. As a result, by cutting at points of not including any super absorbent polymer or hardly including any super absorbent polymer, the product life of a cutter blade was found to lengthen by up to about 30%.

2. Experiment 2

An absorbent body (preferred example A) according to the present invention using a fiber aggregate made of a tow of cellulose acetate fibers, as shown in Table 5, a general absorbent body (conventional example B) using short fiber pulp, and a fiber aggregate made of a tow of cellulose acetate fibers were used, and on an absorbent body that does not satisfy the conditions of the present invention (comparative example C), the following measurements were carried out. Meanwhile, in Table 5, evaluation results are shown too.

In 1 liter beaker provided with a rotor therein, 500.00±0.10 g of 0.9% hydrated chloride of sodium (guaranteed reagent of 9.00 g of sodium chloride was dissolved into 991.0 g of ion-exchange water to be prepared), 2.0000±0.0002 g of sample was added while the solution was being stirred with a magnetic stirrer, and the resultant solution therein was stirred for one hour with the beaker covered with Saran Wrap.

Contents in the beaker were filtered using a standard strainer (38 μm, 200 mmφ×45 mm), gel remained on the strainer was dewatered with Teflon plate and left for 15 minutes. The weight A of the gel remained on the strainer was measured, and the amount of absorption was calculated with the following expression.

$$C = A/S \tag{1}$$

Where: C: saline absorption amount (g/g), A: weight of gel remained on a strainer (g), S: sample weight (g)

The measurement of the amount of water retention of Super absorbent Polymer is conducted in the following way:

0.9% sodium chloride water solution was put into around 80% of a stainless steel container.

2.0000±0.0002 g of sample is precisely weighed, and put into a cotton bag (membrode No. 60 100 mm×200 mm), and approximately 100 ml of 0.9% sodium chloride water solution was poured into the cotton bag, and at the same time, the whole was dipped into the water solution in the stainless steel container.

The upper portion of the cotton bag is bound by a rubber band and is dipped for 15 minutes, and spin dried for a minite by a spin dryer (167G), and the weights of the cotton bag and the gel was measured.

The same operation is carried out without putting in sample, and the weight at moistening of the empty cotton bag is measured. The amount of water retention was calculated with the following expression.

$$C = (A-B)/S \tag{2}$$

Where: C: water retention amount (g/g), A: weight of cotton bag and gel (g), B: weight at moistening of the empty cotton bag (g), S: sample weight (g).

The measurement of the rate of absorption of Super absorbent Polymer is done in the following way:

Into a 100-mililitter beaker with a rotator therein, 50.00±0.01 g of 0.9% sodium chloride water solution was put, and the beaker was kept constant at 25±0.2° C. in a tropical aquarium.

By use of a magnetic stirrer and a rotating body measuring apparatus, the water solution was stirred at rotation rate 600±10 rpm.

2.0000±0.0002 g of sample was precisely weighed, and put into the whirl in the beaker and at the same time, measurement by a stopwatch was started. The time (seconds) after the whirl disappears and until the liquid surface becomes level was recorded, and made the absorption rate.

Figure 28:
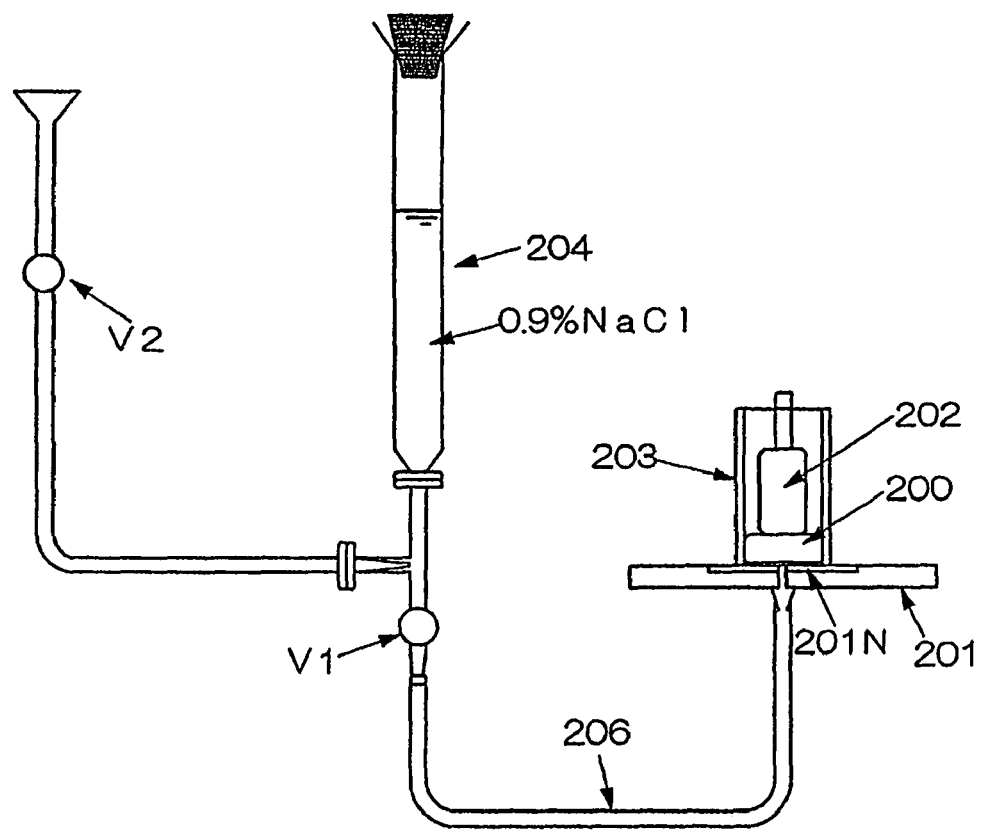
FIG. 28 is an explanatory view showing a tester.

The measurement of the amount of absorption under pressure of super absorbent polymer is done in the following way:

As shown in FIG. 28, a cylinder 203 made of acryl resin (which is 2 cm in inside diameter, 5 cm in height, and in which a nylon net 201N of 75 μm is attached to the bottom) was installed in a standing position with the center thereof aligned with the vertical through hole at the central portion of a support platform 201, 0.100±0.0002 g of sample 200 was put in this cylinder 203, and a cylindrical weight 202 (1.9 cm in diameter, and 120 g in weight) was put on the sample 200.

The outlet of a burette 204 was connected to a lower opening of the through hole of the support platform 201 with a conduit tube 206, and scale values before valves V1 and V2 were opened and scale values after 30 minutes have passed were read.

The amount of absorption under pressure was calculated with the following expression.

$$C=(A-B)/S \quad (3)$$

Where: C: amount of absorption under pressure (ml/g), A: scale value when 30 minutes have passed after the start of water absorption (ml), B: scale value before water absorption (ml), S: sample weight (g)

The measurement of gel strength of super absorbent polymer is done in the following way:

2.0 g of urea, 8.0 g of sodium chloride, 0.3 g of calcium chloride, 0.8 g of magnesium sulfate, 970.9 g of ion-exchange water, and 0.25 g of ferrous sulfate were mixed, to prepare 1 liter of artificial urine in total (50 ppm of iron ion).

49±0.1 g of artificial urine including 50 ppm of iron ion was put in a 100 ml beaker provided with a rotor therein and stirred using a magnetic stirrer. 1.0000±0.0002 g of sample was weighed and put in swirls in the beaker, and thereafter stirred until the swirls are disappeared and the liquid surface comes to be horizontal.

Gel having been produced was left for three hours in a machine at constant temperature and constant moisture of 40° C.×60% RH.

The gel was soaked in a constant-temperature water bath at 25° C. for five minutes, and thereafter gel strength was measured with neo-card meter. This measured values were unit-converted with the following expression, and thus gel strength (Pa) was calculated.

$$C=A\times 0.1 \quad (4)$$

Where: C: gel strength (Pa), A: gel strength obtained from neo-card meter (dyne/cm$^2$), 0.1: constant)

The measurement of the amount of absorption under pressure in diaper state is done in the following way:

First, the weight of sample before absorption was measured.

Figure 29:
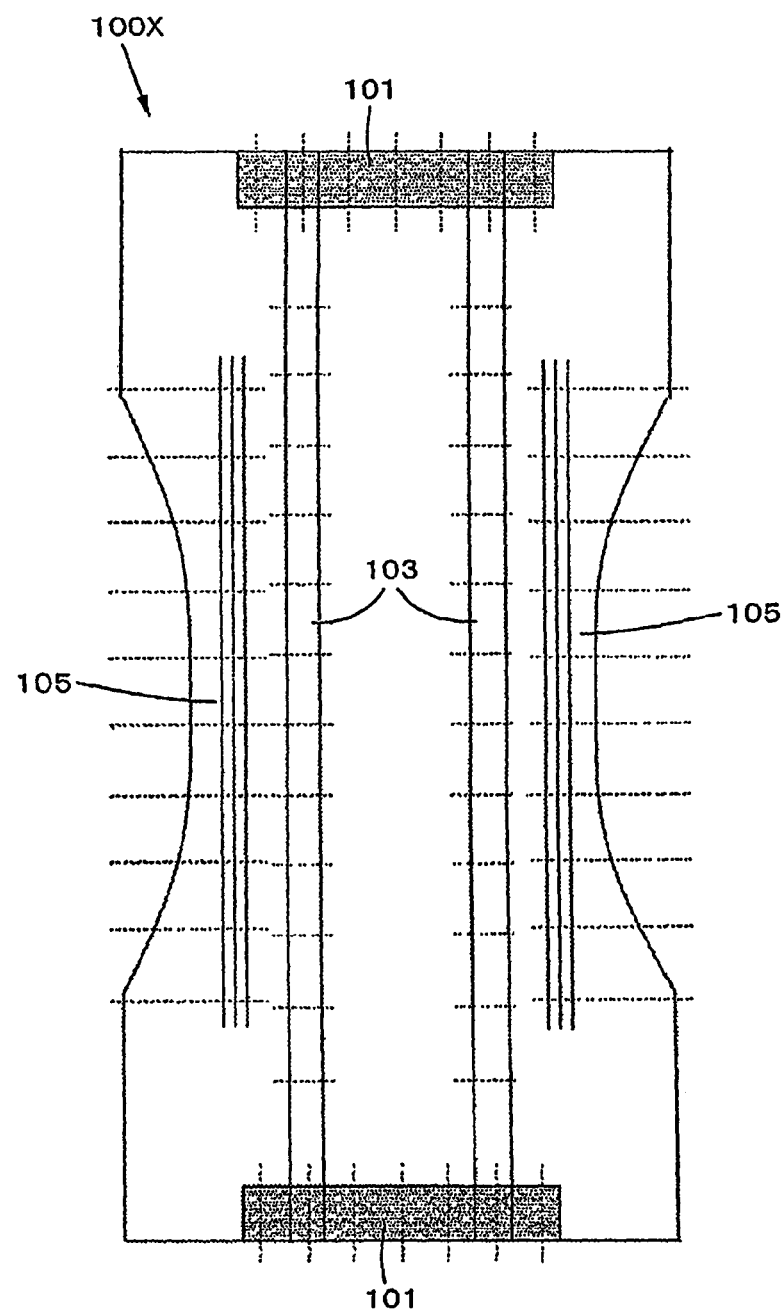
FIG. 29 is a plan view schematically showing a method of measuring the absorption amount under pressure in a diaper state.

Next, as shown in FIG. 29, notches are put in the portion that contracts by rubber threads and the like in a sample diaper 100X, for example, a waist portion 101, a leg portion 105, a gather portion 103, at 2 cm intervals as shown by dot lines, and the diaper is made unforcibly (naturally) flat.

With the use surface (inner surface) upward, the sample was pinched flat between an acrylic plate and a metal plate, and a spindle (10 kg) is put on the acrylic plate, and the sample was dipped in the artificial urine (previously mentioned one) held at 37° C. for 30 minutes.

After 30 minutes, the sample is pulled up from the artificial urine, and after the spindle and the acrylic plate was removed, the sample was folded in three, and put on a scale and the weight was measured.

From the sample weight after absorption, the sample weight before absorption was subtracted and thereby the amount of absorption under pressure (g) was calculated.

The measurement of the rate of absorption in diaper state (Hang method) is done in the following way:

An U-shaped equipment, which is made of an U-shaped plate formed supposing the portion from crotch to hip, and in which there is formed an inlet at the center in a width direction in the lowermost position, was used.

The center position in a longitudinal direction of an absorbent body in a diaper of sample was marked, this marked position was aligned with the inlet, and the sample was fixed to the outer surface of the U-shaped equipment.

The U-shaped equipment to which the sample was fixed was mounted on a hammock, and kept not to be inclined.

A weight (1 kg, 10 cm×10 cm) having a through hole in the center was mounted on the U-shaped equipment. At this time, the through hole of the weight was aligned with the inlet of the U-shaped equipment.

With respect to a sample, 100 cc of artificial urine (that is described above) was injected through the through hole of the weight and the inlet of the U-shaped equipment, and a time period taken to absorb the entire amount of artificial urine was measured to be the rate of absorption (seconds).

The measurement of reversing amount in diaper state is done in the following way:

A top sheet was put on an absorbent body cut in 100 mm×300 mm, and sealed on all sides to be a sample.

A cylindrical equipment of inside diameter of 27 mm (150 mm×150 mm in support part) was put at the center of a sample. The cylindrical equipment was made heavier as necessary.

The artificial urine of the amount of 50 cc was dripped three times at intervals of 10 minutes.

After 10 minutes after the third dripping, a filter paper (ADVANTEC No. 2, 10 cm×10 cm, thirty-ply) was put on, and applied with a load for 10 seconds with a weight of 5 kg. Thereafter, the weight of a kitchen paper was measured, the weight of the kitchen paper having been preliminarily measured into which the artificial urine has not been absorbed was subtracted, and the amount of artificial urine having been moved into the kitchen paper was calculated to be a reversing amount (g).

The measurement of compression resilience RC and compression energy WC is done in the following way:

By use of a compression tester manufactured by Kato Tech Co., Ltd. the sample was compressed under conditions of speed: 0.01 cm/sec, compression area: 2 cm2, sensitivity: 2 (meter 200 g/10 v), compression load: 50 gf/cm2, and from the relative figure of pressure and deformation amount, the compression resilience RC and the compression energy WC was calculated. The high value of the compression resilience RC means that the recovery after compression is high, and the high value of the compression energy WC means that it is easily compressed.

The evaluation of restoring force is done in the following way:

Paper diaper samples were manufactured with using each absorbent body, and so as to be common except for the absorbent body. The ones that are not compressed after manufacturing, and the ones that are compressed in the common embodiment to be packaged, and thereafter the packages are opened were prepared. 20 test subjects made evaluations of restoring forces with visual observation and touch with hands. With regard to the evaluation, with the conventional examples as standard, in comparison with this, the case where change was hardly felt was evaluated as Δ, and the case with high recovery properties and rich flexibility was evaluated as ○.

Table 5

3. Experiment 3

Further, with pant-type paper diapers (first-tenth preferred examples and comparative example 1) equipped with absorbent body manufactured by use of fiber aggregate obtained by opening tow of cellulose diacetate fibers, and general absorbent body and product (conventional example 1-2) using pulp short fibers, the following measurement was carried out. The results are shown in Table 6 and Table 7.

Figure 27:
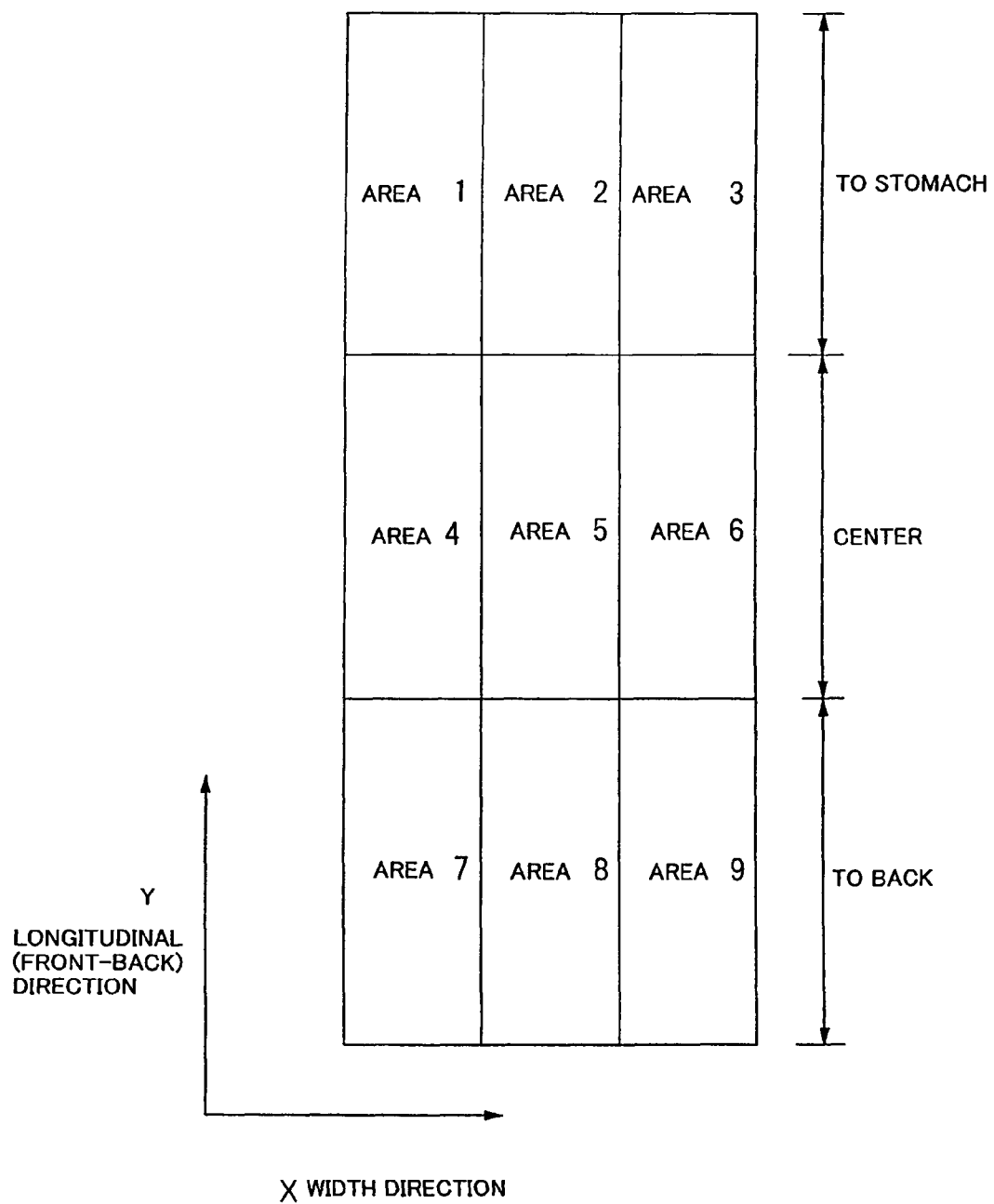
FIG. 27 is a schematic view for explaining directions of an absorbent body.

As to the basis weight of super absorbent polymer particles (SAP), as shown in FIG. 27, the area in a plan view of an absorbent body, being a target is divided into a total of nine areas obtained by being equally divided into three in a width direction and being equally divided into three in a longitudinal direction, and the weights of super absorbent polymer particles with respect to each area are taken as dispersion densities.

Further, in the test method in the table, the items (measurement of the amount of absorption of super absorbent polymer particles), (measurement of the amount absorption under pressure of super absorbent Polymer particles), (measurement of gel strength of super absorbent polymer particles), (measurement of reversing amount in diaper state), and (measurement of the rate of absorption in diaper state), were tested in the same manners as in the test method in the above <Test 2>.

Other test methods are as shown below.

A. Function Evaluation of Restoring Force

Paper diaper samples were manufactured with using each absorbent body, and so as to be common except for the absorbent body. The ones that are not compressed after manufacturing, and the ones that are compressed in the common embodiment to be packaged, and thereafter the packages are opened were prepared. 20 test subjects made evaluations of restoring forces with visual observation and touch with hands. As a result, letting conventional examples a reference, as compared with this reference, the present absorbent bodies were evaluated to have high restoring force and sufficient softness (shown with evaluations of ○ in Tables).

B. Evaluation of Absorption Performance

Dummies (for men and for women) of L size were prepared, in the case where 100 cc of artificial urine was injected at an injection rate of 12.5 cc/minute in each state of laid on its back, and face-down, evaluations were made with the number of times of rolling over until the occurrence of leakage.

Table 6

Table 7

The present invention is preferred for manufacturing an absorbent body in absorbent articles such as paper diapers, sanitary napkins, incontinence pads, and absorbent pads used together with a diaper cover.

The invention claimed is:

1. An absorbent article comprising
a body fluid permeable top sheet,
a body fluid impermeable sheet,
an absorbent body provided between the body fluid permeable top sheet and the body fluid impermeable sheet, and
an exterior sheet of a non-woven fabric provided on a back surface side of the body fluid impermeable sheet,
wherein
the absorbent body includes
a fiber aggregate formed by opening a tow,
an absorbent core having a super absorbent polymer particle retained within the fiber aggregate, and
a covering sheet covering at least a backside and sides of the absorbent core;
the absorbent core has a thickness of 1 to 5 nun;
the fiber aggregate comprises crimped fibers having a fineness of 1 to 16 deniers and a degree of crimps of 15 to 50 numbers per one inch, a fiber basis weight of said fiber aggregate being 0.075 g/cm$^2$ or less;
an amount of water absorption of the super absorbent polymer particle is 50 g/g or higher, and a particle diameter of the super absorbent polymer particle is 20-850 μm;
a basis weight of the super absorbent polymer particle in the absorbent core is 400 g/cm$^2$ or below, and a weight ratio of super absorbent polymer particle/filament in a planer area of 5 cm×5 cm in a region of directly receiving body fluids in the absorbent core is 3 to 9;
a holding sheet is provided, on a backside of the absorbent body, between the absorbent core and the covering sheet, the holding sheet being applied with hot melt adhesives so that the super absorbent polymer particle slipped out of the fiber aggregate is held on the holding sheet via the hot melt adhesives and prevented from moving; and
the holding sheet is composed of non-woven cloth that has a rough surface or fuzzing surface on a top face thereof.

2. The absorbent article according to claim 1 wherein the top face of the holding sheet is a non-net face at a time of manufacturing of the non-woven cloth.

3. The absorbent article according to claim 1, wherein the top face of the holding sheet is processed by one selected from marble machining, needle-punching and brushing.

4. The absorbent article according to claim 1, wherein the particle diameter of 87.9% of the super absorbent polymer particle is not less than 250 μm.

* * * * *